United States Patent
Begin-Colin et al.

(10) Patent No.: US 10,624,976 B2
(45) Date of Patent: Apr. 21, 2020

(54) DENDRONIZED METALLIC OXIDE NANOPARTICLES, A PROCESS FOR PREPARING THE SAME AND THEIR USES

(71) Applicants: CENTRE NATIONAL DE LA RECHERCHE SCIENTIFIQUE, Paris (FR); UNIVERSITE DE STRASBOURG, Strasbourg (FR); HOSPICES CIVILS DE LYON, Lyons (FR); UNIVERSITE CLAUDE BERNARD LYON 1, Villeurbanne (FR)

(72) Inventors: Sylvie Begin-Colin, Achenheim (FR); Delphine Felder-Flesch, Hattstatt (FR); Claire Billotey, Lyons (FR); Benoit Pichon, Strasbourg (FR)

(73) Assignees: CENTRE NATIONAL DE LA RECHERCHE SCIENTIFIQUE, Paris (FR); UNIVESITE DE STRASBOURG, Strasbourg (FR); HOSPICES CIVILS DE LYON, Lyons (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 336 days.

(21) Appl. No.: 15/300,939

(22) PCT Filed: Apr. 1, 2015

(86) PCT No.: PCT/EP2015/057272
§ 371 (c)(1),
(2) Date: Sep. 30, 2016

(87) PCT Pub. No.: WO2015/150502
PCT Pub. Date: Oct. 8, 2015

(65) Prior Publication Data
US 2017/0014533 A1   Jan. 19, 2017

(30) Foreign Application Priority Data

Apr. 1, 2014   (EP) .................................. 14305478

(51) Int. Cl.
*A61K 9/00* (2006.01)
*A61K 49/18* (2006.01)
(Continued)

(52) U.S. Cl.
CPC ........ *A61K 49/186* (2013.01); *A61K 41/0038* (2013.01); *A61K 41/0052* (2013.01);
(Continued)

(58) Field of Classification Search
CPC .................................................. A61K 49/186
See application file for complete search history.

(56) References Cited

U.S. PATENT DOCUMENTS 5,160,725 A    11/1992  Pilgrimm
2015/0313994 A1  11/2015  Oda et al.

FOREIGN PATENT DOCUMENTS

JP    2014-001159 A    1/2014
WO    97/25073 A2      7/1997
(Continued)

OTHER PUBLICATIONS

Babes, Synthesis of Iron Oxide Nanoparticles Used as MRI Contrast Agents: A Parametric Study, Journal of Colloid and Interface Science, 1999 vol. 212, Issue 2, pp. 474-482.*
(Continued)

*Primary Examiner* — Paul W Dickinson
(74) *Attorney, Agent, or Firm* — Young & Thompson

(57) ABSTRACT

Dendronized metallic oxide nanoparticles, a process for preparing the same and their uses.

10 Claims, 11 Drawing Sheets

Figure 1A:
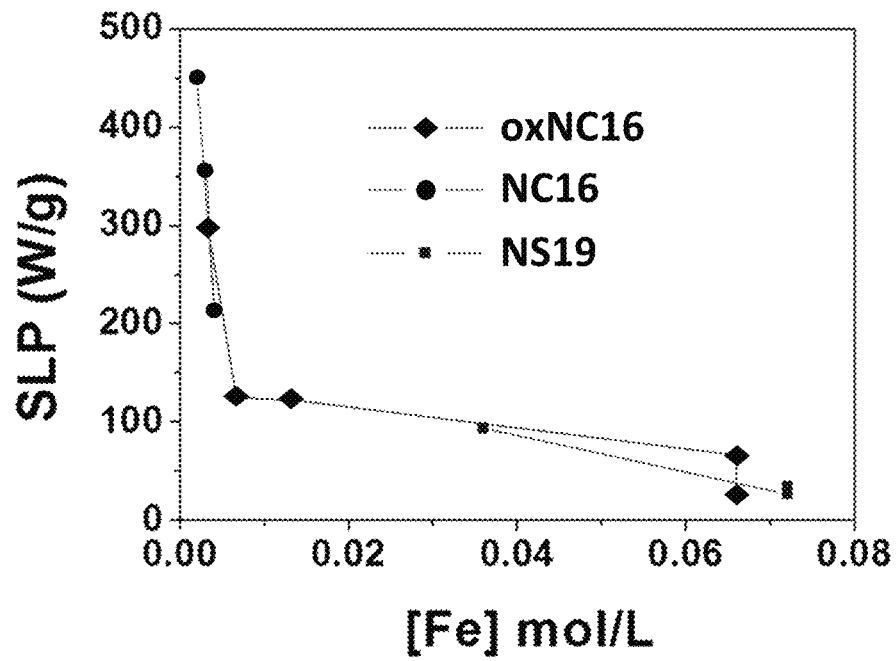

(51) Int. Cl.
- A61K 41/00 (2020.01)
- C01G 45/02 (2006.01)
- C01G 49/04 (2006.01)
- C01G 49/08 (2006.01)

(52) U.S. Cl.
CPC ...... *A61K 49/1839* (2013.01); *A61K 49/1842* (2013.01); *C01G 45/02* (2013.01); *C01G 49/04* (2013.01); *C01G 49/08* (2013.01); *C01P 2002/54* (2013.01); *C01P 2004/32* (2013.01); *C01P 2004/38* (2013.01); *C01P 2004/64* (2013.01); *C01P 2004/84* (2013.01)

(56) References Cited

FOREIGN PATENT DOCUMENTS

| WO | 2006/068653 A2 | 6/2006 |
| WO | 2011/131912 A1 | 10/2011 |
| WO | 2013/127912 A1 | 9/2013 |
| WO | 2014/042142 A1 | 3/2014 |

OTHER PUBLICATIONS

Chevallier, P. et al., "Tailored Biological Retention and Efficient Clearance of Pegylated Ultra-Small MnO Nanoparticles as Positive MRI Contrast Agents for Molecular Imaging," Journal of Materials Chemistry B, Jan. 1, 2014, vol. 2, No. 13, pp. 1779-1790.

Basly, B. et al., "Dendronized Iron Oxide Nanoparticles as Contrast Agents for MRI," Chemical Communications, Feb. 14, 2010, vol. 46, No. 6, pp. 985-987.

Issa, B. et al., "NMR Relaxation in Systems with Magnetic Nanoparticles: A Temperature Study," Journal of Magnetic Resonance Imaging (JMRI), Mar. 2014, vol. 39, No. 3, pp. 648-655.

Peng, E. et al., "Synthesis of Manganese Ferrite/Graphene Oxide Nanocomposites for Biomedical Applications," Small, Magnetic Nanoparticles, Dec. 7, 2012, vol. 8, No. 23, pp. 3620-3630.

Daou, T.J. et al., "Investigation of the Grafting Rate of Organic Molecules on the Surface of Magnetite Nanoparticles as a Function of the Coupling Agent," Sensors and Actuators B: Chemical: International Journal Devoted to Research and Development of Physical and Chemical Transducers, Sep. 20, 2007, vol. 126, No. 1, pp. 159-162.

Shon, Y. et al., "Synthesis of Nanoparticle-Cored Dendrimers by Convergent Dendritic Functionalization of Monolayer-Protected Nanoparticles," Langmuir, Jul. 2008, vol. 24, No. 13, pp. 6924-6931.

Riffle, J. S. et al., "MACRO-1307: Structure-Relaxivity Relationships of Polyether-Magnetite Nanoparticles for Enhanced Transverse Relaxivities," PACIFICHEM 2010, Dec. 15, 2010, 1 page.

Chanteau, B. et al., "Electrosteric Enhanced Stability of Functional Sub-10 nm Cerium and Iron Oxide Particles in Cell Culture Medium," Langmuir, Jul. 2, 2009, vol. 25, No. 16, pp. 9064-9070.

Garofalo, A. et al., "Efficient Synthesis of Small-Sized Phosphonated Dendrons: Potential Organic Coatings of Iron Oxide Nanoparticles," New Journal of Chemistry, Aug. 1, 2014, 14 pages.

International Search Report issued in Application No. PCT/EP2015/057272, dated Sep. 18, 2015.

European Search Report issued in Application No. EP 14 30 5478, dated Oct. 7, 2014.

* cited by examiner

DENDRONIZED METALLIC OXIDE NANOPARTICLES, A PROCESS FOR PREPARING THE SAME AND THEIR USES

The present invention relates to dendronized metallic oxide nanoparticles, a process for preparing the same and their uses.

Some of the significant and most promising applications for inorganic nanoparticles (NPs) lie in the fields of biology and biomedicine. A major issue with the development of inorganic nanoparticles for biological applications pertains to the stability and size of biofunctionalized NPs in biological media. Due to their magnetic properties and mainly their very high transverse relaxivity, superparamagnetic iron oxide nanoparticles (SPIO) with appropriate surface chemistry can be used in numerous in vivo applications such as MRI contrast enhancement, hyperthermia treatment, cell sorting, drug delivery, immunoassay, and tissue repair. In all these applications, it is mandatory to engineer the surface of SPIO NPs not only to improve biocompatibility, solubility and stability in physiological media but also to ensure a small particle size distribution (below 100 nm) after decoration and to preserve good magnetic properties, e.g. a high saturation magnetization. In addition, the small-size particles allow biodistribution of nanoparticles after intra-venous injection.

Furthermore, in the field of the synthesis and functionalization of inorganic NPs for biomedical applications, most researches aim at developing multifunctional theranostic (i.e. including therapeutic and diagnostic functions) NPs which can both identify disease states and deliver therapy and allow thus following the effect of therapy by imaging. The development of new MRI contrast agents (CAs) represents a valuable market and ultra small iron oxide NPs are of particular interest as biodegradable and non toxic nano-objects compared to other CAs families and are commercially used as $T_2$ contrast agent for MRI. Iron oxide NPs are also developed for magnetic hyperthermia (MH). When exposed to alternating magnetic fields of appropriate intensity and frequency, these NPs release heat locally (where they are concentrated), which reduces the viability of cancer cells. The MH potential is demonstrated with the favorable recent results of the "nanothermotherapy" study in clinical phase II led by a German company MagForce Nanotechnology (hospital Charité in Berlin) and with its use to enhance the sensitivity of tumor cells to chemio or radiotherapy, to facilitate release of drug or to act on cell membranes. One of the limitations of magnetic hyperthermia (MH) is the low power heating of usual magnetic NPs, requiring a local injection of large quantities of NPs.

Several natural and synthetic polymers have been employed to coat the surface of SPIO NPs: these polymers include dextran, lipids, polyethylene glycol (PEG) or polyethylene oxide (PEO) and polyvinylpyrrolidone (PVP). All the polymers used are known to be biocompatible and able to promote dispersion in aqueous media.

However, these polymer coatings are not robust and can easily be detached from particle surfaces under in vivo conditions inducing NP aggregation. Moreover, they form a large organic shell around the NPs. Both these facts lead to a lower impact of the superparamagnetic core on the water proton relaxivity and hence a lower contrast.

One objective of the present invention is to provide functionalized metallic oxide nanoparticles which are non-toxic and stable in vivo.

Another aim of the present invention is to provide functionalized metallic oxide nanoparticles having an overall mean size below 50 nm and a narrow size distribution in suspension.

Another aim of the present invention is to provide multifunctional metallic oxide nanoparticles with improved performances in MRI contrast enhancement and magnetic hyperthermia treatment providing thus added theranostic properties.

The present invention relates to a functionalized metallic oxide nanoparticle comprising or consisting of a metallic oxide nanoparticle and at least two identical or different compounds of following formula (I):

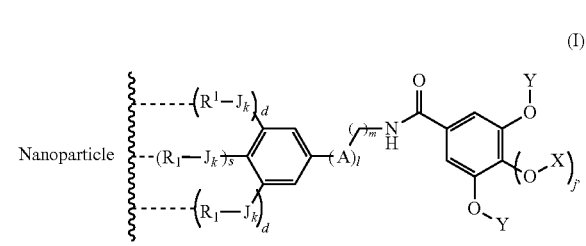

said compounds of formula (I) being iono-covalently bound to said metallic oxide nanoparticle via the $R_1$ groups, and wherein, independently from each other:

s and d are equal to 0 or 1, at least one of s and d being equal to 1, in particular s being equal to 0 and d to 1, or s being equal to 1 and d to 0;

k is equal to 0 or 1; k being preferably equal to 0;

l is equal to 0 or 1;

m is equal to 0, 1 or 2;

A represents —O—, —S— or —NH—;

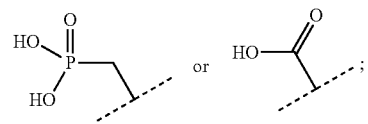

$R_1$ represents

J is chosen from:
a linear or branched $(C_1$-$C_{12})$-alkyl chain,
a PEG chain of the following formula (2a):

wherein a is an integer comprised from 1 to 10,
a chain of the following formula (2b) or (2c):

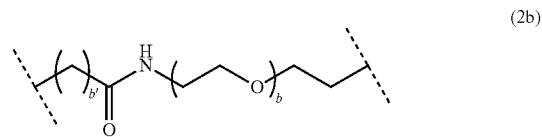

-continued

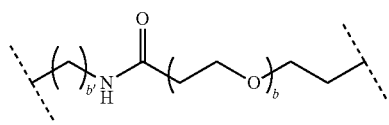
(2c)

wherein b is an integer comprised from 1 to 10, and b' is an integer comprised from 1 to 12, a chain of the following formula (2d) or (2e):

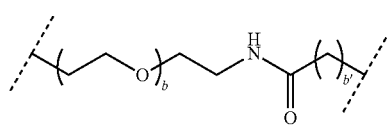
(2d)

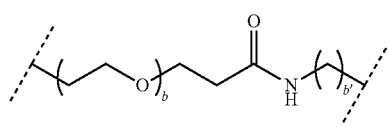
(2e)

wherein b is an integer comprised from 1 to 10, and b' is an integer comprised from 1 to 12;

X represents a group of the following formula (1):

(1)

wherein:

p is equal to 0 or 1, p being in particular equal to 1;

L is chosen from:
  a linear or branched $(C_1-C_{12})$-alkyl chain,
  a PEG chain of the following formula (2):

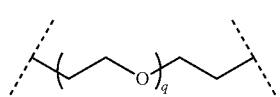
(2)

wherein q is an integer comprised from 1 to 10, a chain of the following formula (2i) or (2ii):

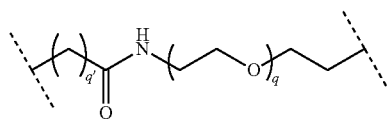
(2i)

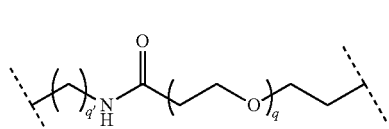
(2ii)

wherein q is an integer comprised from 1 to 10, and q' is an integer comprised from 1 to 12, a chain of the following formula (2iii) or (2iv):

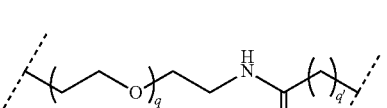
(2iii)

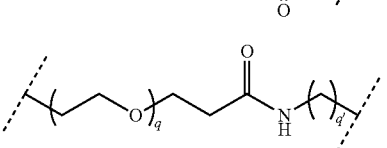
(2iv)

wherein q is an integer comprised from 1 to 10, and q' is an integer comprised from 1 to 12, L being in particular a PEG chain of the following formula (2):

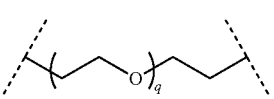
(2)

wherein q is an integer comprised from 1 to 10,

E represents a group selected from —NHCONH—, —CONH—, —COO—, —SO$_2$NH—, —NHCONH—, —NHCO—, —O—C(=O)—, —NHSO$_2$—, —O—, —S—, —NH—, —NHCOO—, —OCONH—, —NHCSNH—, —NHCSO—, —OCSNH—, —CO—NH—CO—, —CH$_2$—C≡C— or Ø, E representing in particular —O—, —NH—, —COO—, —CH$_2$—C≡C— or Ø;

R represents a group selected from:
  H,
  a linear or branched $(C_1-C_{12})$-alkyl chain,
  N$_3$,
  a ligand targeting tumor cells, abnormal cells in respect to their metabolic state or their activation state, or elements of the connective tissue of said tumor or abnormal cells,
  a radioelement chelant;
  a specific molecule recognition agent, being able to form a complex with said specific molecule, optionally linked to another dendrimer, said complex being in particular biotin-avidin complex, biotin-streptavidin complex, an antibody-antigen complex, a ligand-receptor complex, a double-stranded oligonucleotide or an adamantane-cyclodextrin complex;
  an anticancer agent; or
  a fluorophore, or a biocompatible dye;
  provided that when E represents Ø, R can only represent N$_3$, Y represents:
  a group of the following formula -L$_p$-E$_p$-R (1), as described above, or
  a dendrimer of generation n, n being equal to 1 or 2, comprising chains of rank i, i being an integer ranging from 1 to n,
  said chains of rank i being of one of the following formulae

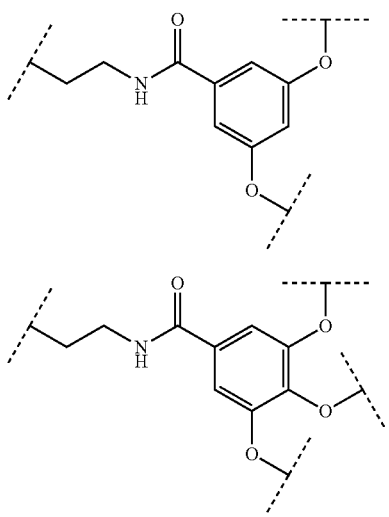

when n=1, said chain of rank i=1 being further bound to:
  to two terminal groups Z when said chains are of formula (a), or
  to three terminal groups Z when said chains are of formula (b);
when n=2, said chains of rank i being further bound to:
  for rank 1:
    to two chains of rank 2;
  for rank 2:
    to the chain of rank 1, and
    to two terminal groups Z when said chains are of formula (a), or
    to three terminal groups Z when said chains are of formula (b);
terminal groups Z represent a group of the following formula $-L_p-E_p-R$ (1), as described above;
said chains being such as when n=2, the chain of rank 1 is of formula (a), and the two chains of rank 2 are of formula (a) or (b), in particular all of formula (b);
j is equal to 0 or 1, j being equal to 0 when Y represents a dendrimer.

Interestingly, the Inventors have found that functionalized metallic oxide nanoparticles of the invention are effective at lower doses than the corresponding unfunctionalized metallic oxide nanoparticles.

In addition, metallic oxide nanoparticles functionalized with compounds of formula (I) according to the invention:
  are more stable than metallic oxide nanoparticles functionalized with linear compounds, in particular linear PEG chains;
  have better MRI properties than metallic oxide nanoparticles functionalized with other dendrimers, in particular PAMAM or PAMAM-PEG dendrimers.

By "at least two identical or different compounds of following formula (I)" is meant that at least two compounds of formula (I) are grafted to the nanoparticle. These at least two compounds of formula (I) can be identical, or different from each other, meaning that at least one of $R_1$, J, k, s, d, A, X, Y, l, m and j is different from one of said at least two compounds of formula (I) to the other.

By "iono-covalent bond" is meant that said bond involves simultaneously electrostatic forces (ionic part) and covalent forces resulting from the combination of atomic orbitals of cations and anions.

Said iono-covalent bond is in particular evidenced by the shift of the P2p band characterized by X-ray photoelectron spectroscopy (XPS) after functionalization of the nanoparticle by compounds of formula (I).

Said shift is for example described by Basly et al. (*Dalton Trans.* 2012, 42, 2146-2157).

By "linear or branched ($C_1$-$C_{12}$)-alkyl chain" is meant a hydrocarbon group with a linear or branched chain of 1 to 12 carbon atoms. Examples of said groups are methyl, ethyl, propyl, isopropyl, butyl, isobutyl, sec-butyl, tert-butyl, pentyl, isopentyl, neopentyl, tert-pentyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, and dodecyl groups.

By "terminal groups Z represent a group of the formula $-L_p-E_p-R$" is meant that in a same compound of formula (I), groups Z can be different from each other, meaning that there are at least two Z groups wherein at least one of L, E, R and p is different from one Z group to the other. For example, in a same compound of formula (I), some groups Z can comprise a linear or branched ($C_1$-$C_{12}$)-alkyl chain whereas other groups Z can comprise a PEG chain of formula (2).

In an advantageous embodiment, all the terminal Z groups comprise a PEG chain of formula (2).

In another advantageous embodiment, all the terminal Z groups are identical and comprise in particular a PEG chain of formula (2).

In an advantageous embodiment, all the terminal Z groups comprise a linear or branched ($C_1$-$C_{12}$)-alkyl chain.

In another advantageous embodiment, all the terminal Z groups are identical and comprise a linear or branched ($C_1$-$C_{12}$)-alkyl chain.

When E represents Ø, i.e. nothing, then X represents $-L_p-N_3$.

By "radioelement chelant" is meant any group able to chelate a radioelement, in particular gamma radiation emitting radioisotopes, positron emitters and/or particulate radiation emitter, beta-minus, Auger electron or alpha particles, more particularly scandium-44, scandium-47, copper-64, copper-67, gallium-67, gallium-68, rubidium-82, zirconium-89 yttrium-90, technetium-99m, indium-111, iodine-123, iodine-124, iodine-125, iodine-131, terbium-149, holmium-166, lutetium-177, rhenium-186, astatine-211, lead-212, bismuth-212, bismuth-213, radium-223, actinium-225.

Said radioelement may also be any radioisotope being possibly detected by an imaging system or a radioactivity counter, or having a radiotoxic effect.

The expression "fluorophore" refers to fluorescent molecules, such as cyanins, Alexa Fluor, fluoresceine isothiocyanate (FITC) or coumarin 343, or other fluorescent molecules well known from a man skilled in the art, in particular fluorophore used in FACS method, but without being limited to them.

The presence of a fluorophore on a nanoparticle of the present invention enables its tracking by optical imaging.

Imaging based on RAMAN spectroscopy can also be performed, with or without fluorophore.

The term "dye" refers to any natural dye liable to be used as a dye for food, pharmaceutical or cosmetical products, such as those disclosed in M. Perez-Urquiza et al (2001) J. Chrom. 917, 331-336.

Abnormal cells in respect to their metabolic state or their activation state are in particular hypoxic cells, apoptotic cells.

Said ligand targeting tumor cells, abnormal cells in respect to their metabolic state or their activation state, or elements of the connective tissue of said tumor or abnormal cells is in particular an organic or inorganic group permitting the recognition of nanoparticles of the present invention by specific cells in their membrane, cytoplasm or nucleus, and their preferential interaction.

Said ligand can represent a biological molecule produced by a living organism, or a chemically produced molecule, or any other compound that can be recognized by specific cells or an extracellular matrix, for example a DNA, a RNA, a cellular, membrane or intracellular macromolecule, in particular a protein.

Said ligand can in particular represent a biological molecule selected from the group comprising lipids, phospho lipids, glyco lipids, sterols, glycerolipids, vitamins, hormones, neurotransmitters, amino-acids, saccharides, nucleotides, antibodies, antibody fragments, nano-antibodies, trans-membrane carrier or membrane receptor ligands, nucleic or peptide aptamers.

By "antibody" is meant an immunoglobulin able to recognize an antigen and neutralize the function of said antigen. A whole antibody comprises two light chains and two heavy chains bound together by disulfide bridges.

By "antibody fragment" is meant an immunoglobulin only comprising scFv, bivalent scFv, Fab, Fab' or F(ab')$_2$ fragments.

By "nano-antibody" is meant an entity having the same structural and functional properties as a whole antibody, for example an entity constituted by two immunoglobulin heavy chains.

Said antibody may be a natural antibody, i.e. secreted by B cells or produced by hybridomas, or a recombinant antibody produced by a cell line.

Said antibody can be monoclonal or polyclonal, animal or human.

An antibody carried by a compound of the present invention enables said compound to target a specific type of cells, for example a type of tumoral cells.

More particularly, said antibody may be an antibody directed against an antigen expressed by a tumor cell type, such as carcinoembryonic antigen, overexpressed by cells of colorectal cancer, medullary thyroid, lung . . . , or an antibody which is more specific to certain types of tumor cells, such as those targeting CA-15.3 antigen overexpressed by breast cancer cells, those targeting CA125 antigen overexpressed by ovarian cancer cells, those targeting Ca-19.9 antigen overexpressed by cancer cells of the gastrointestinal tract, and in particular pancreatic carcinomas, those targeting epithelial antigen overexpressed by chondrosarcoma cells, those targeting PSMA antigen overexpressed by cells of prostate cancer, those targeting VEGF overexpressed by endothelial cells of tumor neo-vessels, or those targeting CD20 antigen expressed by normal or tumor lymphocytes, in particular those that proliferate in lymphoma, or an antibody against a protein expressed in the extracellular matrix.

For example and without limitation, said antibody may be an anti-ERBB2, anti-CA-15.3, anti-CA-19.9, anti-PSMA, anti-VEGF, anti-CTLA-4, anti-CD20, anti-CD22, anti-CD19, anti-CD33, anti-CEA, anti-MUC1, or anti-tenascin antibody.

The ligand may also be a peptide, or a small chemical molecule, i.e. a chemical molecule with a molecular weight below 20000 Da.

For example and without limitation, said ligand carried by a compound of the present invention may be the RGD peptide (cyclic or not), the NGR peptide, GM-CSF, transferrin or galactosamine, HB-19 peptide, a fragment or a multimer of said peptide, a peptide targeting the melanocortin receptor, any peptide targeting nucleolin, endostatin or angiostatin, or any other ligand of a receptor which is overexpressed on tumor cells, known to those skilled in the art.

Said ligand can also be an aptamer.

Nucleic acid aptamers can be a DNA or a RNA, produced by a combinatorial chemistry technique of in vitro selection called SELEX (systematic evolution of ligands by exponential enrichment) (Ellington et Szostak, «In vitro selection of RNA molecules that bind specific ligands.», *Nature*, vol. 346, 1990, p. 818-822).

Target entity of an aptamer can be proteins, nucleic acids, small organic compounds or whole cells.

An aptamer carried by a compound of the present invention may be an aptamer targeting a receptor or transporter, a transmembrane, intracytoplasmic or intra-nucleic protein that is present in normal cells and overexpressed in tumor cells, such as cells of acute myeloid leukemia (Sefah, Kwame, et al. "Molecular recognition of acute myeloid leukemia using aptamers." *Leukemia*, 23 (2009):235-244), or the extracellular matrix such as an aptamer anti-MMP9 targeting metalloproteinase type 9 secreted by certain types of tumor cells, including prostate or melanoma. It may also be a nucleic aptamer or protein such as AS1411 or its derivatives targeting with high affinity nucleolin, a protein overexpressed in the nucleus, the cytoplasm and the membrane of many types of tumor cells (a) Z. Cao, R. Tong, A. Mishra, W. Xu, G. C. L. Wong, J. Cheng, Y. Lu, Angew. Chem. 2009, 121, 6616-6620; Angew. Chem. Int. Ed. 2009, 48, 6494-6498; b) S. Christian, J. Pilch, M. E. Akerman, K. Porkka, P. Laakkonen, E. Ruoslahti, J. Cell Biol. 2003).

Said ligand can also be any biological molecule, such as 2-oxoglutarate or nidazoles derivatives (MISO METRO), targeting cells in hypoxia, or a molecule produced chemically, such as pentavalent DMSA targeting overexpressed proteins involved in calcium metabolism of tumor cells, such as DOPA (J Neurooncol DOI 10.1007/s11060-012-0986-1) targeting overexpression of transporters LAT1 in aggressive gliomas (J Neurooncol 99:217-225) or neuroendocrine tumors.

The ligand can in particular be selected from the chemical compounds described in Maisonial et al. *J. Med. Chem.* 2011, 54, 2745, Rbah-Vidal et al. *Eur. J. Med. Mol. Imaging* 2012, 39, 1449, Vivier et al. *Eur. J. Med. Chem.* 2011, 46, 5705 and WO2009/095872, targeting melanoma cells, and their analogues and derivatives thereof. Such a ligand has for example one of the following formulae:

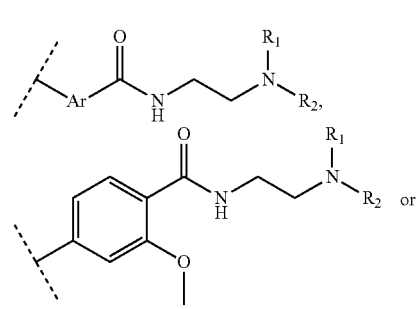

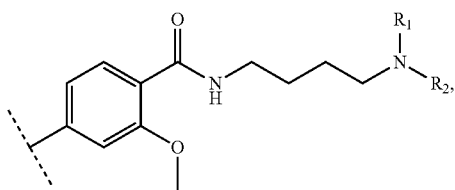

wherein $R_1$ and $R_2$ represent independently from each other a linear, branched or cyclic (C1-C6)-alkyl chain, in particular a methyl, ethyl, propyl, isopropyl, butyl, more particularly an ethyl, $R_1$ and $R_2$ being possibly linked to form a ring, $R_1$ and $R_2$ representing in particular 2-azanorborn-2-yl, Ar representing a group chosen from:

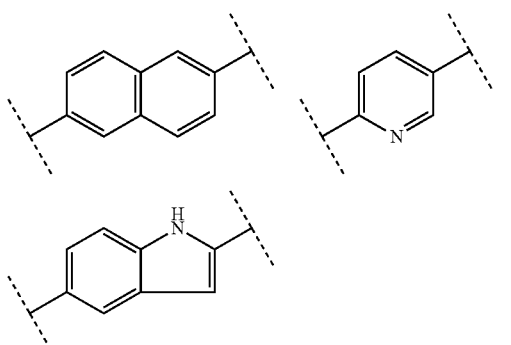

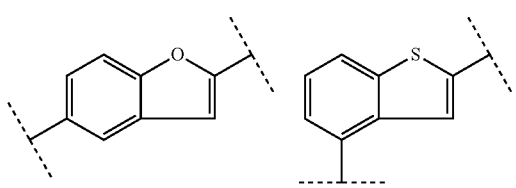

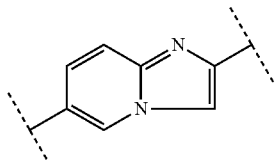

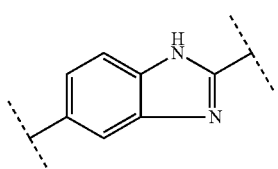

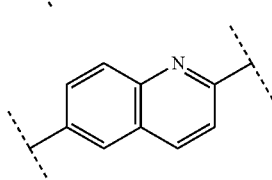

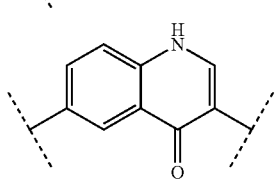

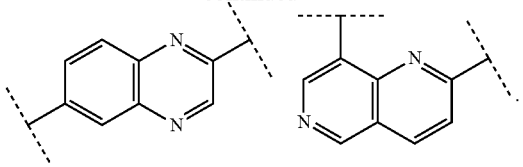

These ligands are small molecules, i.e. molecules with a molecular weight below 20000 Da, that do not disturb the good biodistribution provided in particular by the dendritic structure. On the contrary, large ligands, i.e. polymeric ligands and/or ligands with a molecular weight above 20000 Da, would alter this good biodistribution.

By "good biodistribution" is meant that the functionalized NPs are eliminated by urinary and hepatobiliary pathways without unspecific uptake especially in the RES organs and in the lungs.

Said ligand is for example of the following formula:

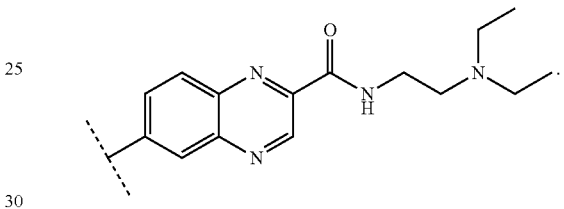

The ligand can also be selected from the chemical compounds described in *J. Nucl. Med.* 2009, 50, 1541-1547; *Eur. J. Nucl. Med. Mol. Imaging* 2012, 39, 1169-1172; and *Investigational New Drugs* 2012, 30, 1782-1790; *Sarcoma*. 2011, 2011:691608, targeting chondrosarcoma cells, and their analogues and derivatives thereof. Such a ligand has for example one of the following formulae:

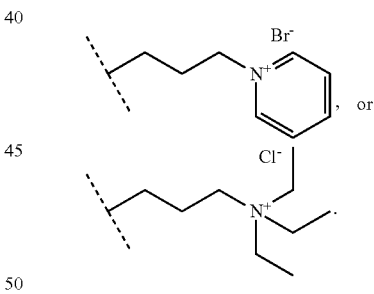

Again, these ligands are small molecules that do not disturb the good biodistribution provided in particular by the dendritic structure.

In an advantageous embodiment, said ligand is selected from the group consisting in:

V1

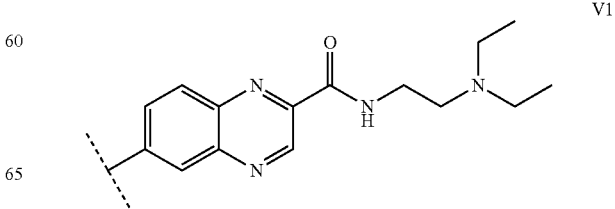

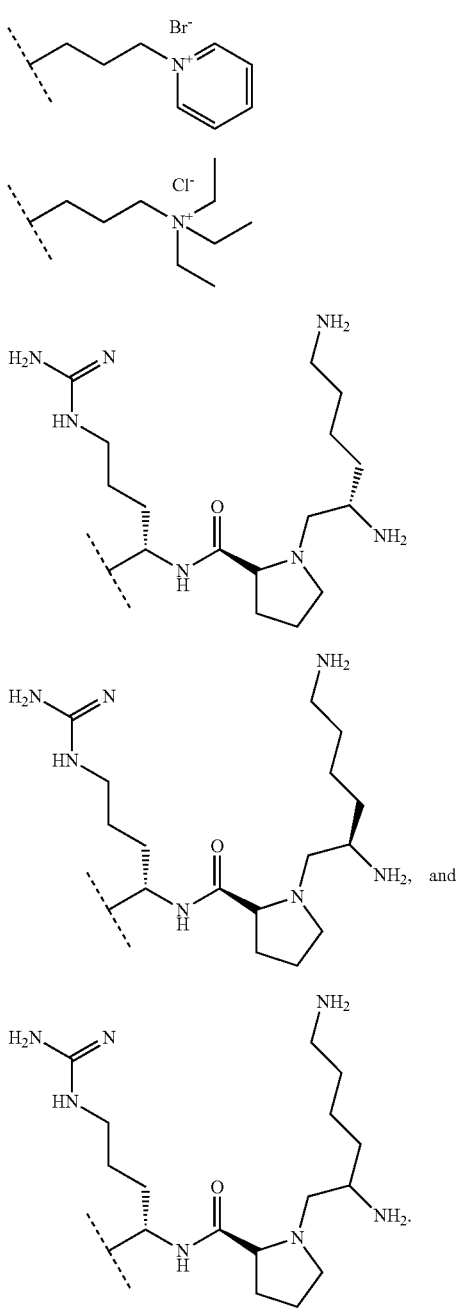

V2

V3

V4a

V4b

V4c

By "recognition agent" or "specific molecule" is meant a small organic compound, such as single-stranded oligonucleotide, a hormone or a neurotransmitter, or a macromolecule such as an antibody, a transmembrane protein, which recognizes a receptor or a protein antigen.

Said recognition agent and said specific molecule are able to form a complex, in particular the biotin-avidin complex, the biotin-streptavidin complex, an antibody-antigen complex, a ligand-receptor complex, a double-stranded oligonucleotide or an adamantane-cyclodextrin complex.

Said compound of formula (I) can bind to a second dendrimer bearing a specific molecule via recognition between said recognition agent and said specific molecule. This system combines the properties provided by the two different dendrimers.

The second dendrimer can be any dendrimer known to those skilled in the art.

In particular, said second dendrimer is of following formula ($I_A$):

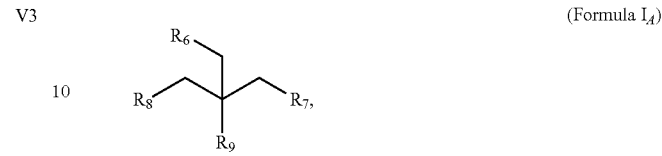

(Formula $I_A$)

wherein:

$R_9$ represents said specific molecule, $R_6$, $R_7$, $R_8$ represent independently of each other a dendritic group of generation $1 \leq n \leq 7$, said dendrimeric group comprising:

(a) a core comprising an amine group and two carbonyl groups, of following formula A:

(Formula A)

(b) terminal groups Ra chosen from
(i) terminal group $Ra_1$ of following formula

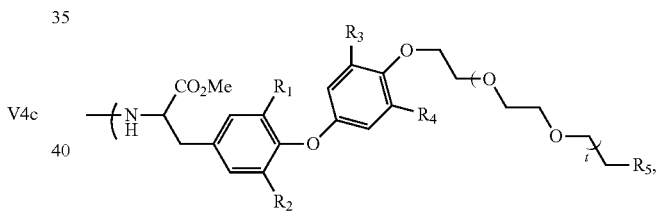

wherein:
$R_1$, $R_2$, $R_3$ and $R_4$ represent I or At,
$R_5$ represents —NHBoc or

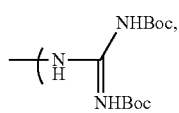

t represents an integer superior to 0 and inferior to 7, or
(ii) terminal group $Ra_e$ of following formula

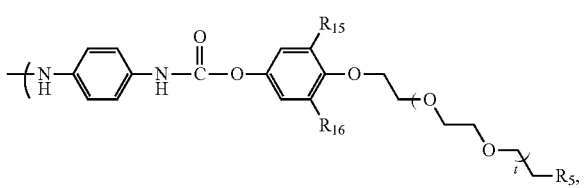

wherein:

$R_{15}$, $R_{16}$ represent F, —$NO_2$, Cl, Br, $CH_2OMs$, $CH_2OTs$, $CH_2Br$ or $CH_2Cl$ $R_5$ represents —NHBoc or

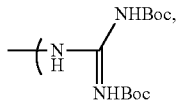

t represents an integer superior to 0 and inferior to 7;

(c) and when said dendritic group is not of generation 1, said dendritic group further comprises dendrons of following formula B:

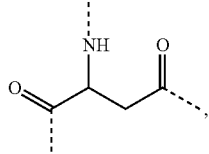

(Formula B)

said dendritic group of generation n, n≥1, comprising n−1 ranks of dendrons, the core of formula A being such as:
said core amine group is bound to the carbon chain of formula $I_A$,
both core carbonyl groups are bound
(i) to the amine group of a terminal group Ra, when said dendritic group is of generation 1, or
(ii) to the amine group of a dendron of rank 1 of said dendritic group, when said dendritic group is not of generation 1, or
(iii) to a group —OH, provided said core carbonyl groups are not both bound to a group —OH, and
terminal group Ra being such as:
said amine group of terminal group Ra is bound:
  (i) to a core carbonyl group, when said dendritic group is of generation 1, or
  (ii) to a carbonyl group of a dendron of last rank (rank n−1) o the dendritic group, when said dendritic group is not of generation 1, and
a dendron of formula B and of rank m, 1≤m≤n−1, being such as:
the amine group of said dendron of rank m is bound
  to a core carbonyl group, when said dendron is of rank 1, or
  to a carbonyl group of a dendron of previous rank m−1, when said dendron rank is superior to 1;
both carbonyl groups of said dendrons are bound:
  to the amine group of a terminal group Ra, when said dendron is of last rank, or
  to the amine group of a dendron of next rank m+1, when said dendron is not of last rank, or
  to a group —OH, provided said carbonyl groups of said dendritic group are not both bound to a group —OH.

Iodine may be replaced by astatine, in particular astatine-211, according to a reaction that is well known to those skilled in the art.

The present invention relates to a functionalized metallic oxide nanoparticle comprising or consisting of a metallic oxide nanoparticle and at least two identical or different compounds of following formula (I):

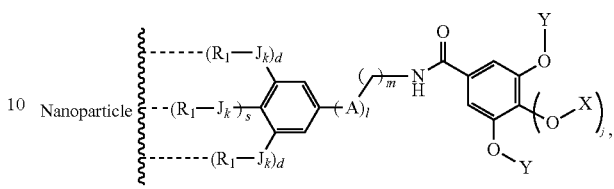

(I)

said compounds of formula (I) being iono-covalently bound to said metallic oxide nanoparticle via the $R_1$ groups, and wherein, independently from each other:

s and d are equal to 0 or 1, at least one of s and d being equal to 1, in particular s being equal to 0 and d to 1, or s being equal to 1 and d to 0;

k is equal to 0 or 1; k being preferably equal to 0;

l is equal to 0 or 1;

m is equal to 0, 1 or 2;

A represents —O—, —S— or —NH—;

$R_1$ represents

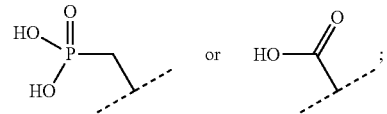

J is chosen from:
a linear or branched ($C_1$-$C_{12}$)-alkyl chain,
a PEG chain of the following formula (2a):

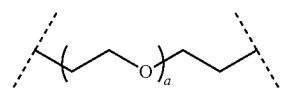

(2a)

wherein a is an integer comprised from 1 to 10, a chain of the following formula (2b) or (2c):

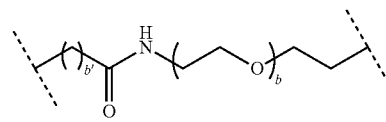

(2b)

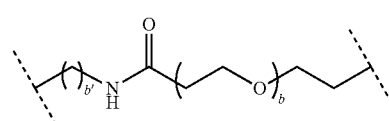

(2c)

wherein b is an integer comprised from 1 to 10, and b' is an integer comprised from 1 to 12, a chain of the following formula (2d) or (2e):

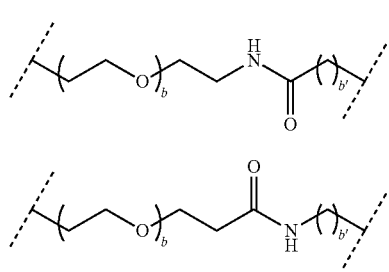

wherein b is an integer comprised from 1 to 10, and b' is an integer comprised from 1 to 12;

X represents a group of the following formula (1):

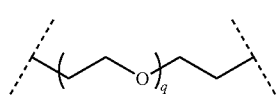

wherein:
p is equal to 0 or 1, p being in particular equal to 1;
L is chosen from:
 a linear or branched $(C_1-C_{12})$-alkyl chain,
 a PEG chain of the following formula (2):

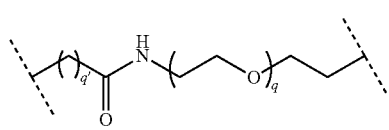

wherein q is an integer comprised from 1 to 10,
a chain of the following formula (2i) or (2ii):

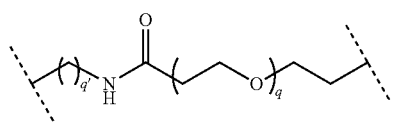

wherein q is an integer comprised from 1 to 10, and q' is an integer comprised from 1 to 12,
a chain of the following formula (2iii) or (2iv):

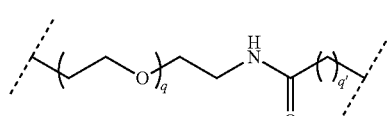

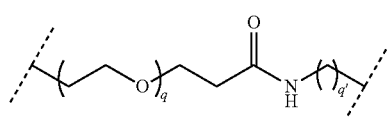

wherein q is an integer comprised from 1 to 10, and q' is an integer comprised from 1 to 12, L being in particular a PEG chain of the following formula (2):

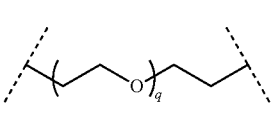

wherein q is an integer comprised from 1 to 10,
E represents a group selected from —NHCONH—, —CONH—, —COO—, —SO$_2$NH—, —NHCONH—, —NHCO—, —O—C(=O)—, —NHSO$_2$—, —O—, —S—, —NH—, —NHCOO—, —OCONH—, —NHCSNH—, —NHCSO—, —OCSNH—, —CO—NH—CO—, —CH$_2$—C≡C— or Ø, E representing in particular —O—, —NH—, —COO—, —CH$_2$—C≡C— or Ø;

R represents a group selected from:
 H,
 a linear or branched $(C_1-C_{12})$-alkyl chain,
 N$_3$,
 a ligand targeting tumor cells, abnormal cells in respect to their metabolic state or their activation state, or elements of the connective tissue of said tumor or abnormal cells,
 a radioelement chelant;
 a specific molecule recognition agent, being able to form a complex with said specific molecule, optionally linked to another dendrimer, said complex being in particular biotin-avidin complex, biotin-streptavidin complex, an antibody-antigen complex, a ligand-receptor complex, a double-stranded oligonucleotide or an adamantane-cyclodextrin complex;
 an anticancer agent; or
 a fluorophore, or a biocompatible dye;
 provided that when E represents Ø, R can only represent N$_3$, Y represents:
 a group of the following formula -L$_p$-E$_p$-R (1), as described above, or
 a dendrimer of generation n, n being equal to 1 or 2, comprising chains of rank i, i being an integer ranging from 1 to n,
 said chains of rank i being of one of the following formulae

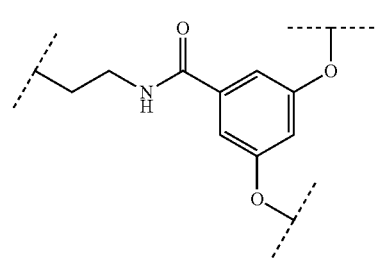

-continued

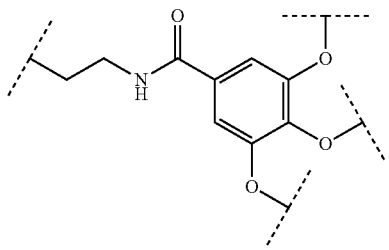
(b)

when n=1, said chain of rank i=1 being further bound to:
to two terminal groups Z when said chains are of formula (a), or
to three terminal groups Z when said chains are of formula (b);
when n=2, said chains of rank i being further bound to:
for rank 1:
to two chains of rank 2;
for rank 2:
to the chain of rank 1, and
to two terminal groups Z when said chains are of formula (a), or
to three terminal groups Z when said chains are of formula (b);
terminal groups Z represent a group of the following formula $-L_p-E_p-R$ (1), as described above;
said chains being such as when n=2, the chain of rank 1 is of formula (a), and the two chains of rank 2 are of formula (a) or (b), in particular all of formula (b);
j is equal to 0 or 1, j being equal to 0 when Y represents a dendrimer,
said metallic oxide nanoparticle being:
a homogenous metallic oxide nanoparticle selected from the group consisting in:
a metallic oxide of the following formula (II):

$M_xO_y$ (II)

wherein:
M is a metal selected from the group constituted of Fe and Mn, M representing in particular Fe,
x and y are positive integers such as $y=(x\cdot v)/2$, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, or $\gamma Fe_2O_3$;
a metallic oxide of the following formula (III):

$Fe_{3-y}M'_yO_4$ (III)

wherein M' is a metal selected from the group constituted of Zn, Co, Mn, Ni and Mg, y being such as $0<y\leq1$,
said metallic oxide of formula (III) being in particular $M'Fe_2O_4$,
or
a core-shell metallic oxide nanoparticle,
said core being selected from the group constituted of:
a metallic oxide of the following formula (II):

$M_xO_y$ (II)

wherein:
M is a metal selected from the group constituted of Fe, Mn.

x and y are positive integers such as $y=(x\cdot v)/2$, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, $\gamma Fe_2O_3$, FeO, MnO,
a metallic oxide of the following formula (III):

$Fe_{3-y}M'_yO_4$ (III)

wherein M' is a metal selected from the group constituted of Zn, Co, Mn, Ni and Mg, y being such as $0<y\leq1$, said metallic oxide of formula (III) being in particular $M'Fe_2O_4$,
said shell being selected from the group constituted of:
a metallic oxide of the following formula (II):

$M_xO_y$ (II)

wherein:
M is a metal selected from the group constituted of Fe and Mn.
x and y are positive integers such as $y=(x\cdot v)/2$, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, $\gamma Fe_2O_3$, MnO,
a metallic oxide of the following formula (III):

$Fe_{3-y}M'_yO_4$ (III)

wherein M' is a metal selected from the group constituted of Zn, Co, Mn, Ni and Mg, y being such as $0<y\leq1$, said metallic oxide of formula (III) being in particular $M'Fe_2O_4$,
Au,
provided that:
said core and said shell are not the same metallic oxide,
said metallic oxide nanoparticle:
being a magnetic resonance imaging contrast agent, and
having a sufficient heating power for a magnetic hyperthermia treatment.

By "contrast agent" is meant an agent that can artificially modify the contrast between tissues or cells of different types to visualize an anatomical or pathological structure, more especially cells, such as tumor cells, which presents naturally no specific contrast and is difficult to distinguish from surrounding tissue.

By "having a sufficient heating power for a magnetic hyperthermia treatment", is meant that said nanoparticle can produce he at under an alternating magnetic field that is acceptable for an in vivo treatment.

In an advantageous embodiment, the present invention relates to the functionalized metallic oxide nanoparticle described above, having
a $r_2$ relaxivity value above $60\ s^{-1}\ mM^{-1}$, and a $r_1$ relaxivity ratio such as the $r_2/r_1$ ratio is above 6,
said $r_1$ and $r_2$ values being measured with a nanoparticle having a mean hydrodynamic size of about 15 nm, and under a magnetic field of 1.41 T at 37° C.,
and
a specific absorption rate above 80 W/g, said rate being measured at a concentration of iron and/or magnetic metallic atom in said nanoparticle of 0.01 mol/L, at a field frequency of 700 kHz with a field amplitude of 27 mT and at 37° C.

By $r_2$ relaxivity value is meant a value corresponding to the ability of said nanoparticle, in aqueous media, to decrease the $T_2$ spin-spin relaxation rate (or increase $1/T_2$) of the surrounding water proton spins.

Such a $r_2$ value can be determined by graphing changes in $1/T_2$-$1/T_{water}$ relaxation rate at different nanoparticle concentrations, the slope of the line representing $r_2$.

$T_2$ time can be measured by multi-echo pulse sequence.

T2 contrast agents, called negative contrast agents, reduce transverse T2 relaxation time (or increase R2) and lead to the collapse of the signal (hyposignal). They thus increase the dark contrast of the image in MRI.

By $r_1$ relaxivity value is meant a value corresponding to the ability of said nanoparticle, in aqueous media, to decrease the $T_1$ spin-lattice relaxation rate (or increase $1/T_1$) of the surrounding water proton spins.

Such a $r_1$ value can be determined by graphing changes in $1/T_1$-$1/T_{water}$ relaxation rate at different nanoparticle concentrations, the slope of the line representing $r_1$.

$T_1$ time can be measured by multi-echo pulse sequence.

T1 contrast agents, called positive contrast agents, reduce the longitudinal relaxation time T1 (or increase R1) and raise the measured signal (hypersignal). They enhance white contrasts of the image in MM.

By mean hydrodynamic size is meant the size of the functionalized metallic oxide, in suspension in water.

Mean hydrodynamic size can be determined by dynamic light scattering (DLS), a method for granulometric measurements.

By specific absorption rate (SAR) is meant the power dissipated by the nanoparticle subjected to an alternating magnetic field.

SAR measurements at a field frequency of 700 kHz with a field amplitude of 27 mT and at 37° C. can be conducted with commercial equipments or laboratory-made device described by Hai et al. (*J. Colloid Interface Sci.* 2010, 346, 3742). It consists of a resonant RLC circuit with a 16 mm coil. The coil and the sample are thermalized at 37° C. The temperature can be probed with a fluoro-optic fiber thermometer (Luxtron STF-2, BFiOPTiLAS SAS).

The specific loss power (SAR) is calculate using the equation $$SAR = \left(\frac{C_{water} V_S}{m}\right)\frac{dT}{dt}$$

wherein $C_{water}$ is the volume specific heat capacity of the water ($C_{water}$=4185 J L$^{-1}$ K$^{-1}$), and the contributions from the nanoparticle are neglected. $V_s$ is the volume of the sample. T is the temperature of the sample (in Kelvin) and m is the mass of the sample.

A field amplitude of 27 mT corresponds to a value of 21 kA/m.

In an advantageous embodiment, the present invention relates to the functionalized metallic oxide nanoparticle described above, comprising an iron oxide.

The invention also relates to a functionalized magnetic metallic oxide nanoparticle comprising an iron oxide of formula (II) or (III).

In an advantageous embodiment, the present invention relates to the functionalized metallic oxide nanoparticle described above, being a homogenous metallic oxide nanoparticle selected from the group consisting in:
a metallic oxide of the following formula (II):

$$FeO_xO_y \tag{II}$$

wherein:
x and y are positive integers such as y=(x·v)/2, wherein v is the average oxidation state of M in $M_xO_y$, said metallic oxide of formula (II) being in particular $Fe_3O_4$, $Fe_{3-\delta}O_4$ with δ being such as 0<δ<1/3, or $\gamma Fe_2O_3$;

a metallic oxide of the following formula (III):

$$Fe_{3-y}M'_yO_4 \tag{III}$$

wherein M' is a metal selected from the group constituted of Zn, Co, Mn, Ni and Mg, y being such as 0<y≤1, said metallic oxide of formula (III) being in particular M'Fe$_2$O$_4$, or a core-shell metallic oxide nanoparticle,
said core being selected from the group constituted of:
a metallic oxide of the following formula (II):

$$M_xO_y \tag{II}$$

wherein:
M is a metal selected from the group constituted of Fe, Mn.

x and y are positive integers such as y=(x·v)/2, wherein v is the average oxidation state of M in $M_xO_y$, said metallic oxide of formula (II) being in particular $Fe_3O_4$, $Fe_{3-\delta}O_4$ with δ being such as 0<δ<1/3, $\gamma Fe_2O_3$, FeO, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as 0<y≤1, said metallic oxide of formula (III) being in particular M'Fe$_2$O$_4$, said shell being selected from the group constituted of:
a metallic oxide of the following formula (II):

$$M_xO_y \tag{II}$$

wherein:
M is a metal selected from the group constituted of Fe and Mn.

x and y are positive integers such as y=(x·v)/2, wherein v is the average oxidation state of M in $M_xO_y$, said metallic oxide of formula (II) being in particular $Fe_3O_4$, $Fe_{3-\delta}O_4$ with δ being such as 0<δ<1/3, $\gamma Fe_2O_3$, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as 0<y≤1, said metallic oxide of formula (III) being in particular M'Fe$_2$O$_4$, Au, provided that:
said core and said shell are not the same metallic oxide,
said core being of formula (II) wherein M is Fe or of formula (III), or said shell being of formula (II) wherein M is Fe or of formula (III).

Said iron oxide of formula FeO$_x$O$_y$ (II) is magnetic.

Said metallic oxide of formula (III) is a magnetic doped iron oxide.

In an advantageous embodiment, the present invention relates to the functionalized metallic oxide nanoparticle described above, said nanoparticle having a $r_1$ relaxivity value comprised from 4 to 5 s$^{-1}$ mM$^{-1}$, and a $r_1$ relaxivity ratio such as the $r_2/r_1$ ratio is comprised from 4 to 5, $r_1$ and $r_2$ values being measured with a nanoparticle having a mean hydrodynamic size of about 15 nm, under a magnetic field of 1.41 T at 37° C.

In an advantageous embodiment, the present invention relates to the functionalized metallic oxide nanoparticle described above, said nanoparticle having a $r_1$ relaxivity value comprised from 4 to 5 $s^{-1}$ $mM^{-1}$, and a $r_1$ relaxivity ratio such as the $r_2/r_1$ ratio is comprised from 4 to 5, $r_1$ and $r_2$ values being measured with a nanoparticle having a mean hydrodynamic size of about 15 nm, under a magnetic field of 1.41 T at 37° C., and a specific absorption rate above 80 W/g, said rate being measured at a concentration of iron and/or magnetic metallic atom in said nanoparticle of 0.01 mol/L, at a field frequency of 700 kHz with a field amplitude of 27 mT and at 37° C.

In an advantageous embodiment, the present invention relates to the functionalized metallic oxide nanoparticle described above, comprising a manganese oxide.

In an advantageous embodiment, the present invention relates to the functionalized metallic oxide nanoparticle described above, the largest dimension of which being comprised from 5 to 30 nm, in particular from 5 to 20 nm, said largest dimension being more particularly of 5, 6, 7, 8, 9, 10, 11, 12, 13, 14, 15, 16, 17, 18, 19 or 20 nm.

In an advantageous embodiment, the present invention relates to the functionalized metallic oxide nanoparticle described above, said nanoparticle being:

cubic, rodshaped, octopod-shaped or nanoplatelet-shaped, and/or a core-shell metallic oxide nanoparticle.

In an advantageous embodiment, the present invention relates to the functionalized metallic oxide nanoparticle described above, said nanoparticle comprising at least two compounds of formula (I), wherein p is equal to 1.

The linkers L, in particular when they consist in or comprise a PEG, allow compounds of formula (I) to have an increased hydrophilicity, compared to compounds that would not comprise said linkers. In addition, the linkers L allow entities of importance, in particular the nanoparticle itself and the periphery of the dendrimer, to be remote enough to limit their interactions that could be harmful, especially for the terminal groups R.

In an advantageous embodiment, the present invention relates to the functionalized metallic oxide nanoparticle described above, said nanoparticle comprising at least two compounds of formula (I), wherein p is equal to 1 and L represents a PEG chain of the following formula (2):

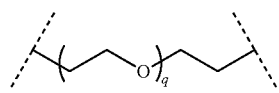

(2)

q being an integer comprised from 1 to 10.

In an advantageous embodiment, the present invention relates to the functionalized metallic oxide nanoparticle described above, said nanoparticle comprising at least two compounds of formula (I), wherein l is equal to 1, m is to 2 and A represents —O—, corresponding to the following formula:

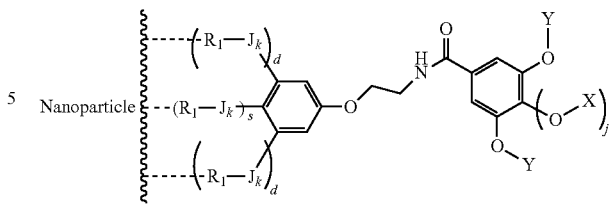

wherein $R_1$, J, k, s, d, X, Y and j are as described above.

In an advantageous embodiment, the present invention relates to the functionalized metallic oxide nanoparticle described above, said nanoparticle comprising at least two compounds of formula (I), wherein s is equal to 1 and d to 0, corresponding to the following formula:

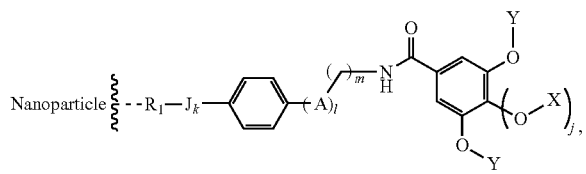

wherein $R_1$, J, k, A, l, m, X, Y and j are as described above.

In an advantageous embodiment, the present invention relates to the functionalized metallic oxide nanoparticle described above, said nanoparticle comprising at least two compounds of formula (I), wherein s is equal to 0 and d to 1, corresponding to the following formula:

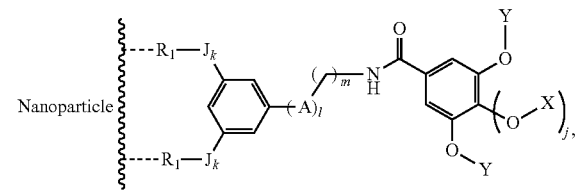

wherein $R_1$, J, k, A, l, m, X, Y and j are as described above.

In an advantageous embodiment, the present invention relates to the functionalized metallic oxide nanoparticle described above, said nanoparticle comprising at least two compounds of formula (I), wherein s and d are equal to 1, corresponding to the following formula:

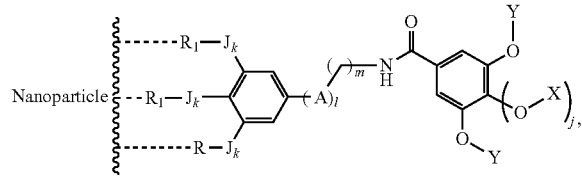

wherein $R_1$, J, k, A, l, m, X, Y and j are as described above.

In an advantageous embodiment, the present invention relates to the functionalized metallic oxide nanoparticle described above, said nanoparticle comprising at least two compounds of formula (I), wherein l is equal to 1, m is to 2 and A represents —O—, and wherein s is equal to 1 and d to 0, corresponding to the following formula:

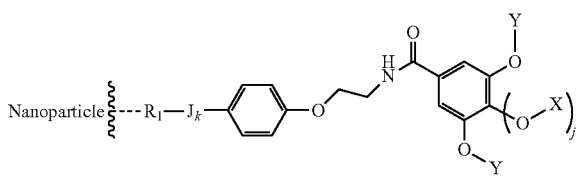

wherein $R_1$, J, k, X, Y and j are as described above.

In an advantageous embodiment, the present invention relates to the functionalized metallic oxide nanoparticle described above, said nanoparticle comprising at least two compounds of formula (I), wherein 1 is equal to 1, m is to 2 and A represents —O—, and wherein s is equal to 0 and d to 1, corresponding to the following formula:

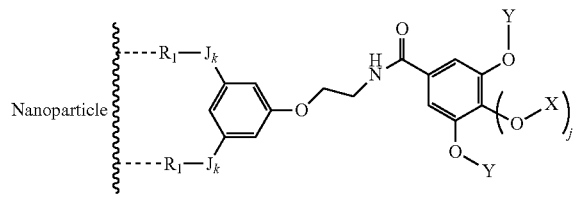

wherein $R_1$, J, k, X, Y and j are as described above.

In an advantageous embodiment, the present invention relates to the functionalized metallic oxide nanoparticle described above, said nanoparticle comprising at least two compounds of formula (I), wherein $R_1$ represents —CH$_2$PO$_3$H$_2$.

In an advantageous embodiment, the present invention relates to the functionalized metallic oxide nanoparticle described above, said nanoparticle being substantially spherical.

In an advantageous embodiment, the present invention relates to the functionalized metallic oxide nanoparticle described above, said nanoparticle being substantially spherical, the mean diameter of said nanoparticle being comprised from 5 to 30 nm, in particular from 5 to 20 nm.

Nanoparticles with a mean diameter near the superparamagnetic/blocked single domain size threshold estimated currently around 20 nm are known to favour enhanced hyperthermia properties.

By "diameter of said nanoparticle" is meant the diameter of the non-functionalized nanoparticle, i.e. the nanoparticle whereon no compound of formula (I) is bound.

The mean diameter is for example determined by measuring the diameter of at least 300 nanoparticles on Transmission Electron Microscopy (TEM) images. The distribution is generally monomodale, and the mean diameter is determined with a standard deviation.

In an advantageous embodiment, the present invention relates to the functionalized metallic oxide nanoparticle described above, said nanoparticle being substantially cubic.

In an advantageous embodiment, the present invention relates to the functionalized metallic oxide nanoparticle described above, said nanoparticle being substantially cubic, the mean edge length of said nanoparticle being comprised from 10 nm to 40 nm, in particular from 10 to 20 nm.

In an advantageous embodiment, the present invention relates to the functionalized metallic oxide nanoparticle described above, said nanoparticle being substantially rod-shaped.

By "rod-shape" is meant a nanowire, in particular a solid enclosed by a cylinder, more particularly a right circular cylinder, and two surfaces intersecting said cylinder, more particularly two planes perpendicular to the axis of said cylinder.

In an advantageous embodiment, the present invention relates to the functionalized metallic oxide nanoparticle described above said nanoparticle being substantially rod-shaped, the mean length of said nanoparticle being comprised from 20 nm to 500 nm, the mean diameter of said nanoparticle being in particular comprised from 5 nm to 50 nm.

In an advantageous embodiment, the present invention relates to the functionalized metallic oxide nanoparticle described above, said nanoparticle being substantially octopod-shaped, said octopod comprising 8 sharp corners and 12 edges.

By "octopod comprising 8 sharp corners and 12 edges" is meant a deformed cube, the faces of which being concave.

In an advantageous embodiment, the present invention relates to the functionalized metallic oxide nanoparticle described above, said nanoparticle being substantially octopod-shaped, said octopod comprising 8 sharp corners and 12 edges, the mean distance between two neighboring corners being comprised from 10 nm to 50 nm.

In an advantageous embodiment, the present invention relates to the functionalized metallic oxide nanoparticle described above, said nanoparticle being substantially nanoplatelet-shaped.

By "nanoplatelet-shaped" is meant a shape of regular, in particular constant, thickness, said thickness being less than the largest dimension of said shape, in particular more than 2, 5 or 10 times less.

In an advantageous embodiment, the present invention relates to the functionalized metallic oxide nanoparticle described above, said nanoparticle being substantially nanoplatelet-shaped, the largest dimension of which being comprised from 5 to 50 nm, in particular from 5 to 20 nm, more particularly from 10 to 20 nm.

The shape of the nanoparticles of the invention (cubic shape, rod shape, octopod, nanoplatelet-shaped) affects the magnetocrystalline anisotropy, which contributes to the heating power and thus the hyperthermia properties of said nanoparticles by preserving imaging properties.

In an advantageous embodiment, the present invention relates to the functionalized metallic oxide nanoparticle described above, said metallic oxide nanoparticle being:
a homogenous metallic oxide nanoparticle selected from the group consisting in:
a metallic oxide of the following formula (II):

wherein:
M is a metal selected from the group constituted of Fe and Mn, M representing in particular Fe,
x and y are positive integers such as y=(x·v)/2, wherein v is the average oxidation state of M in $M_xO_y$,
said metallic oxide of formula (II) being in particular Fe$_3$O$_4$, Fe$_{3-\delta}$O$_4$ with δ being such as 0<δ<1/3, or γFe$_2$O$_3$;
a metallic oxide of the following formula (III):

wherein M' is a metal selected from the group constituted of Zn, Co, Mn, Ni and Mg, y being such as 0<y≤1,
said metallic oxide of formula (III) being in particular M'Fe$_2$O$_4$, or
a core-shell metallic oxide nanoparticle,
said core being selected from the group constituted of:
a metallic oxide of the following formula (II):

$$M_xO_y \qquad (II)$$

wherein:
M is a metal selected from the group constituted of Fe, Mn.
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, $\gamma Fe_2O_3$, FeO, MnO,
a metallic oxide of the following formula (III):

$$Fe_{3-y}M'_yO_4 \qquad (III)$$

wherein M' is a metal selected from the group constituted of Zn, Co, Mn, Ni and Mg, y being such as $0<y\leq 1$, said metallic oxide of formula (III) being in particular $M'Fe_2O_4$,
said shell being selected from the group constituted of:
a metallic oxide of the following formula (II):

$$M_xO_y \qquad (II)$$

wherein:
M is a metal selected from the group constituted of Fe and Mn.
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, $\gamma Fe_2O_3$, MnO,
a metallic oxide of the following formula (III):

$$Fe_{3-y}M'_yO_4 \qquad (III)$$

wherein M' is a metal selected from the group constituted of Zn, Co, Mn, Ni and Mg, y being such as $0<y\leq 1$, said metallic oxide of formula (III) being in particular $M'Fe_2O_4$,
Au,
provided that:
said core and said shell are not the same metallic oxide.

By "homogenous" is meant that said metallic oxide nanoparticle is constituted by said metallic oxide of the following formula (II) or (III).

When the magnetite $Fe_3O_4$ phase is doped by metallic atoms, it modifies its magnetic properties: the saturation magnetization and the coercivity, the anisotropy energy. For example cobalt in ferrite is known to strongly increase the anisotropy energy, and manganese the saturation magnetization.

In an advantageous embodiment, the present invention relates to the functionalized metallic oxide nanoparticle described above, said metallic oxide being a homogenous metallic oxide nanoparticle selected from the group consisting in:
a metallic oxide of the following formula (II):

$$M_xO_y \qquad (II)$$

wherein:
M is a metal selected from the group constituted of Fe and Mn, M representing in particular Fe,
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, or $\gamma Fe_2O_3$;

a metallic oxide of the following formula (III):

$$Fe_{3-y}M'_yO_4 \qquad (III)$$

wherein M' is a metal selected from the group constituted of Zn, Co, Mn, Ni and Mg, y being such as $0<y\leq 1$,
said metallic oxide of formula (III) being in particular $M'Fe_2O_4$.

In an advantageous embodiment, the present invention relates to the functionalized metallic oxide nanoparticle described above, said metallic oxide being of formula (II), said metallic oxide being different from FeO.

In said embodiment, said nanoparticle is in particular in contact with an oxidative atmosphere, such as air, in which FeO would not be stable and would oxidize to form a core-shell type nanoparticle.

In an advantageous embodiment, the present invention relates to the functionalized metallic oxide nanoparticle described above, said metallic oxide nanoparticle being a homogenous metallic oxide nanoparticle selected from the group constituted of $Fe_3O_4$, $Fe_{3-\delta}O_4$ with $\delta$ being such as $0<\delta<1/3$, $\gamma Fe_2O_3$ and $M'Fe_2O_4$, wherein M' is a metal selected from the group constituted of Zn, Co, Mn, Ni and Mg.

In an advantageous embodiment, the present invention relates to the functionalized metallic oxide nanoparticle described above, said metallic oxide nanoparticle being of core-shell metallic oxide structure,
said core being selected from the group constituted of:
a metallic oxide of the following formula (II):

$$M_xO_y \qquad (II)$$

wherein:
M is a metal selected from the group constituted of Fe, Mn.
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, $\gamma Fe_2O_3$, FeO, MnO,
a metallic oxide of the following formula (III):

$$Fe_{3-y}M'_yO_4 \qquad (III)$$

wherein M' is a metal selected from the group constituted of Zn, Co, Mn, Ni and Mg, y being such as $0<y\leq 1$, said metallic oxide of formula (III) being in particular $M'Fe_2O_4$,
said shell being selected from the group constituted of:
a metallic oxide of the following formula (II):

$$M_xO_y \qquad (II)$$

wherein:
M is a metal selected from the group constituted of Fe and Mn.
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with $\delta$ being such as $0<\delta<1/3$, $\gamma Fe_2O_3$, MnO,
a metallic oxide of the following formula (III):

$$Fe_{3-y}M'_yO_4 \qquad (III)$$

wherein M' is a metal selected from the group constituted of Zn, Co, Mn, Ni and Mg, y being such as $0<y\leq 1$, said metallic oxide of formula (III) being in particular $M'Fe_2O_4$,
provided that:
said core and said shell are not the same metallic oxide.

The specific nanostructure of the core-shell nanoparticles of the invention enable cooperative magnetism, which contributes to the heating power and thus the hyperthermia properties of said nanoparticles.

In an advantageous embodiment, the present invention relates to the functionalized metallic oxide nanoparticle described above, said metallic oxide nanoparticle being of core-shell metallic oxide structure, wherein said shell is different from FeO.

In said embodiment, said nanoparticle is in particular in contact with an oxidative atmosphere, such as air, in which FeO would not be stable and would oxidize.

In an advantageous embodiment, the present invention relates to the functionalized metallic oxide nanoparticle described above, said metallic oxide nanoparticle being of core-shell metallic oxide structure and selected from the group constituted of FeO@Fe$_3$O$_4$, Fe$_3$O$_4$@MnO, Fe$_3$O$_4$@Au and M'Fe$_2$O$_4$@M"Fe$_2$O$_4$, wherein M' is a metal selected from the group constituted of Zn, Co, Mn, Ni and Mg and wherein M" is a metal selected from the group constituted of Zn, Co, Mn, Ni and Mg, M' being different from M".

In an advantageous embodiment, the present invention relates to the functionalized metallic oxide nanoparticle described above, said nanoparticle being cubic, rodshaped, octopod-shaped or nanoplatelet-shaped.

The invention also relates to a non spherical functionalized metallic oxide nanoparticle.

In an advantageous embodiment, the present invention relates to the functionalized metallic oxide nanoparticle described above, said nanoparticle being cubic, rodshaped, octopod-shaped or nanoplatelet-shaped, said metallic oxide nanoparticle being:
a homogenous metallic oxide nanoparticle selected from the group consisting in:
a metallic oxide of the following formula (II):

$$M_xO_y \quad \text{(II)}$$

wherein:
M is a metal selected from the group constituted of Fe and Mn, M representing in particular Fe,
x and y are positive integers such as y=(x·v)/2, wherein v is the average oxidation state of M in $M_xO_y$,
said metallic oxide of formula (II) being in particular Fe$_3$O$_4$, Fe$_{3-\delta}$O$_4$ with δ being such as 0<δ<1/3, or γFe$_2$O$_3$;
a metallic oxide of the following formula (III):

$$Fe_{3-y}M'_yO_4 \quad \text{(III)}$$

wherein M' is a metal selected from the group constituted of Zn, Co, Mn, Ni and Mg, y being such as 0<y≤1,
said metallic oxide of formula (III) being in particular M'Fe$_2$O$_4$,
or
a core-shell metallic oxide nanoparticle,
said core being selected from the group constituted of:
a metallic oxide of the following formula (II):

$$M_xO_y \quad \text{(II)}$$

wherein:
M is a metal selected from the group constituted of Fe, Mn.
x and y are positive integers such as y=(x·v)/2, wherein v is the average oxidation state of M in $M_xO_y$,
said metallic oxide of formula (II) being in particular Fe$_3$O$_4$, Fe$_{3-\delta}$O$_4$ with δ being such as 0<δ<1/3, γFe$_2$O$_3$, FeO, MnO,
a metallic oxide of the following formula (III):

$$Fe_{3-y}M'_yO_4 \quad \text{(III)}$$

wherein M' is a metal selected from the group constituted of Zn, Co, Mn, Ni and Mg, y being such as 0<y≤1, said metallic oxide of formula (III) being in particular M'Fe$_2$O$_4$,
said shell being selected from the group constituted of:
a metallic oxide of the following formula (II):

$$M_xO_y \quad \text{(II)}$$

wherein:
M is a metal selected from the group constituted of Fe and Mn.
x and y are positive integers such as y=(x·v)/2, wherein v is the average oxidation state of M in $M_xO_y$,
said metallic oxide of formula (II) being in particular Fe$_3$O$_4$, Fe$_{3-\delta}$O$_4$ with δ being such as 0<δ<1/3, γFe$_2$O$_3$, MnO,
a metallic oxide of the following formula (III):

$$Fe_{3-y}M'_yO_4 \quad \text{(III)}$$

wherein M' is a metal selected from the group constituted of Zn, Co, Mn, Ni and Mg, y being such as 0<y≤1, said metallic oxide of formula (III) being in particular M'Fe$_2$O$_4$,
Au,
provided that:
said core and said shell are not the same metallic oxide.

The invention also relates to a non spherical and homogenous functionalized metallic oxide nanoparticle.

In an advantageous embodiment, the present invention relates to the functionalized metallic oxide nanoparticle described above, said nanoparticle being cubic, rodshaped, octopod-shaped or nanoplatelet-shaped, said metallic oxide nanoparticle being a homogenous metallic oxide nanoparticle selected from the group consisting in:
a metallic oxide of the following formula (II):

$$M_xO_y \quad \text{(II)}$$

wherein:
M is a metal selected from the group constituted of Fe and Mn, M representing in particular Fe,
x and y are positive integers such as y=(x·v)/2, wherein v is the average oxidation state of M in $M_xO_y$,
said metallic oxide of formula (II) being in particular Fe$_3$O$_4$, Fe$_{3-\delta}$O$_4$ with δ being such as 0<δ<1/3, or γFe$_2$O$_3$;
a metallic oxide of the following formula (III):

$$Fe_{3-y}M'_yO_4 \quad \text{(III)}$$

wherein M' is a metal selected from the group constituted of Zn, Co, Mn, Ni and Mg, y being such as 0<y≤1,
said metallic oxide of formula (III) being in particular M'Fe$_2$O$_4$.

The invention also relates to a non spherical and homogenous functionalized iron oxide nanoparticle.

In an advantageous embodiment, the present invention relates to the functionalized metallic oxide nanoparticle described above, said nanoparticle being cubic, rodshaped, octopod-shaped or nanoplatelet-shaped, said metallic oxide nanoparticle being a homogenous metallic oxide nanoparticle selected from the group consisting in:
a metallic oxide of the following formula (II):

$$FeO_xO_y \quad \text{(II)}$$

wherein:
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with δ being such as 0<δ<1/3, or $\gamma Fe_2O_3$;
a metallic oxide of the following formula (III):

$$Fe_{3-y}M'_yO_4 \quad (III)$$

wherein M' is a metal selected from the group constituted of Zn, Co, Mn, Ni and Mg, y being such as 0<y≤1,
said metallic oxide of formula (III) being in particular $M'Fe_2O_4$.

The invention also relates to a non spherical and homogenous functionalized Mn oxide nanoparticle.

In an advantageous embodiment, the present invention relates to the functionalized metallic oxide nanoparticle described above, said nanoparticle being cubic, rodshaped, octopod-shaped or nanoplatelet-shaped,
said metallic oxide nanoparticle being a homogenous metallic oxide nanoparticle selected from the group consisting in:
a metallic oxide of the following formula (II):

$$MnO_xO_y \quad (II)$$

wherein:
x and y are positive integers such as y=(x·v)/2, wherein v is the average oxidation state of M in $M_xO_y$,
a metallic oxide of the following formula (III):

$$Fe_{3-y}Mn_yO_4 \quad (III)$$

y being such as 0<y≤1,
said metallic oxide of formula (III) being in particular $MnFe_2O_4$.

The invention also relates to a spherical functionalized metallic oxide nanoparticle.

In an advantageous embodiment, the present invention relates to the functionalized metallic oxide nanoparticle described above, said nanoparticle being substantially spherical, said metallic oxide nanoparticle being:
a homogenous metallic oxide nanoparticle selected from the group consisting in:
a metallic oxide of the following formula (II):

$$M_xO_y \quad (II)$$

wherein:
M is a metal selected from the group constituted of Fe and Mn, M representing in particular Fe,
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with δ being such as 0<δ<1/3, or $\gamma Fe_2O_3$;
a metallic oxide of the following formula (III):

$$Fe_{3-y}M'_yO_4 \quad (III)$$

wherein M' is a metal selected from the group constituted of Zn, Co, Mn, Ni and Mg, y being such as 0<y≤1,
said metallic oxide of formula (III) being in particular $M'Fe_2O_4$,
or
a core-shell metallic oxide nanoparticle,
said core being selected from the group constituted of:
a metallic oxide of the following formula (II):

$$M_xO_y \quad (II)$$

wherein:
M is a metal selected from the group constituted of Fe, Mn.

x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with δ being such as 0<δ<1/3, $\gamma Fe_2O_3$, FeO, MnO,
a metallic oxide of the following formula (III):

$$Fe_{3-y}M'_yO_4 \quad (III)$$

wherein M' is a metal selected from the group constituted of Zn, Co, Mn, Ni and Mg, y being such as 0<y≤1, said metallic oxide of formula (III) being in particular $M'Fe_2O_4$,
said shell being selected from the group constituted of:
a metallic oxide of the following formula (II):

$$M_xO_y \quad (II)$$

wherein:
M is a metal selected from the group constituted of Fe and Mn.
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with δ being such as 0<δ<1/3, $\gamma Fe_2O_3$, MnO,
a metallic oxide of the following formula (III):

$$Fe_{3-y}M'_yO_4 \quad (III)$$

wherein M' is a metal selected from the group constituted of Zn, Co, Mn, Ni and Mg, y being such as 0<y≤1, said metallic oxide of formula (III) being in particular $M'Fe_2O_4$,
Au,
provided that:
said core and said shell are not the same metallic oxide.

The invention also relates to a spherical core-shell functionalized metallic oxide nanoparticle.

In an advantageous embodiment, the present invention relates to the functionalized metallic oxide nanoparticle described above, said nanoparticle being substantially spherical, said metallic oxide nanoparticle being:
a core-shell metallic oxide nanoparticle,
said core being selected from the group constituted of:
a metallic oxide of the following formula (II):

$$M_xO_y \quad (II)$$

wherein:
M is a metal selected from the group constituted of Fe, Mn.
x and y are positive integers such as y=(x·v)/2, wherein v is the average oxidation state of M in $M_xO_y$,
said metallic oxide of formula (II) being in particular $Fe_3O_4$, $Fe_{3-\delta}O_4$ with δ being such as 0<δ<1/3, $\gamma Fe_2O_3$, FeO, MnO,
a metallic oxide of the following formula (III):

$$Fe_{3-y}M'_yO_4 \quad (III)$$

wherein M' is a metal selected from the group constituted of Zn, Co, Mn, Ni and Mg, y being such as 0<y≤1, said metallic oxide of formula (III) being in particular $M'Fe_2O_4$,
said shell being selected from the group constituted of:
a metallic oxide of the following formula (II):

$$M_xO_y \quad (II)$$

wherein:
M is a metal selected from the group constituted of Fe and Mn.

x and y are positive integers such as $y=(x \cdot v)/2$, wherein v is the average oxidation state of M in $M_xO_y$, said metallic oxide of formula (II) being in particular $Fe_3O_4$, $Fe_{3-\delta}O_4$ with δ being such as $0<\delta<1/3$, $\gamma Fe_2O_3$, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as $0<y\leq1$, said metallic oxide of formula (III) being in particular $M'Fe_2O_4$, Au, provided that:

said core and said shell are not the same metallic oxide.

The invention also relates to a spherical core-shell functionalized iron oxide nanoparticle.

In an advantageous embodiment, the present invention relates to the functionalized metallic oxide nanoparticle described above, said nanoparticle being substantially spherical, said metallic oxide nanoparticle being:

a core-shell metallic oxide nanoparticle, said core being selected from the group constituted of:

a metallic oxide of the following formula (II):

$$M_xO_y \tag{II}$$

wherein:

M is a metal selected from the group constituted of Fe, Mn.

x and y are positive integers such as $y=(x \cdot v)/2$, wherein v is the average oxidation state of M in $M_xO_y$, said metallic oxide of formula (II) being in particular $Fe_3O_4$, $Fe_{3-\delta}O_4$ with δ being such as $0<\delta<1/3$, $\gamma Fe_2O_3$, FeO, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as $0<y\leq1$, said metallic oxide of formula (III) being in particular $M'Fe_2O_4$, said shell being selected from the group constituted of:

a metallic oxide of the following formula (II):

$$M_xO_y \tag{II}$$

wherein:

M is a metal selected from the group constituted of Fe and Mn.

x and y are positive integers such as $y=(x \cdot v)/2$, wherein v is the average oxidation state of M in $M_xO_y$, said metallic oxide of formula (II) being in particular $Fe_3O_4$, $Fe_{3-\delta}O_4$ with δ being such as $0<\delta<1/3$, $\gamma Fe_2O_3$, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as $0<y\leq1$, said metallic oxide of formula (III) being in particular $M'Fe_2O_4$, Au, provided that:

said core and said shell are not the same metallic oxide, said core being of formula (II) wherein M is Fe or of formula (III), or said shell being of formula (II) wherein M is Fe or of formula (III).

In an advantageous embodiment, the present invention relates to the functionalized metallic oxide nanoparticle described above, said metallic oxide nanoparticle being:

a core-shell metallic oxide nanoparticle, said core being selected from the group constituted of:

a metallic oxide of the following formula (II):

$$M_xO_y \tag{II}$$

wherein:

M is a metal selected from the group constituted of Fe, Mn.

x and y are positive integers such as $y=(x \cdot v)/2$, wherein v is the average oxidation state of M in $M_xO_y$, said metallic oxide of formula (II) being in particular $Fe_3O_4$, $Fe_{3-\delta}O_4$ with δ being such as $0<\delta<1/3$, $\gamma Fe_2O_3$, FeO, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as $0<y\leq1$, said metallic oxide of formula (III) being in particular $M'Fe_2O_4$, said shell being selected from the group constituted of:

a metallic oxide of the following formula (II):

$$M_xO_y \tag{II}$$

wherein:

M is a metal selected from the group constituted of Fe and Mn.

x and y are positive integers such as $y=(x \cdot v)/2$, wherein v is the average oxidation state of M in $M_xO_y$, said metallic oxide of formula (II) being in particular $Fe_3O_4$, $Fe_{3-\delta}O_4$ with δ being such as $0<\delta<1/3$, $\gamma Fe_2O_3$, MnO, a metallic oxide of the following formula (III):

$$Fe_{3-y}M'_yO_4 \tag{III}$$

wherein M' is a metal selected from the group constituted of Zn, Co, Mn, Ni and Mg, y being such as $0<y\leq1$, said metallic oxide of formula (III) being in particular $M'Fe_2O_4$, said core being of formula MnO (II) and said shell of formula (II) with M=Fe, in particular $Fe_3O_4$, or of formula (III), in particular $Fe_2MO_4$, or said core being of formula (II) with M=Fe, in particular $Fe_3O_4$, or of formula (III), in particular $Fe_2MO_4$, and said shell being of formula MnO (II).

Such a nanoparticle is a T1 and T2 MRI contrast agent.

T1 and T2 MRI contrast agent properties can be assessed by making ghost images or by in vivo experiments.

Such a nanoparticle has also a sufficient heating power for a magnetic hyperthermia treatment.

In an advantageous embodiment, the present invention relates to the functionalized metallic oxide nanoparticle described above, said nanoparticle being functionalized with at least two compounds of formula (I) wherein j=1, X and Y represent a group of formula $-L_p-E_p-R$, corresponding to the formula (I-0):

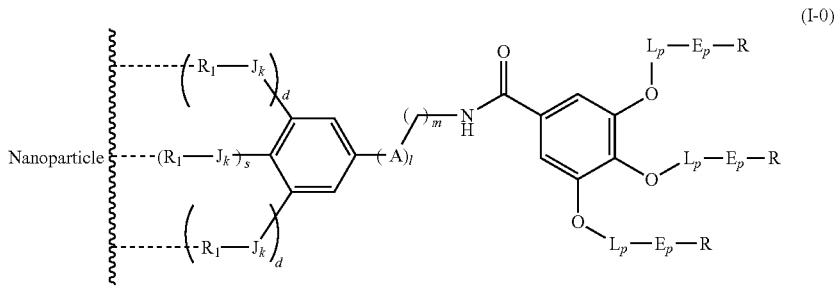

wherein $R_1$, J, k, A, l, m, s, d, L, p, E and R are as described above.

In an advantageous embodiment, the present invention relates to the functionalized metallic oxide nanoparticle described above, said nanoparticle being functionalized with at least two compounds of formula (I) wherein j=0 and Y represent a group of formula $-L_p-E_p-R$, corresponding to the formula (I-0bis):

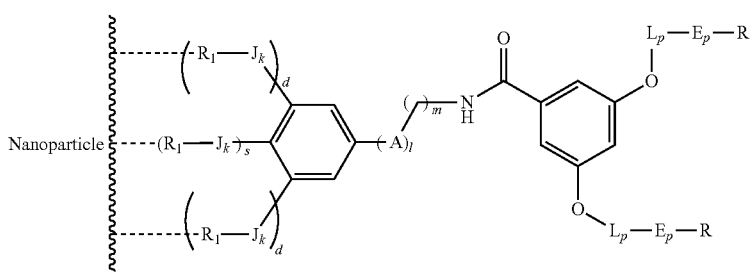

wherein $R_1$, J, k, A, l, m, s, d, L, p, E and R are as described above.

In an advantageous embodiment, the present invention relates to the functionalized metallic oxide nanoparticle described above, said nanoparticle being functionalized with at least two compounds of formula (I) wherein j=1, X and Y represent a group of formula $-L_p-E_p-R$, corresponding to the formula (I-0):

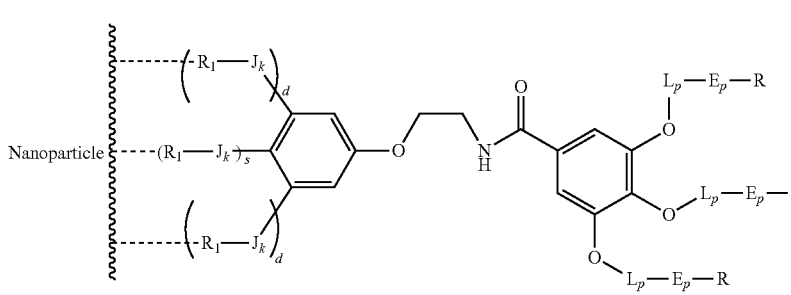

wherein $R_1$, J, k, s, d, L, p, E and R are as described above, p being in particular equal to 1;

L being in particular a PEG chain of the following formula (2):

wherein q is an integer comprised from 1 to 10,

E representing in particular a group selected from —O—, —NH—, and —COO—, more particularly —COO— or —O—;

R representing in particular H.

In an advantageous embodiment, the present invention relates to the functionalized metallic oxide nanoparticle described above, said nanoparticle being functionalized with at least two compounds of formula (I) wherein j=0 and Y represent a group of formula $-L_p-E_p-R$, corresponding to the formula (I-0bis):

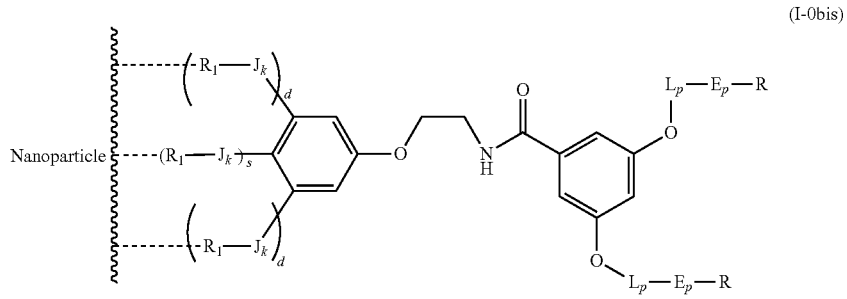

wherein $R_1$, J, k, s, d, L, p, E and R are as described above, p being in particular equal to 1;
L being in particular a PEG chain of the following formula (2):

(2)

wherein q is an integer comprised from 1 to 10,
E representing in particular a group selected from —O—, —NH—, and —COO—, more particularly —COO— or —O—;
R representing in particular H.

In an advantageous embodiment, the present invention relates to the functionalized metallic oxide nanoparticle described above, said nanoparticle being functionalized with at least two compounds of formula (I) wherein j=1, X and Y represent a group of formula -$L_p$-$E_p$-R, corresponding to the formula (I-0a):

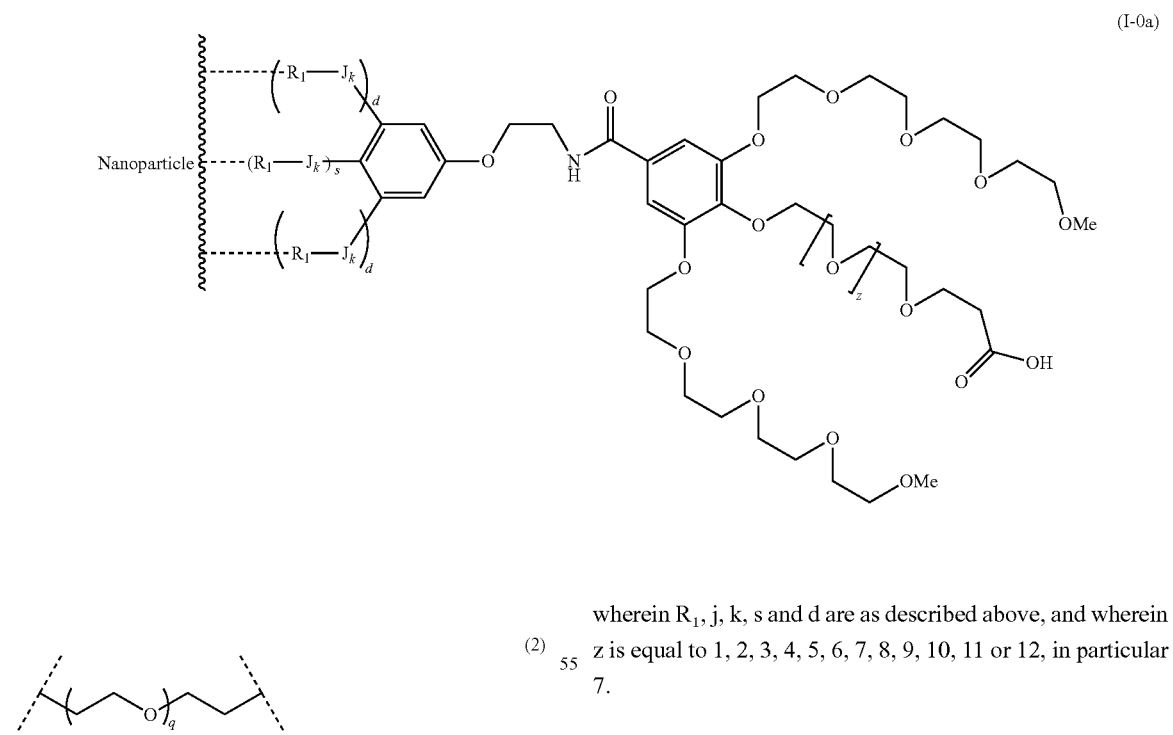

wherein $R_1$, j, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula -$L_p$-$E_p$-R, corresponding to the formula (I-0b):

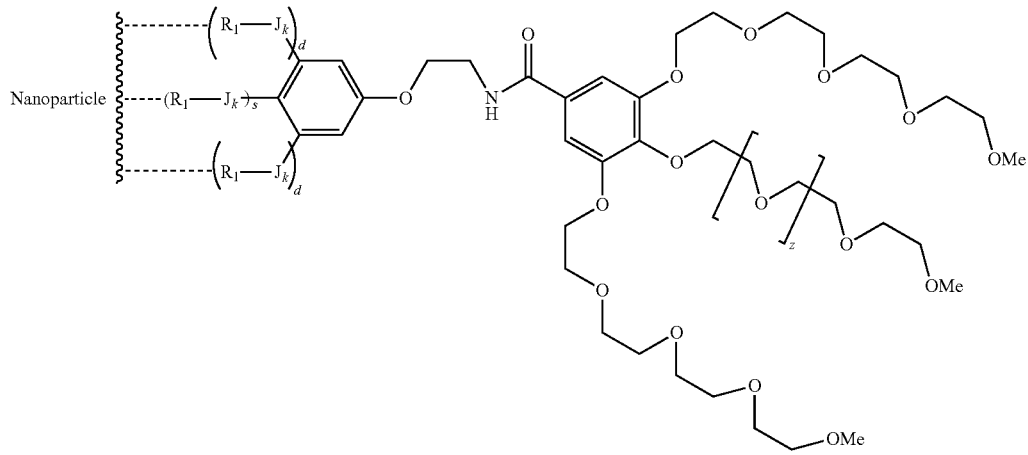

(I-0b)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula $-L_p-E_p-R$, corresponding to the formula (I-0c):

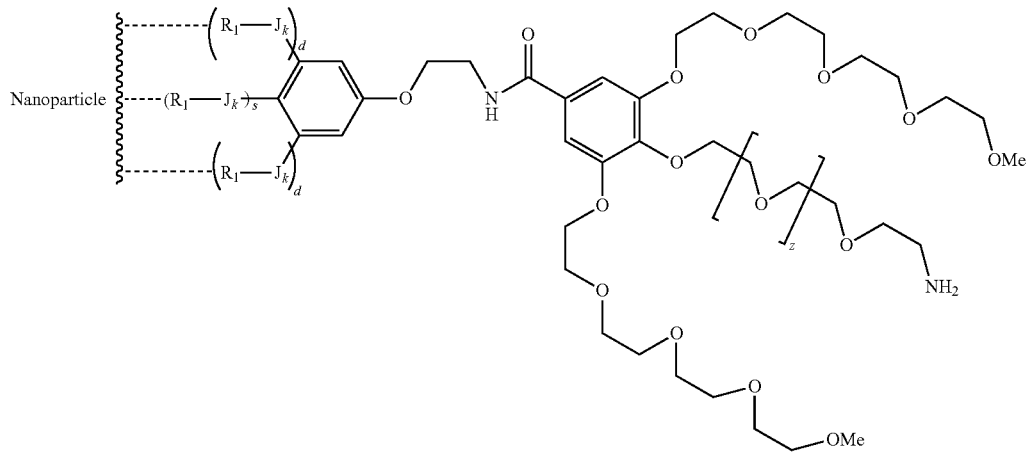

(I-0c)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula $-L_p-E_p-R$, corresponding to the formula (I-0d):

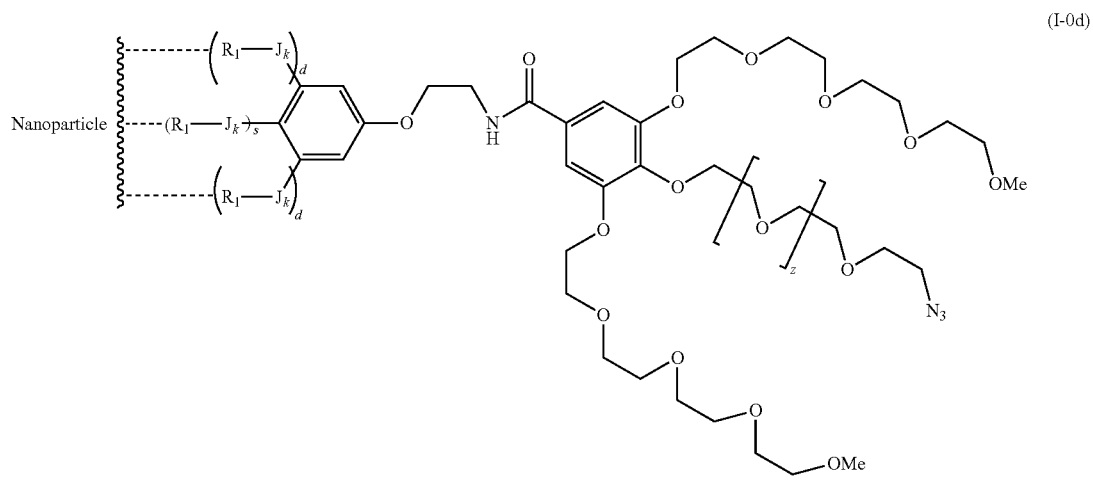

(I-0d)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula $-L_p-E_p-R$, corresponding to the formula (I-0e):

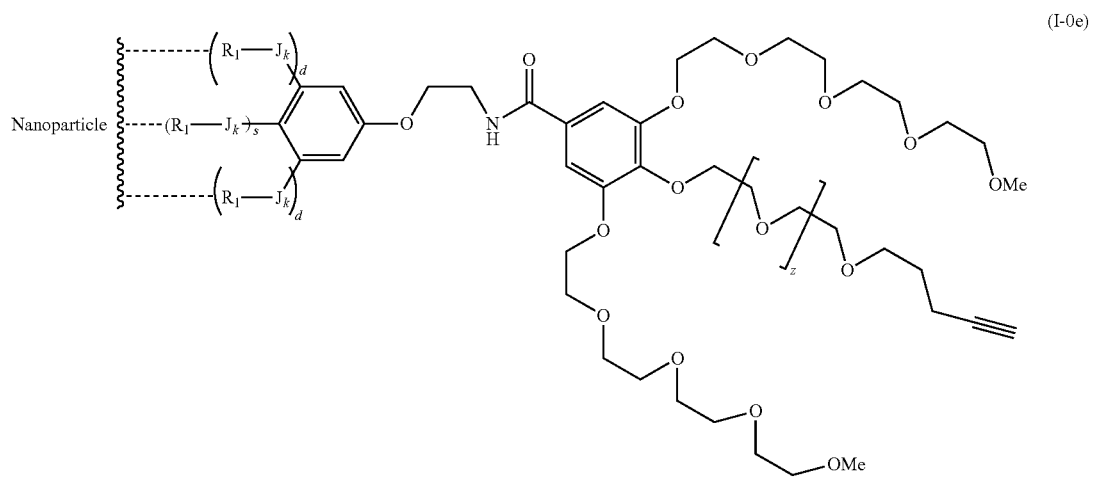

(I-0e)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula $-L_p-E_p-R$, corresponding to the formula (I-0f):

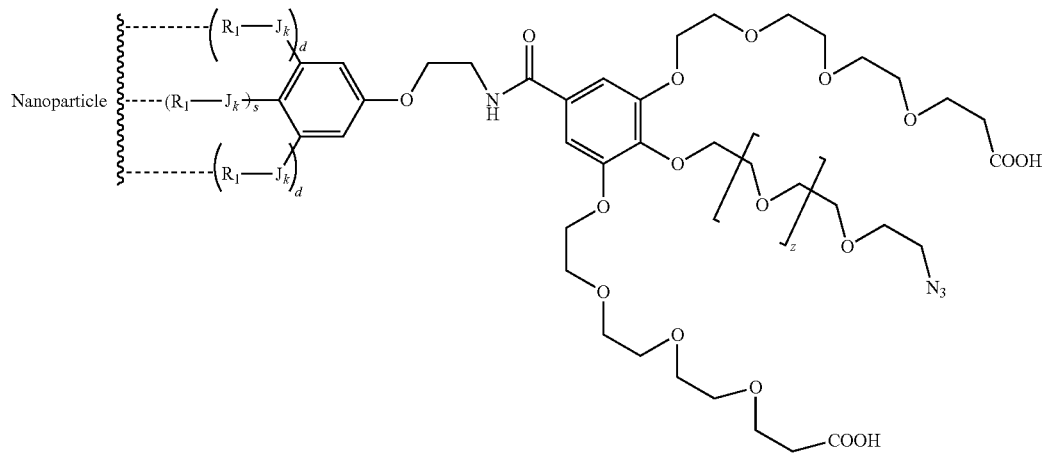

(I-0f)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula -$L_p$-$E_p$-R, corresponding to the formula (I-0g):

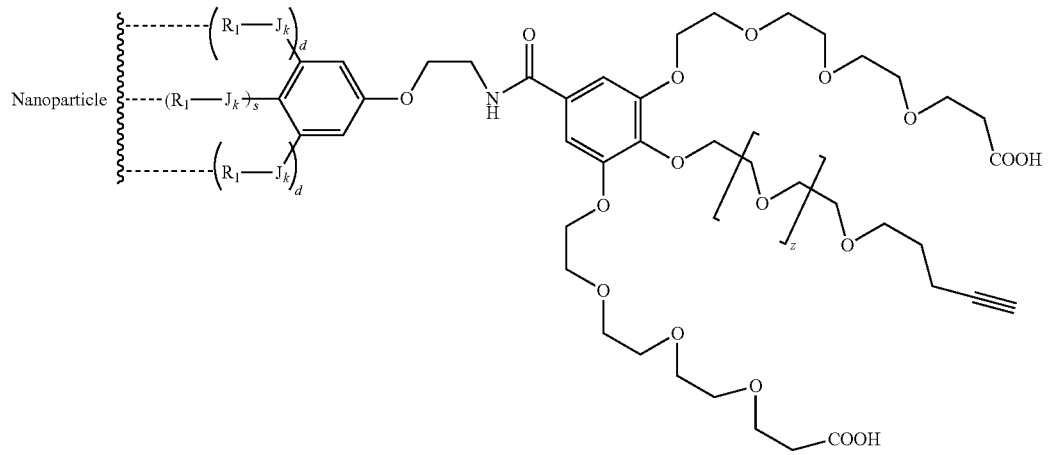

(I-0g)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula -$L_p$-$E_p$-R, corresponding to the formula (I-0h):

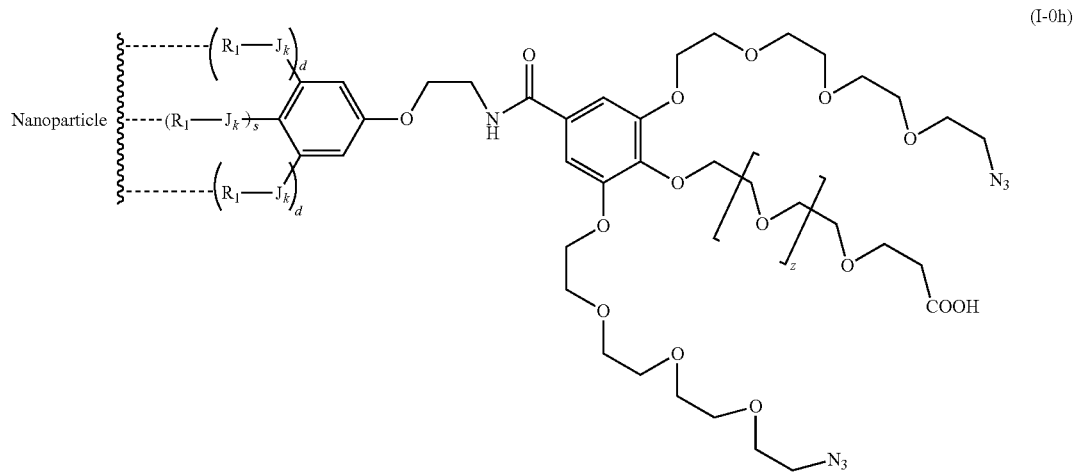

(I-0h)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula -$L_p$-$E_p$-R, corresponding to the formula (I-0i):

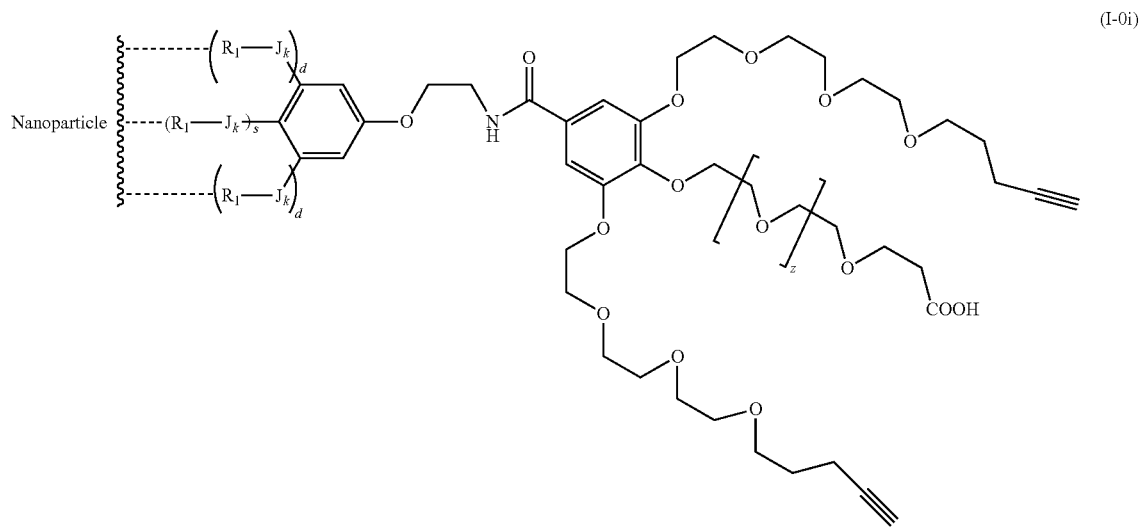

(I-0i)

wherein $R_1$, J, k, s and d are as described above, and wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I) wherein j=1, X and Y represent a group of formula -$L_p$-$E_p$-R, corresponding to the formula (I-0j):

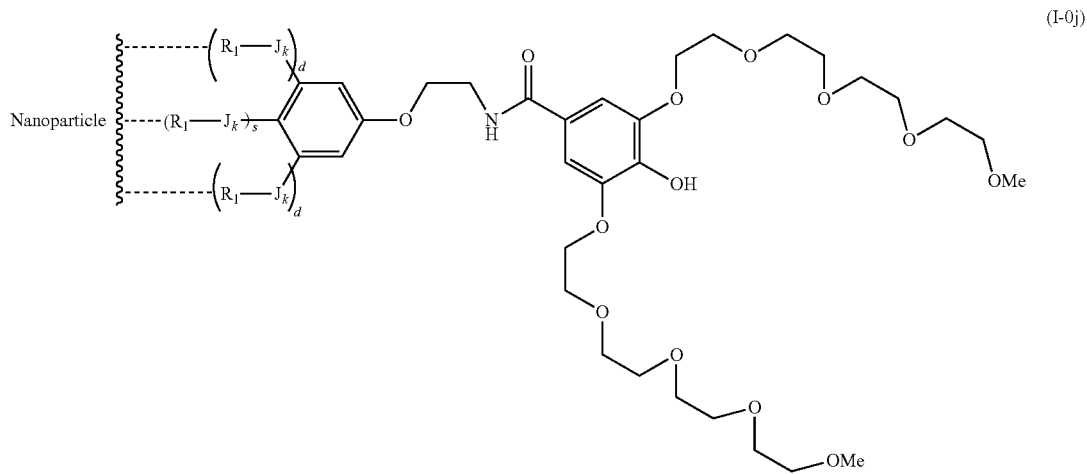

(I-0j)

wherein $R_1$, J, k, s and d are as described above.

In an advantageous embodiment, the present invention relates to the functionalized metallic oxide nanoparticle described above, said nanoparticle being functionalized with at least two compounds of formula (I) wherein j=0 and Y represent a group of formula -$L_p$-$E_p$-R, corresponding to the formula (I-0k):

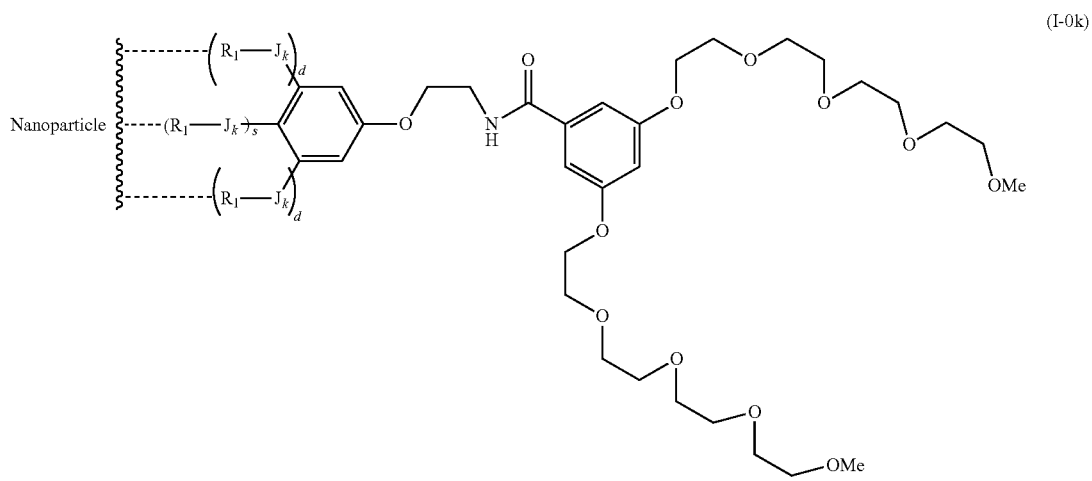

(I-0k)

wherein $R_1$, J, k, s and d are as described above.

In an advantageous embodiment, the present invention relates to the functionalized metallic oxide nanoparticle described above, said nanoparticle being functionalized with at least two compounds of formula (I), wherein Y represents a dendrimer of generation n, as described above.

In an advantageous embodiment, the present invention relates to the functionalized metallic oxide nanoparticle described above, said nanoparticle being functionalized with at least two compounds of formula (I), wherein Y represents a dendrimer of generation n, as described above, 1 being equal to 1, m being to 2, A representing —O—.

In an advantageous embodiment, the present invention relates to the functionalized metallic oxide nanoparticle described above, said nanoparticle being functionalized with at least two compounds of formula (I), wherein Y represents a dendrimer of generation 1, as described above, corresponding to the following formula (I-1):

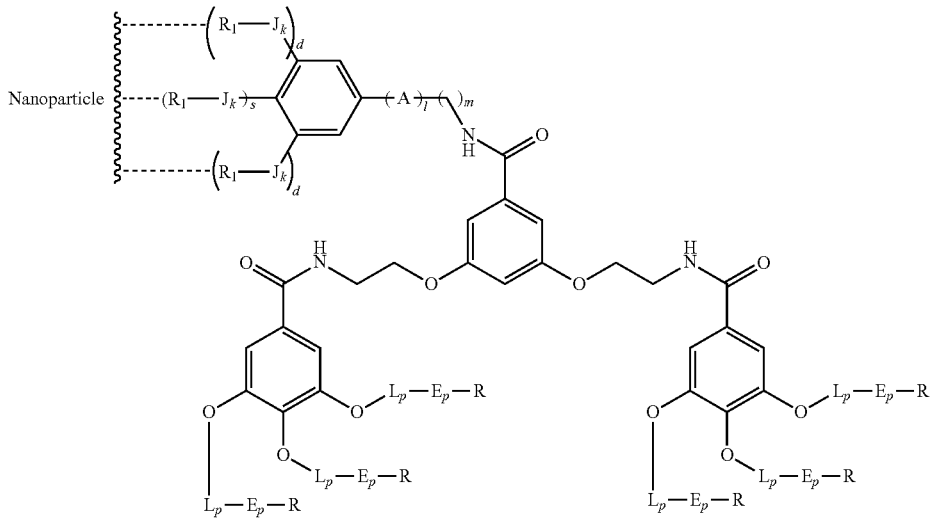

(I-1)

wherein $R_1$, J, k, A, l, m, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 1, as described above, corresponding to the following formula (I-1bis):

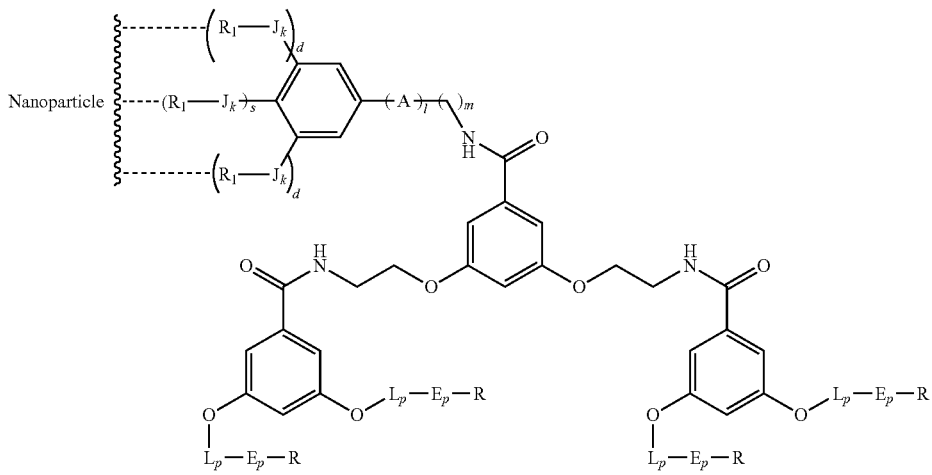

(I-1bis)

wherein $R_1$, J, k, A, l, m, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 1, as described above, l being equal 1, m being equal to 2, A representing —O—, corresponding to the following formula (I-1):

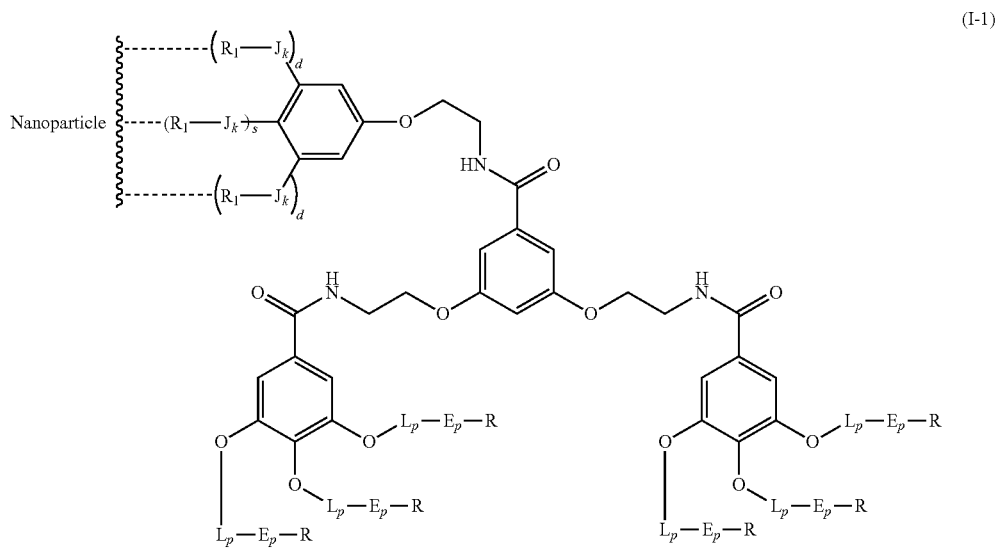

(I-1)

wherein $R_1$, J, k, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 1, as described above, 1 being equal 1, m being equal to 2, A representing —O—, corresponding to the following formula (I-1bis):

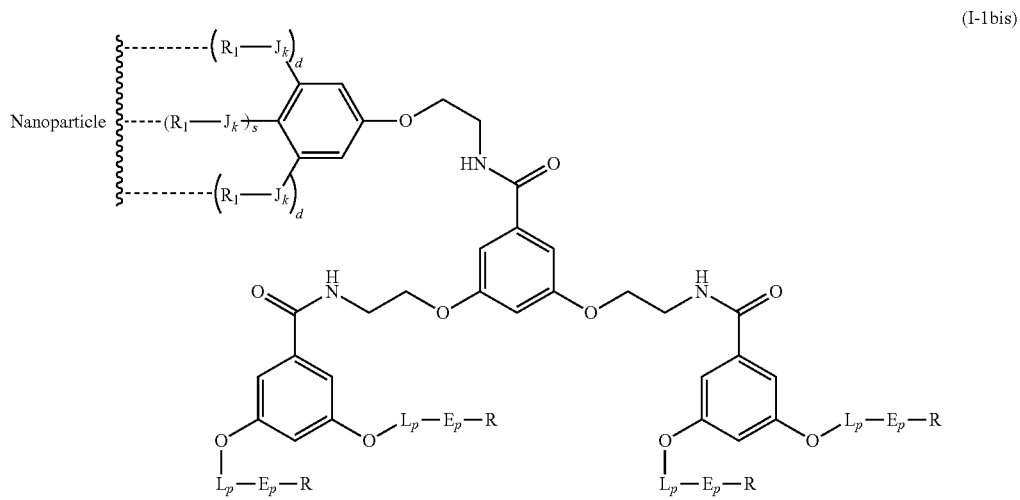

(I-1bis)

wherein $R_1$, J, k, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 2, as described above, corresponding to the following formula (I-2):

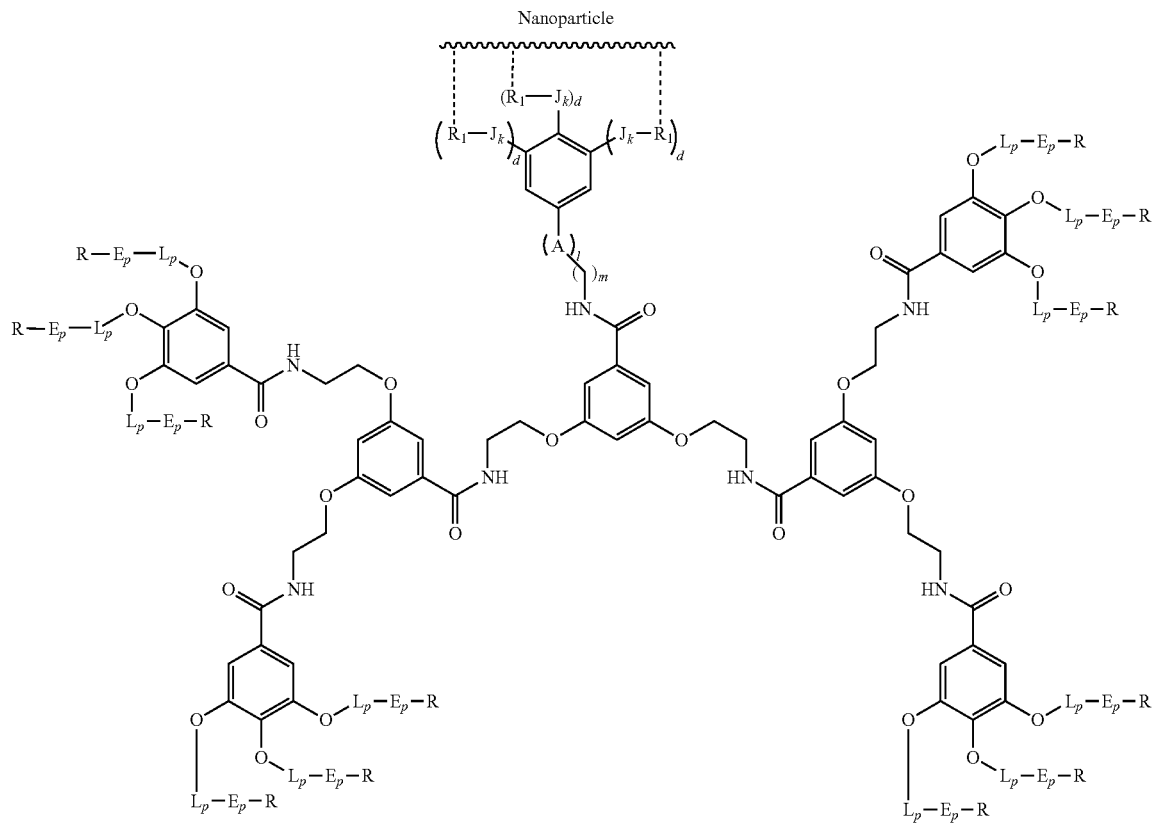

(I-2)

wherein $R_1$, J, k, A, l, m, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 2, as described above, corresponding to the following formula (I-2bis):

(1-2bis)

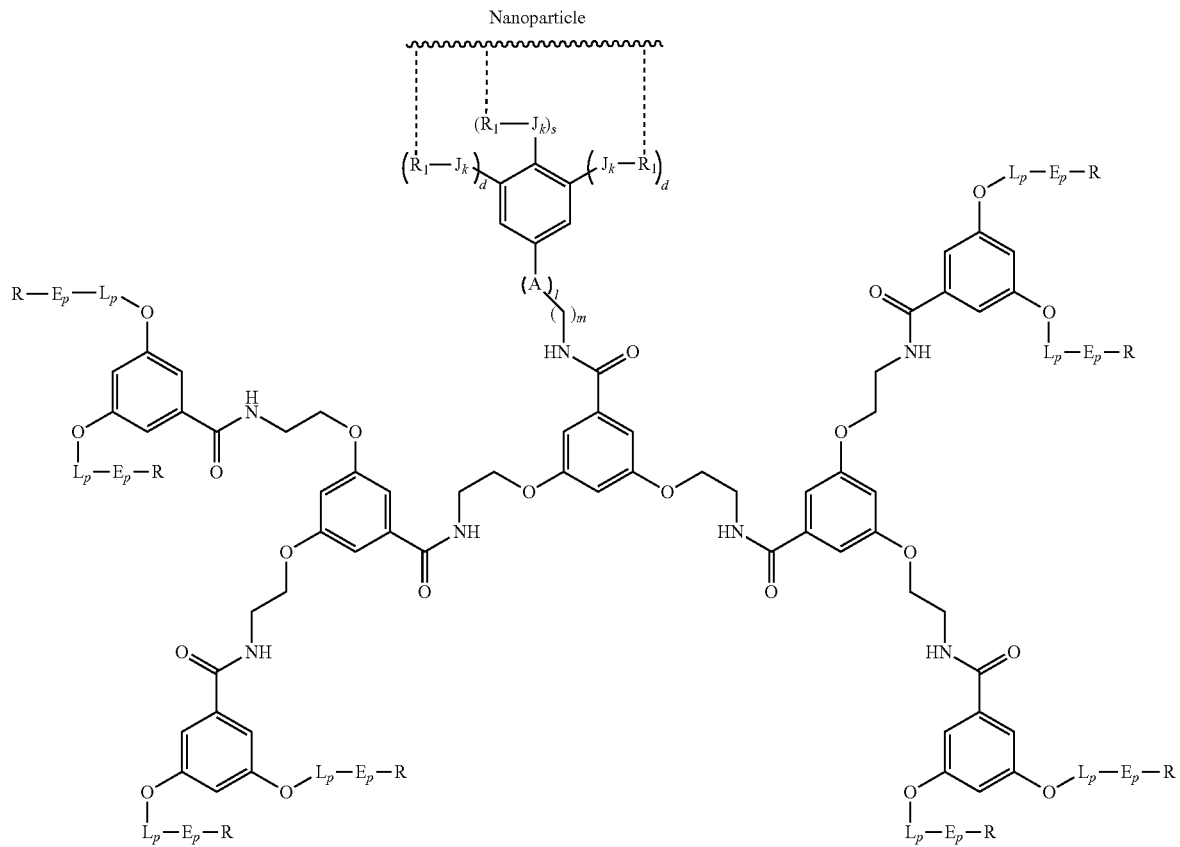

wherein $R_1$, J, k, A, l, m, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 2, as described above, l being equal 1, m being to 2, A representing —O—, corresponding to the following formula (I-2):

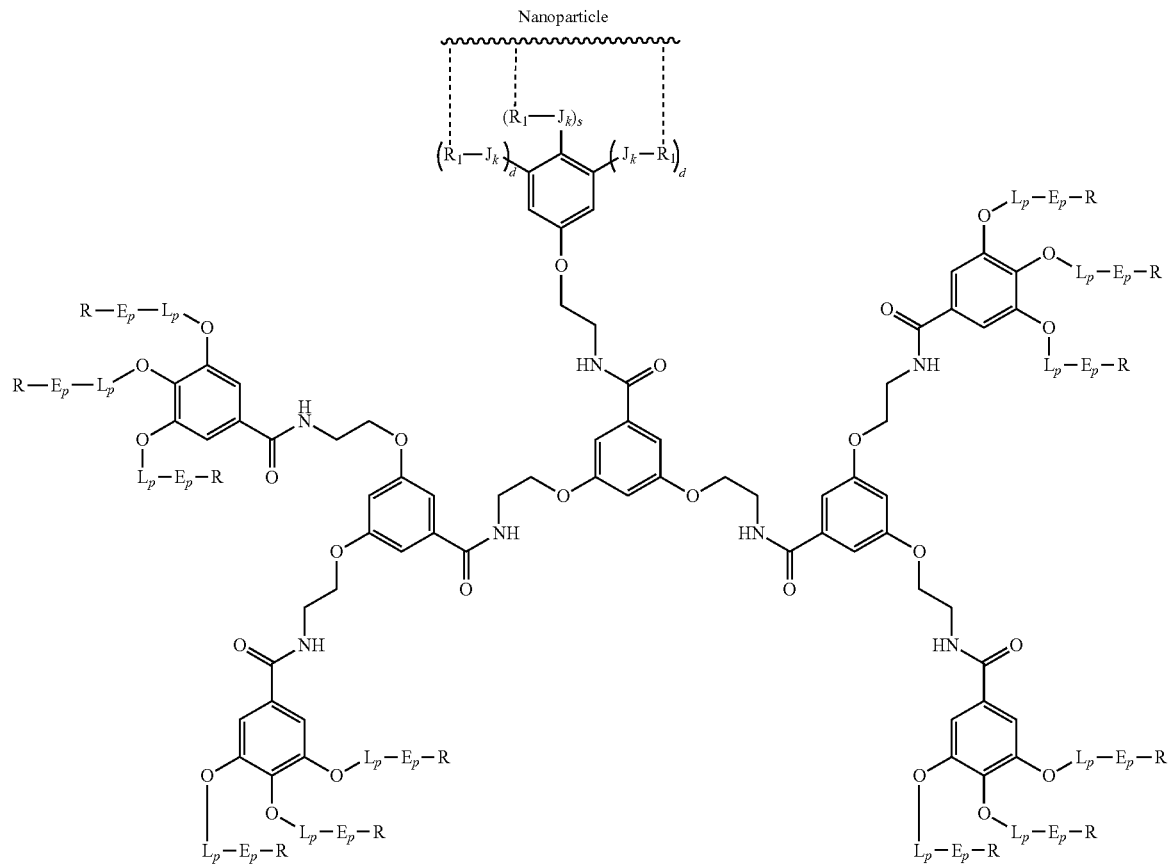

(I-2)

wherein $R_1$, J, k, s, d, L, p, E and R are as described above.

In an advantageous embodiment, the present invention relates to the functionalized metallic oxide nanoparticle described above, said nanoparticle being functionalized with at least two compounds of formula (I), wherein Y represents a dendrimer of generation 2, as described above, 1 being equal 1, m being to 2, A representing —O—, corresponding to the following formula (I-2bis):

(I-2bis)

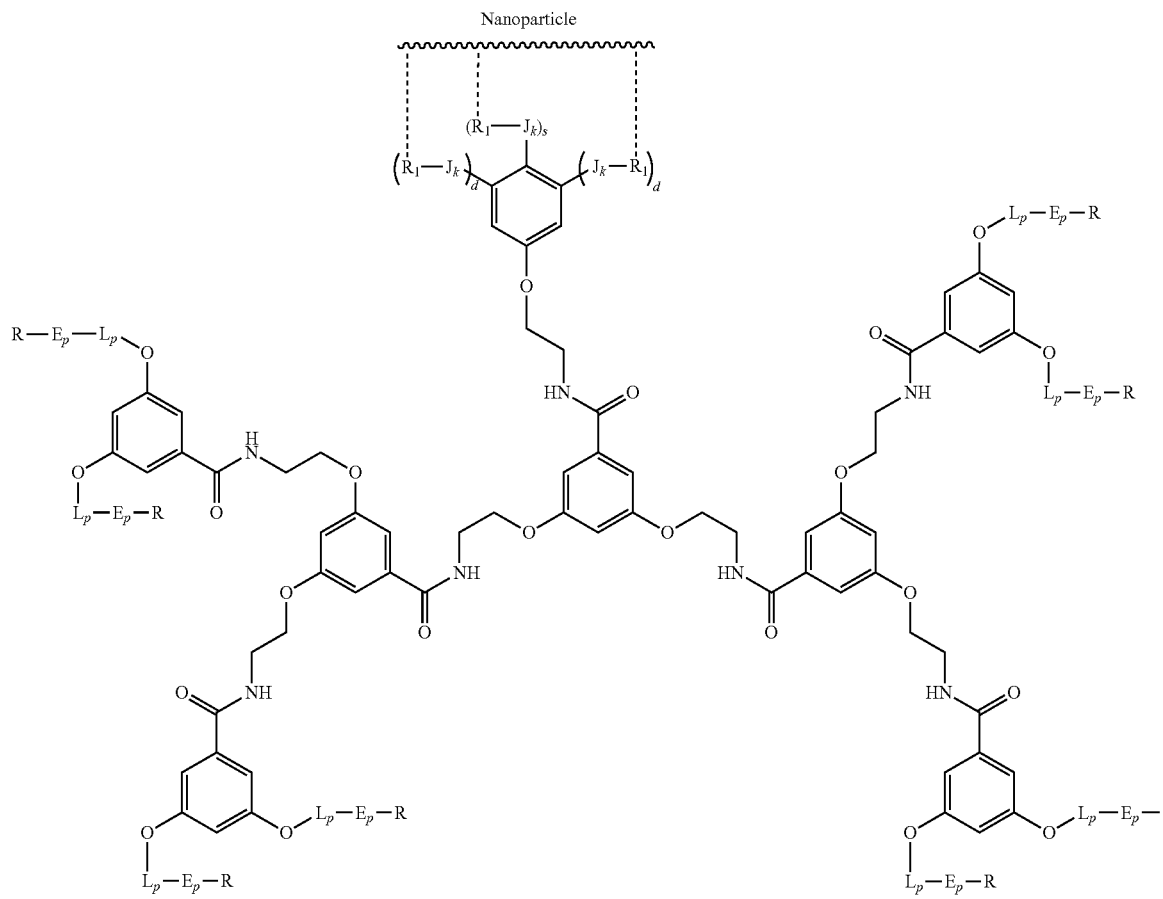

wherein $R_1$, J, k, s, d, L, p, E and R are as described above.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (I-0b), (I-0c), (I-0d), (I-0e), (I-1), (I-1bis), (I-2) or (I-2bis), wherein s is equal to 1 and d is equal to 0, said compounds of formula (I) being iono-covalently bound to said metallic oxide nanoparticle via one $R_1$ group.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (I-0b), (I-0c), (I-0d), (I-0e), (I-1), (I-1bis), (I-2) or (I-2bis), wherein s is equal to 0 and d is equal to 1, said compounds of formula (I) being iono-covalently bound to said metallic oxide nanoparticle via two $R_1$ groups.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (I-0b), (I-0c), (I-0d), (I-0e), (I-1), (I-1bis), (I-2) or (I-2bis), wherein $R_1$ represents —$CH_2PO_3H_2$ and wherein s is equal to 1 and d is equal to 0.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (I-0b), (I-0c), (I-0d), (I-0e), (I-1), (I-1bis), (I-2) or (I-2bis), wherein $R_1$ represents —$CH_2PO_3H_2$ and wherein s is equal to 0 and d is equal to 1.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (I-2) or (I-2bis), wherein $R_1$ represents —$CH_2PO_3H_2$, k is equal to 0 and wherein s is equal to 1 and d is equal to 0.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (I-0b), (I-0c), (I-0d), (I-0e), (I-1), (I-1bis), (I-2) or (I-2bis), wherein $R_1$ represents —$CH_2PO_3H_2$, k is equal to 0 and wherein s is equal to 0 and d is equal to 1.

In an advantageous embodiment, the present invention relates to the functionalized metallic oxide nanoparticle described above, said nanoparticle being functionalized with at least two compounds of formula (I), in particular of formula (I-1), (I-1bis), (1-2) or (I-2bis), wherein said chains of rank i=n are of the following formulae

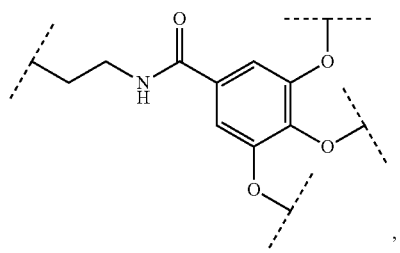
and wherein said Z groups are such as said chains of rank i=n are substituted in the following manner:
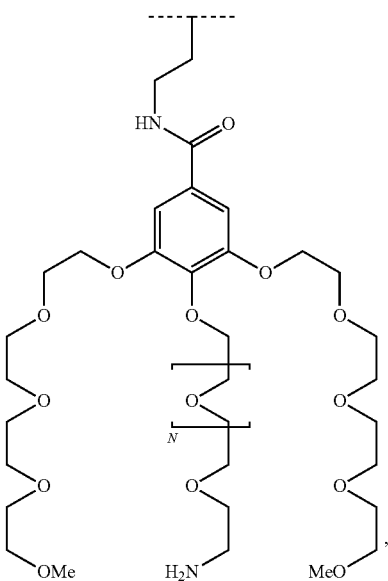
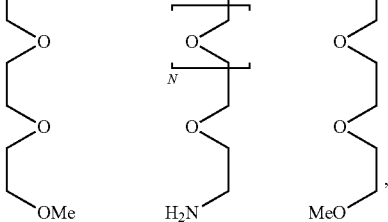

61
-continued
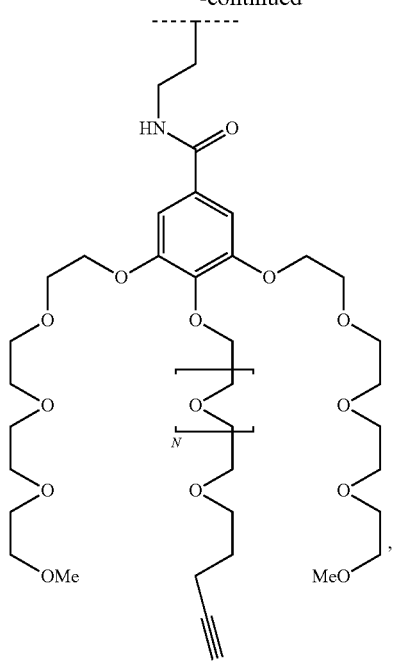
62
-continued
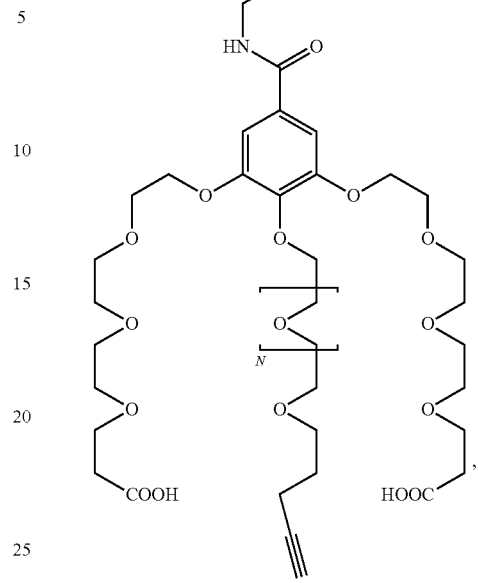
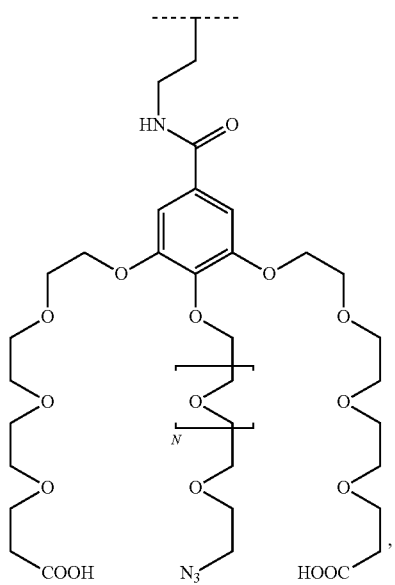
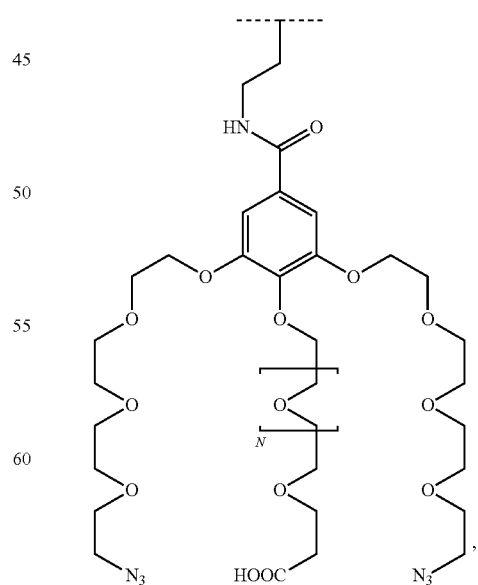

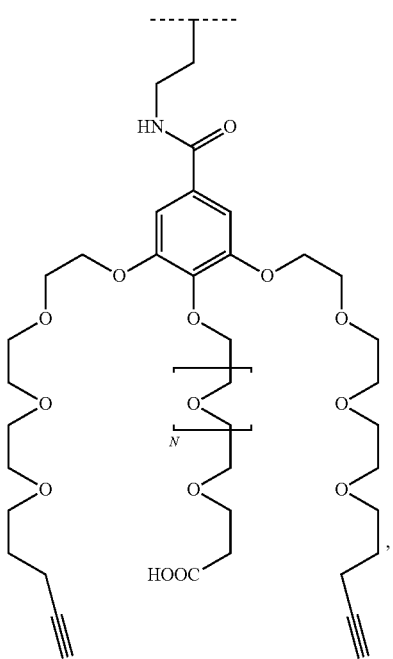

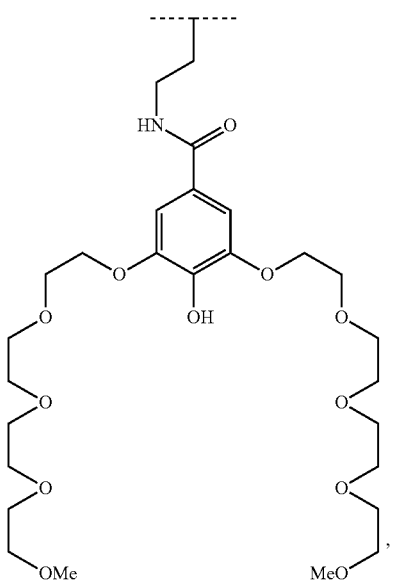

wherein z is equal to 1, 2, 3, 4, 5, 6, 7, 8, 9, 10, 11 or 12, in particular 7.

In an advantageous embodiment, the present invention relates to the functionalized metallic oxide nanoparticle described above, said nanoparticle being functionalized with at least two compounds of formula (I), in particular of formula (I-1), (I-1bis), (1-2) or (I-2bis), wherein said chains of rank i=n are of the following formulae

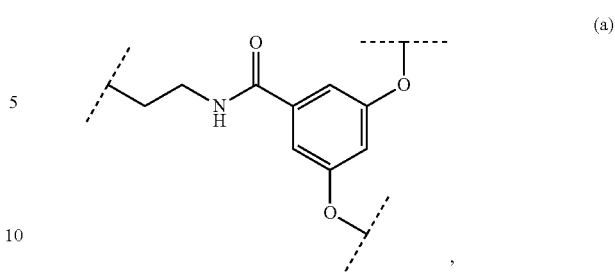

and wherein said Z groups are such as said chains of rank i=n are substituted in the following manner:

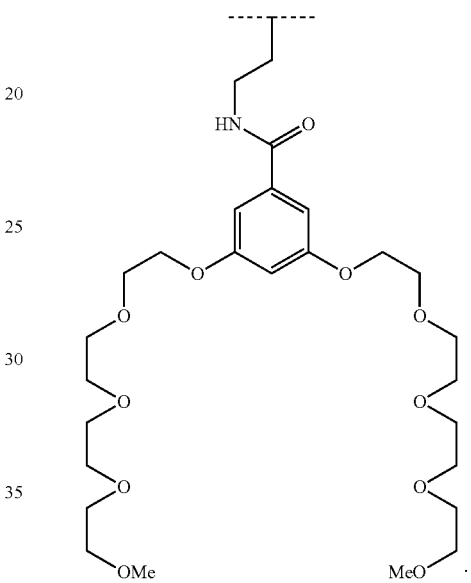

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (1-2) or (I-2bis), said metallic oxide nanoparticle being a homogenous metallic oxide nanoparticle of $Fe_3O_4$.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (1-2) or (I-2bis), said metallic oxide nanoparticle being a homogenous metallic oxide nanoparticle of $Fe_{3-\delta}O_4$ with $\delta$ being such as $0<\delta<1/3$.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (1-2) or (I-2bis), said metallic oxide nanoparticle being a homogenous metallic oxide nanoparticle of $\gamma Fe_2O_3$.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (I-2) or (I-2bis), said metallic oxide nanoparticle being of core-shell FeO@Fe$_3$O$_4$ structure.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (I-2) or (I-2bis), said metallic oxide nanoparticle being of core-shell Fe$_3$O$_4$@MnO structure.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (I-2) or (I-2bis), said metallic oxide nanoparticle being of core-shell Fe$_3$O$_4$@Au structure.

In an advantageous embodiment, the present invention relates to the functionalized metallic oxide nanoparticle described above, said nanoparticle being functionalized with at least two compounds of formula (I), in particular of formula (I-0), (I-0bis), (I-0a), (1-0), (I-0c), (I-0d), (I-0e), (I-1), (I-1bis), (I-2) or (I-2bis), said metallic oxide nanoparticle being of core-shell M'Fe$_2$O$_4$@ M"Fe$_2$O$_4$ structure, wherein M' is a metal selected from the group constituted of Zn, Co, Mn, Ni and Mg and wherein M" is a metal selected from the group constituted of Zn, Co, Mn, Ni and Mg, M' being different from M".

In an advantageous embodiment, the present invention relates to the functionalized metallic oxide nanoparticle described above, said nanoparticle being functionalized with at least two compounds of formula (I) selected from the group consisting of:

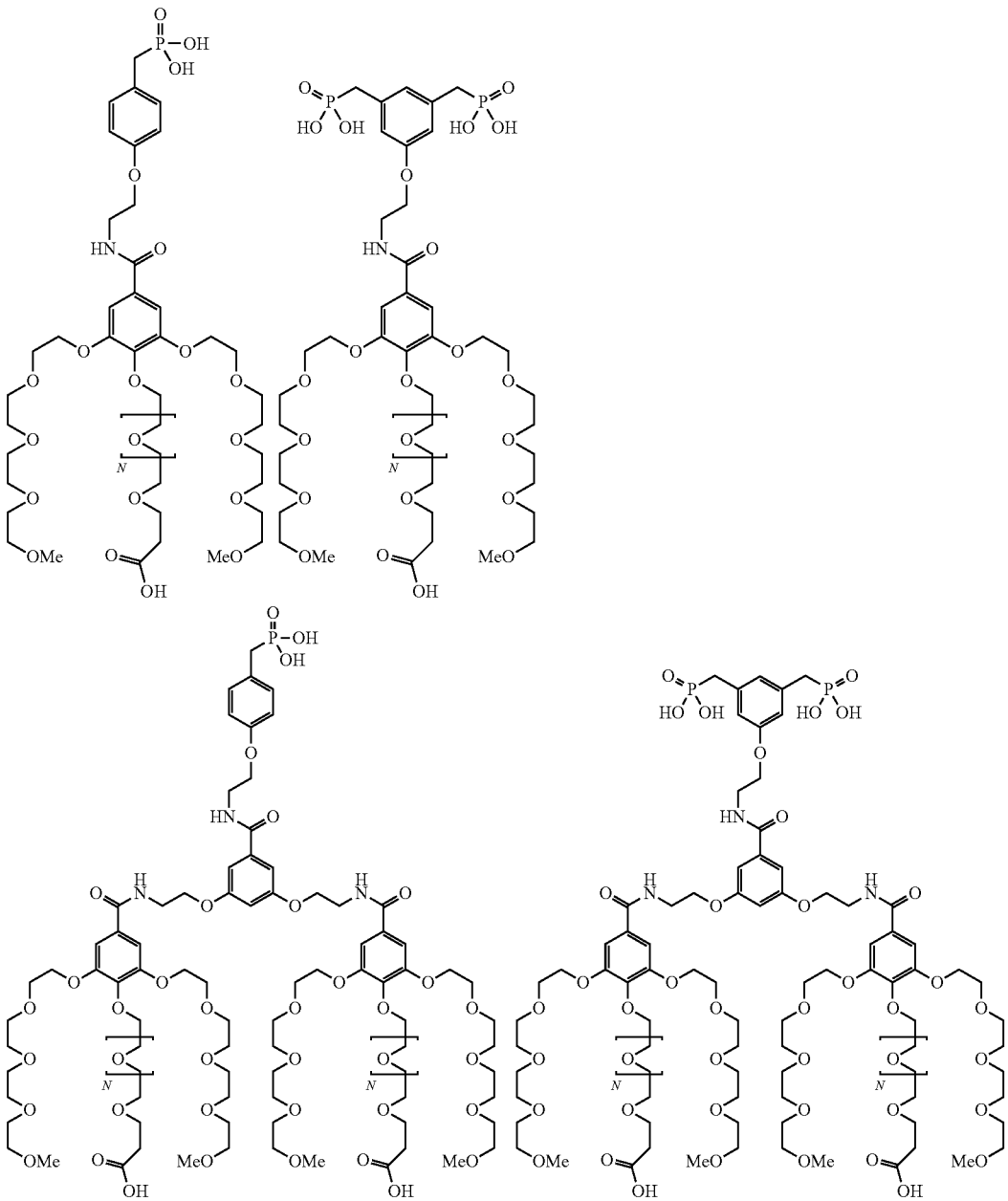

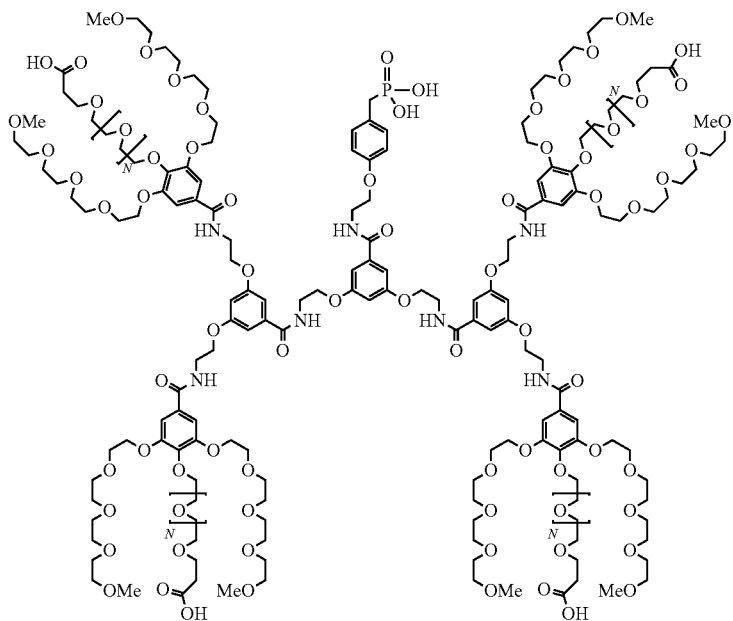
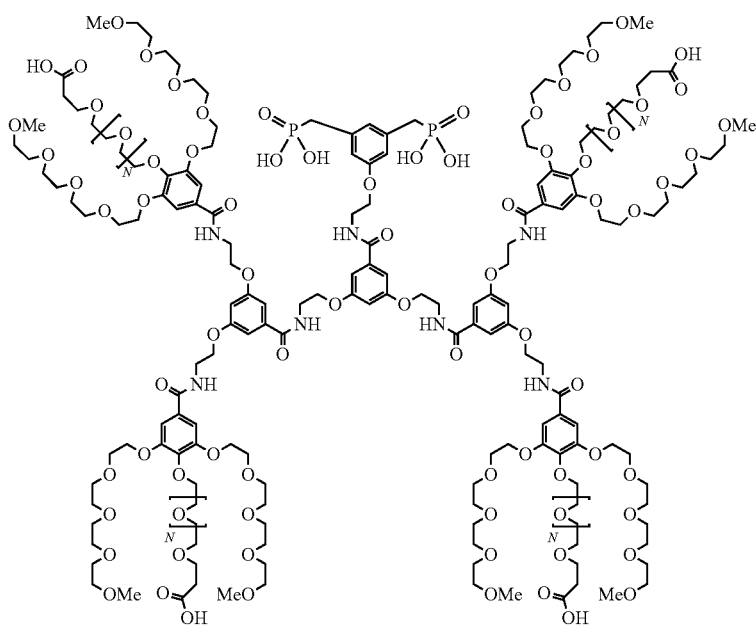

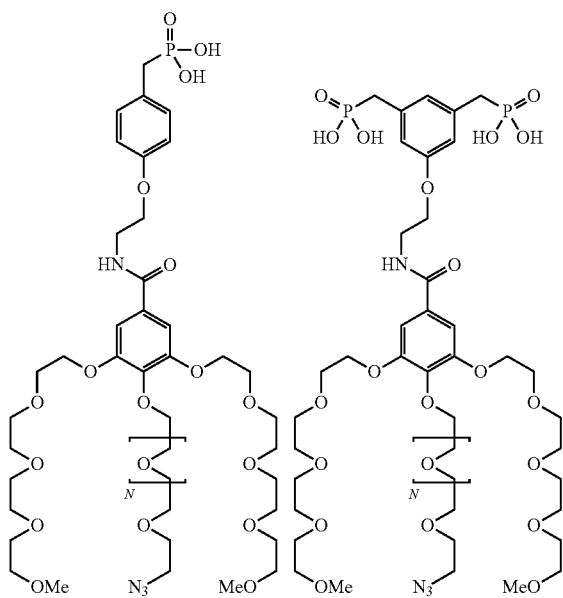
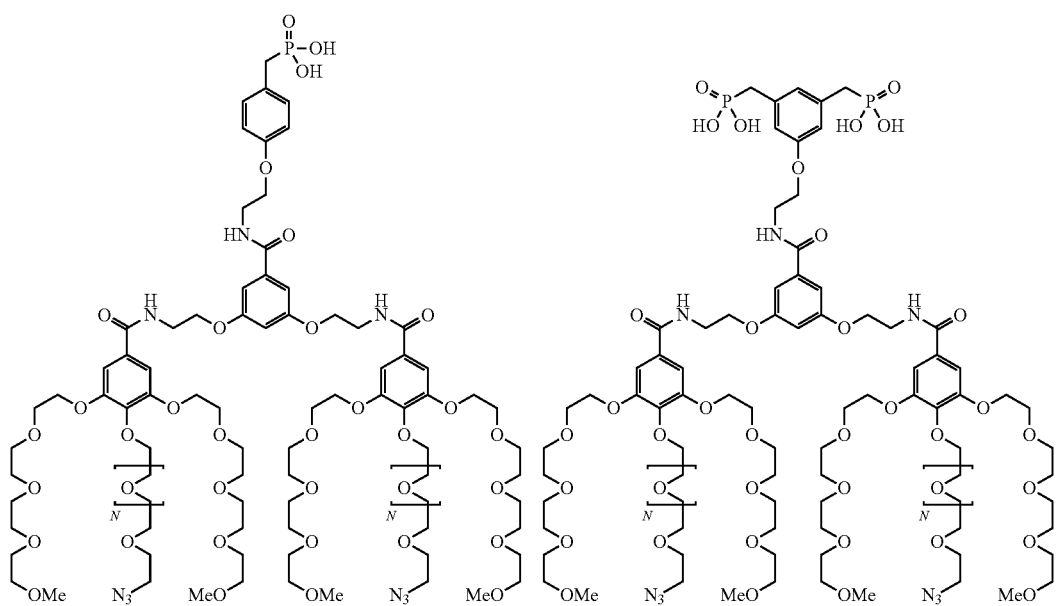

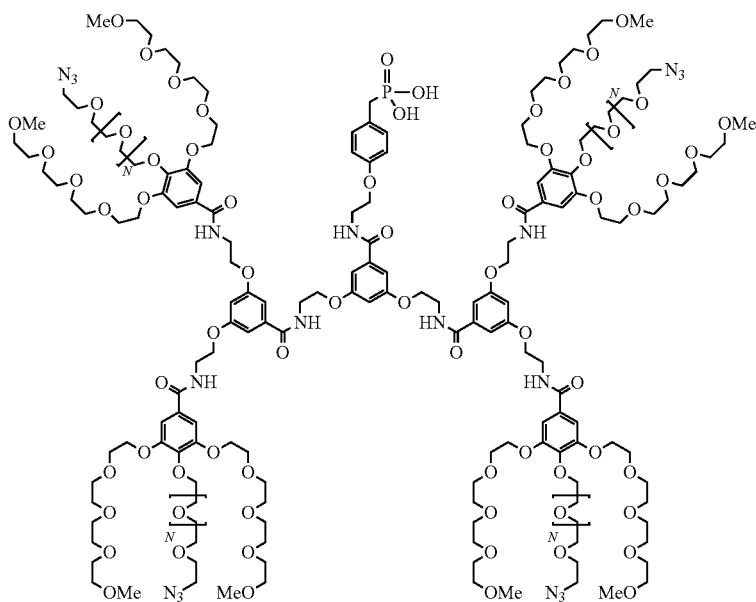
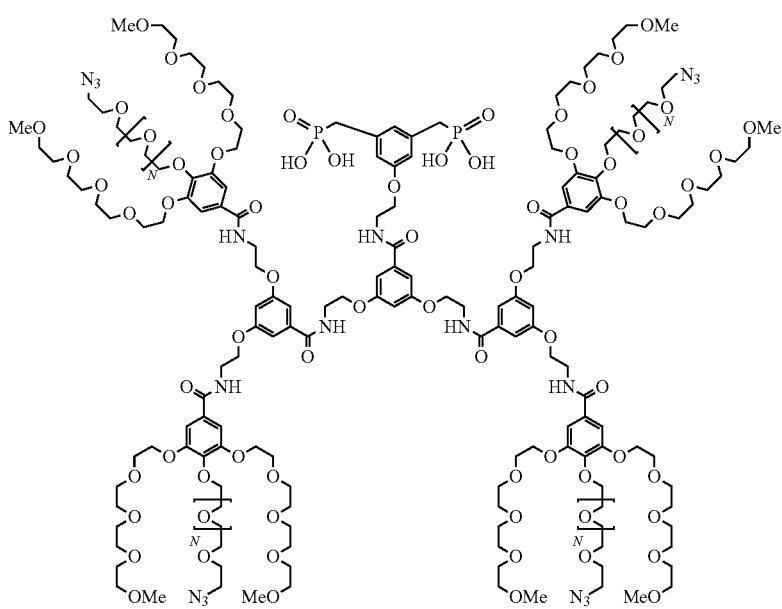

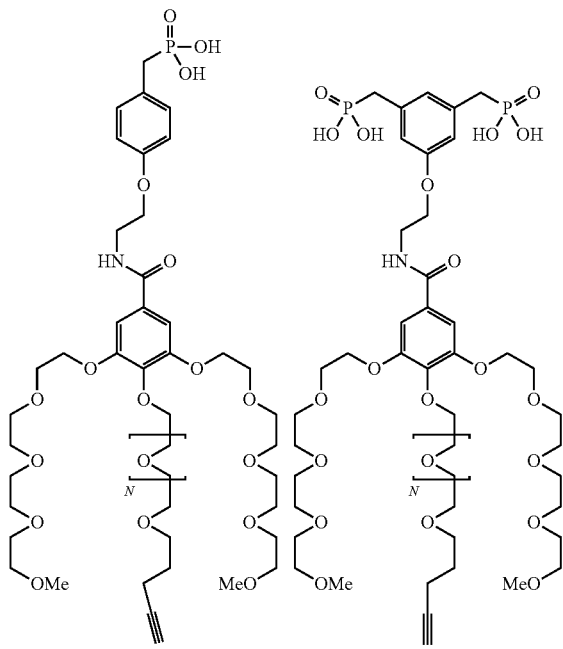
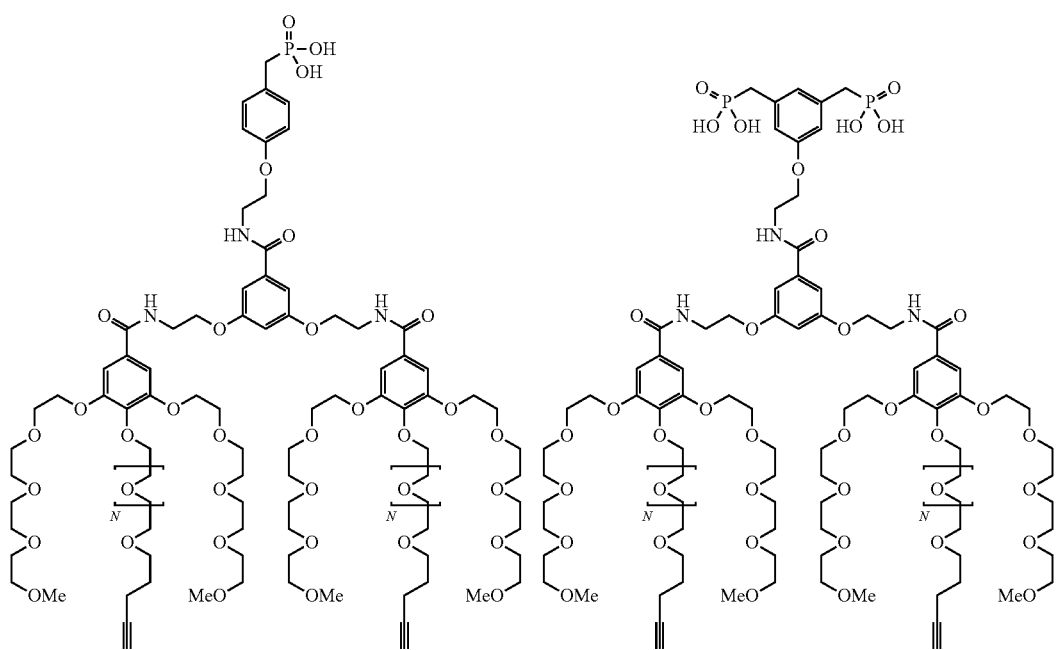

-continued

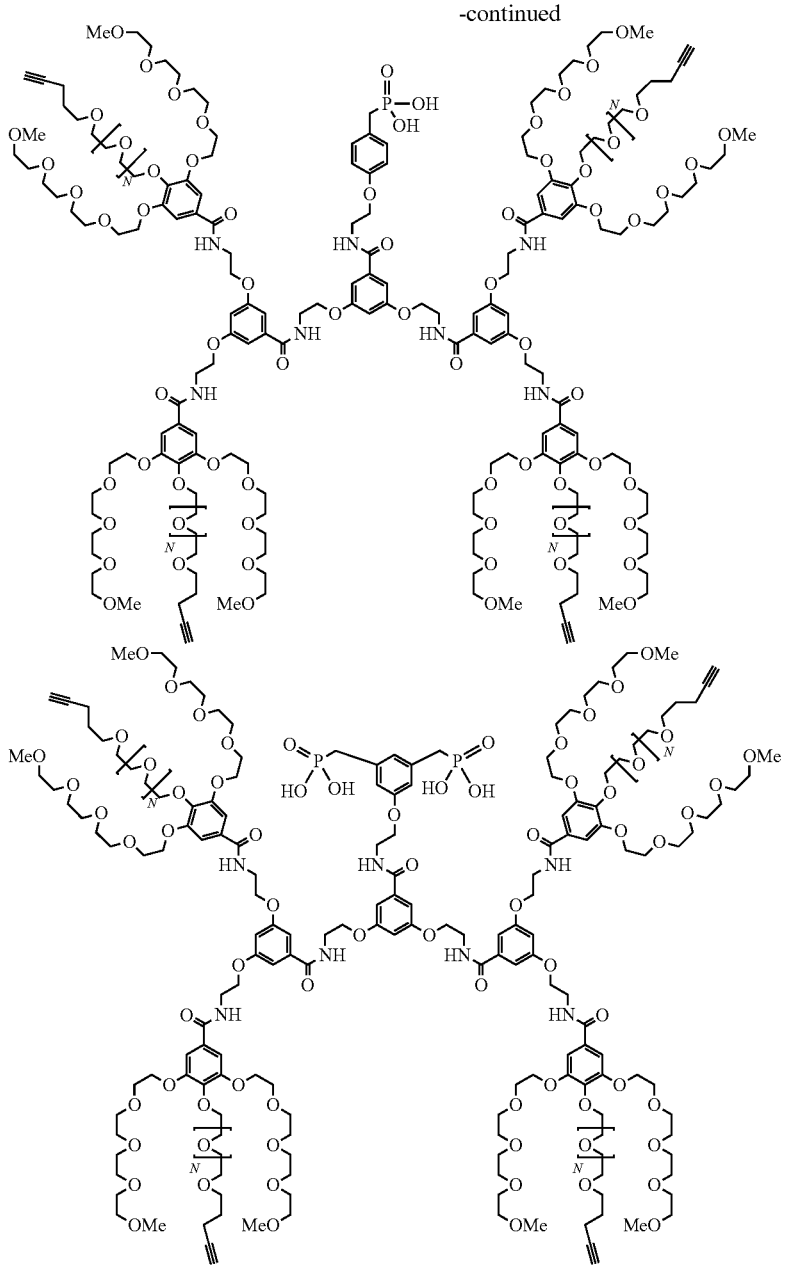

wherein z is equal to 1, 2, 3, 4, 5, 6, 7, 8, 9, 10, 11 or 12, in particular 7, said metallic oxide nanoparticle being in particular:
- a homogenous metallic oxide nanoparticle of $Fe_{3-\delta}O_4$ with $\delta$ being such as $0<\delta<1/3$, or
- a homogenous metallic oxide nanoparticle of $\gamma Fe_2O_3$, or
- a homogenous metallic oxide nanoparticle of $M'Fe_2O_4$ wherein M' is a metal selected from the group constituted of Zn, Co, Mn, Ni and Mg,
- of core-shell $FeO@Fe_3O_4$ structure, or
- of core-shell $Fe_3O_4@MnO$ structure, or
- of core-shell $Fe_3O_4@Au$ structure, or
- of core-shell $M'Fe_2O_4@\ M''Fe_2O_4$ structure, wherein M' is a metal selected from the group constituted of Zn, Co, Mn, Ni and Mg and wherein M" is a metal selected from the group constituted of Zn, Co, Mn, Ni and Mg, M' being different from M".

In another aspect, the present invention relates to a chain of functionalized metallic oxide nanoparticles as described above.

By "chain" is meant a group of nanoparticles comprising a subgroup of nanoparticles wherein each nanoparticle is coupled to two other nanoparticles by dipolar interaction.

Said chain is in particular linear, and comprise more particularly from 3 up to 20 nanoparticles.

Interestingly, the Inventors have found that the limited size of the compounds of formula (I) enable the functionalized metallic oxide nanoparticles to gather in chains.

In another aspect, the present invention relates to a functionalized metallic oxide nanoparticle or a chain of functionalized metallic oxide nanoparticles as described above, for its use as medical imaging tool, in particular optical imaging tool or magnetic resonance imaging tool, more particularly magnetic resonance imaging contrast agent.

By "contrast agent" is meant an agent that can artificially modify the contrast between tissues or cells of different types to visualize an anatomical or pathological structure, more especially cells, such as tumor cells, which presents naturally no specific contrast and is difficult to distinguish from surrounding tissue.

In an advantageous embodiment, the present invention relates to a functionalized metallic oxide $Fe_3O_4$@MnO or $Fe_{3-\delta}O_4$@MnO nanoparticle as described above, for its use as medical bimodal imaging tool, in particular optical imaging tool or magnetic resonance imaging tool, more particularly magnetic resonance imaging T1, T2* and T2 contrast agent.

In an advantageous embodiment, the present invention relates to a functionalized metallic oxide nanoparticle or a chain of functionalized metallic oxide nanoparticles as described above, comprising at least one group R representing a fluorophore or a biocompatible dye, for its use as fluorescent optical imaging tool.

Optical imaging based on RAMAN spectroscopy is also possible, whether R represents a fluorophore, or not.

In an advantageous embodiment, the present invention relates to a functionalized metallic oxide nanoparticle or a chain of functionalized metallic oxide nanoparticles as described above, for its use as multimodal imaging tool.

In another aspect, the present invention relates to a functionalized metallic oxide nanoparticle or a chain of functionalized metallic oxide nanoparticles as described above, for its use as a hyperthermia and/or radiosensitizing agent for the treatment of tumors or other pathological tissues.

In an advantageous embodiment, the present invention relates to a functionalized metallic oxide FeO@$Fe_3O_4$ or FeO@$Fe_{3-\delta}O_4$ nanoparticle as described above, for its use as a hyperthermia and/or radiosensitizing agent for the treatment of tumors or other pathological tissues.

In an advantageous embodiment, the present invention relates to a functionalized metallic oxide nanoparticle or a chain of functionalized metallic oxide nanoparticles as described above, comprising at least one group Y representing a ligand targeting tumor cells, abnormal cells in respect to their metabolic state or their activation state, or elements of the connective tissue of said tumor or abnormal cells, for its use as a hyperthermia and/or radiosensitizing agent for the treatment of tumors, said tumors being in particular:

Melanomas, Y being more particularly of formula V1:

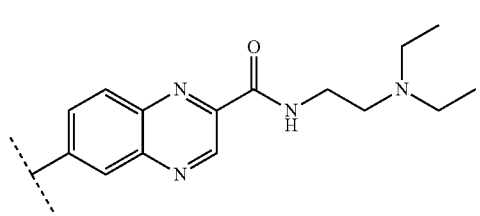

chondrosarcomas, Y being more particularly of formula V2 or V3:

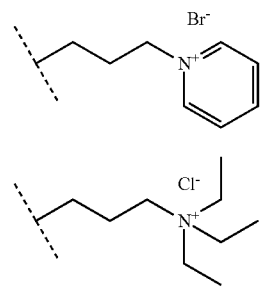

glioblastomas or neuroendocrine tumors, glioblastomas or breast tumors, Y being more particularly tumor Human Epidermal Growth Factor Receptor 2 (HER2) ligand, such as a specific antibody;

prostate tumors, Y being more particularly a specific antibody targeting the PSMA receptor;

solid or not solid tumors, such as melanomas, breast cancers, gliomas, pancreatic cancer and myelomas, Y being more particularly a tripeptide, a pseudo-tripeptide, a tetrapeptide or a pseudo-tetrapeptide, targeting nucleolin, for example a pseudo-tripeptide of formula V4a, V4b or V4c:

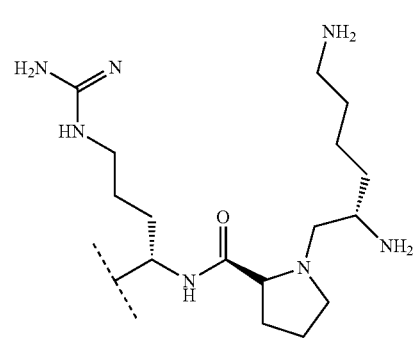

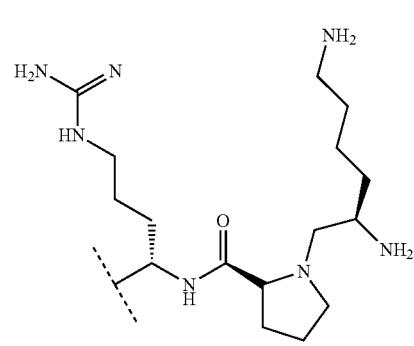

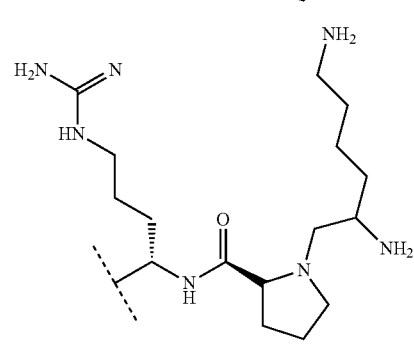

hypoxic cells, Y being more particularly a nidazole derivative (MISO, METRO);

apoptotic cells, Y having more particularly reactive oxygen, for example able to react with caspase.

breast cancer cells, Y being more particularly Herceptin®.

In a particularly advantageous embodiment, the present invention relates to a functionalized metallic oxide nanoparticle or a chain of functionalized metallic oxide nanoparticles as described above, comprising at least two groups Y, identical or different, representing a ligand targeting tumor cells, abnormal cells in respect to their metabolic state or their activation state, or elements of the connective tissue of said tumor or abnormal cells, for its use as a hyperthermia and/or radiosensitizing agent for the treatment of tumors, in particular gliomas, said two groups Y being in particular a nidazole derivative, in particular METRO, and a tripeptide, a pseudo-tripeptide, a tetrapeptide or a pseudo-tetrapeptide, targeting nucleolin.

In a particularly advantageous embodiment, the present invention relates to a functionalized metallic oxide nanoparticle or a chain of functionalized metallic oxide nanoparticles as described above, comprising at least two groups Y, identical or different, representing a ligand targeting tumor cells, abnormal cells in respect to their metabolic state or their activation state, or elements of the connective tissue of said tumor or abnormal cells, for its use as a hyperthermia and/or radiosensitizing agent for the treatment of tumors, in particular gliomas, said two groups Y being in particular:
  a nidazole derivative, in particular METRO, and a nucleotide, or
  a tripeptide, a pseudo-tripeptide, a tetrapeptide or a pseudo-tetrapeptide, targeting nucleolin, and a nucleotide.

In this embodiment, the first Y group (a nidazole derivative or a tripeptide, a pseudo-tripeptide, a tetrapeptide or a pseudo-tetrapeptide, targeting nucleolin) targets tumoral cells, and then the second Y group (a nucleotide) targets said cells nucleus, enhancing the therapeutic efficacy of said nanoparticles.

In an advantageous embodiment, the present invention relates to a functionalized metallic oxide nanoparticle or a chain of functionalized metallic oxide nanoparticles as described above, comprising at least one group R representing a radioelement chelant, for its use as a radiotherapeutic drug for the treatment of tumors.

In another aspect, the present invention relates to a pharmaceutical composition comprising functionalized metallic oxide nanoparticles or chains of functionalized metallic oxide nanoparticles as described above, as active agents and a pharmaceutically acceptable vehicle.

In another aspect, the present invention relates to a diagnostic composition comprising functionalized metallic oxide nanoparticles or chains of functionalized metallic oxide nanoparticles as described above, as active agents and a pharmaceutically acceptable vehicle.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semi-synthetic glycerides or polyethylene glycols.

The compositions can also be aerosols.

For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle, for example dextran, mannitol or lactose.

In an advantageous embodiment, the present invention relates to a pharmaceutical or diagnostic composition defined above, said composition comprising functionalized magnetic metallic oxide nanoparticles or chains of functionalized magnetic metallic oxide nanoparticles as described above, said composition being administrable by intravenous route or intra-cavitary route at a dose comprised from about 1 µg/kg to about 50 mg/kg at equivalent iron and/or magnetic metallic atoms concentration.

By "at equivalent iron and/or magnetic metallic atoms concentration" is meant that said doses are given as the amount of iron and/or magnetic metallic atoms in said composition by kg of body weight.

In an advantageous embodiment, the present invention relates to a pharmaceutical or diagnostic composition defined above, under a form liable to be administrable by intravenous route at an unitary dose comprised from 0.1 mg to 1000 mg, in particular from 10 mg to 1,000 mg, in particular from 10 to 500 mg, in particular from 10 to 100 mg.

Said pharmaceutical or diagnostic composition can be administered 1 to 4 times per day, preferably 2 or 3 times per day.

FIGURES

FIG. 1A presents the specific loss power (SLP) in W/g of the nanoparticles oxNC16, NC16 and NS19, obtained respectively in example 2, example 1 and example 15, as a function of the Fe concentration of said nanoparticles, to evaluate the heating efficiency of said nanoparticles.

Figure 1B:
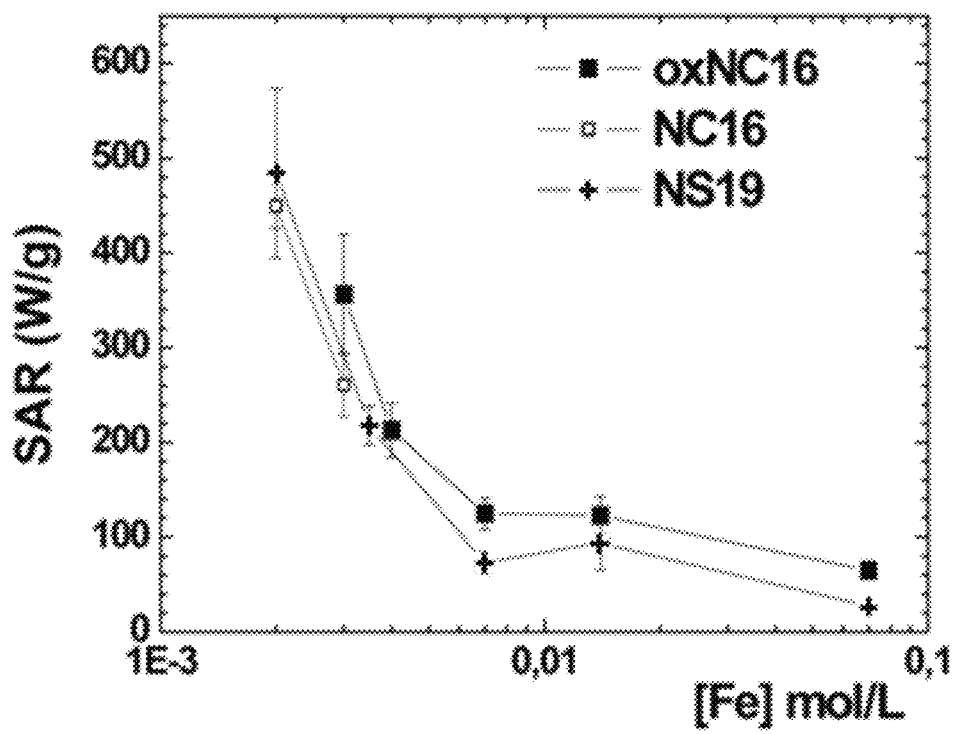

FIG. 1B presents the specific absorption rate (SAR) in W/g of the nanoparticles oxNC16, NC16 and NS19, obtained respectively in example 2, example 1 and example 15, as a function of the Fe concentration of said nanoparticles, to evaluate the heating efficiency of said nanoparticles.

Figure 2:
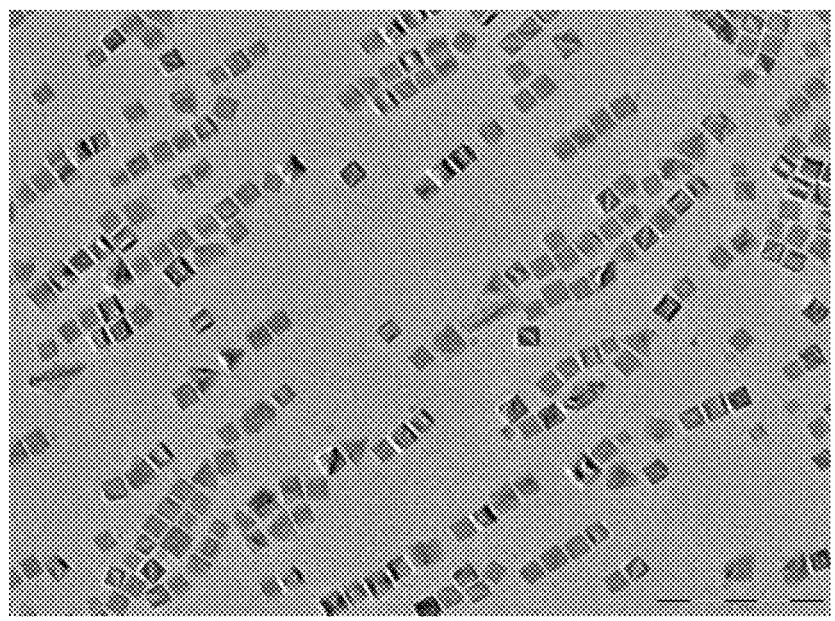

FIG. 2 presents chains of core-shell FeO@$Fe_3O_4$ nanocubes with a size of 16 nm (NC16), obtained in example 1, and observed in transmission electron microscopy (TEM) without applying a magnetic field.

Figure 3:
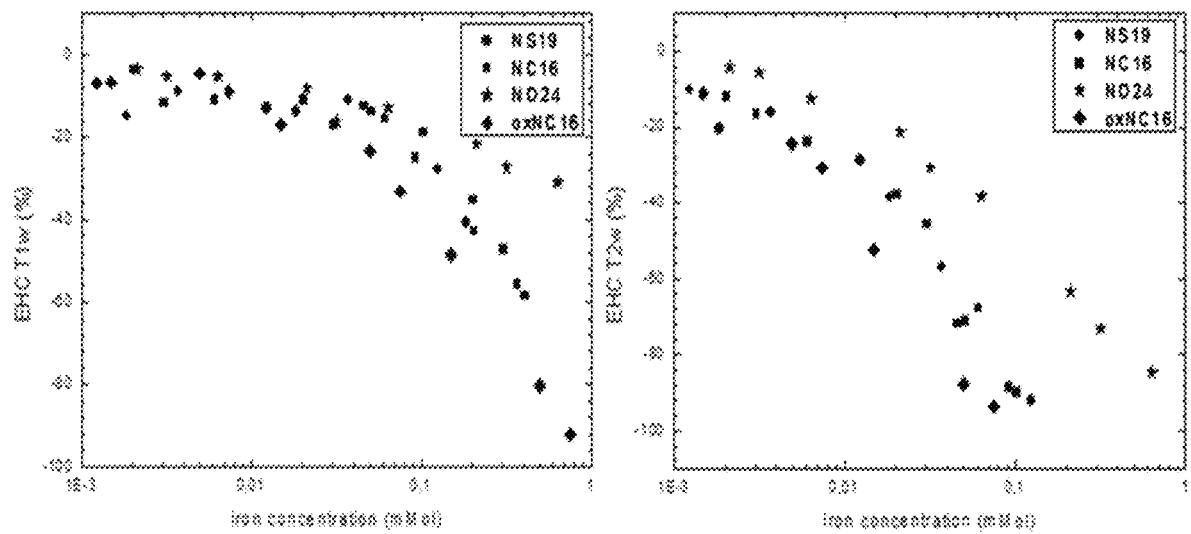

FIG. 3 presents the T1w and T2w EHC values [EHC (%)w=[(Signal value at each equivalent iron concentration)−(signal value of water))/signal value of water)×100] for NS19 (example 15), NC16 (example 1), NO24 (example 14) and oxNC16 (example 2) nanoparticles, calculated from in vitro MRI measurements at 7 T.

Figure 4:
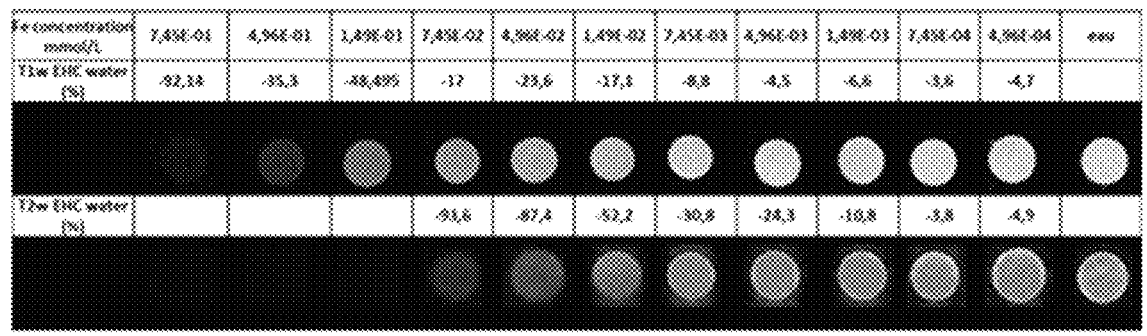
Figure 4:
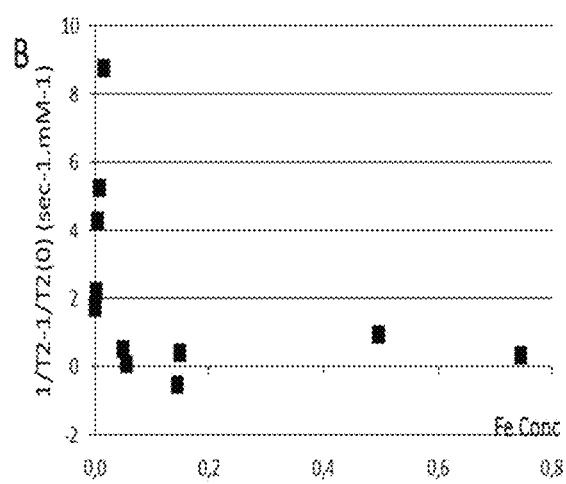
Figure 4:
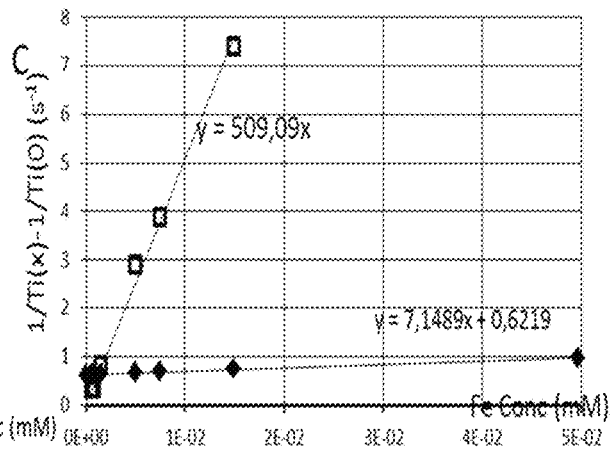

FIG. 4 presents in vitro results for the nanoparticles NC16 obtained in example 1.

FIG. 4A presents the T1w and T2w MR images of samples containing increased iron concentration acquired at 7 T reflecting the contrast enhancement properties of said nanoparticles evaluated in vitro.

FIG. 4B presents the shift between the T1 measurements of NC16 sampling and water in function to the iron concentration in the range of 7.5 E-4 et 7.5 E-1 mM.

FIG. 4C presents the calculation of the transverse relaxivity rate (R2), estimated at 509 mmol·l$^{-1}$·s$^{-1}$ and the longitudinal relaxivity rate (R1) at 7.1 mmol·l$^{-1}$·s$^{-1}$, for said nanoparticles.

Figure 5:
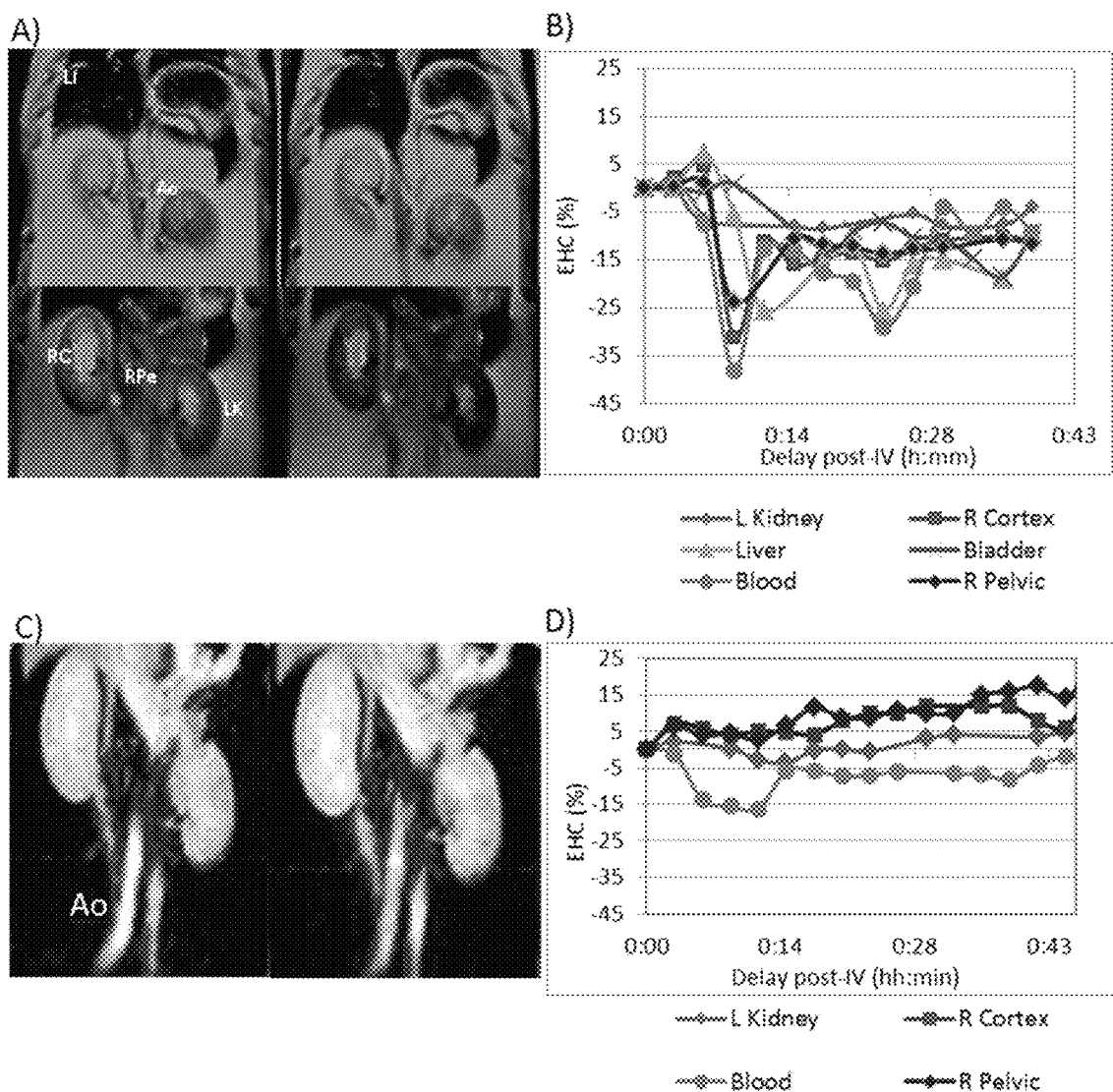

FIG. 5A presents T2w images centered on the liver and aorta (upper) and kidneys (lower), before (left) and at the peak signal (right) after injection of NS19 after injection of NS19 (Li=Liver, Ao=Aorta, RC=Right Cortex, RPe=Right Pelvic, LK=Left Kidney).

FIG. 5B presents the generated EHC time curves corresponding to main organs (Liver, Aorta (Blood), Right Cortex, Right Pelvic, Left Kidney, Bladder) after injection of NS19.

FIG. 5C presents T1w images centered on the aorta and kidneys, before (left) and at the peak signal (right) after injection of NS19 (Ao=Aorta).

FIG. 5D presents the EHC time curves corresponding to main organs (Blood=Aorta, Right Cortex, Right Pelvic, Left Kidney) after injection of NS19.

Figure 6:
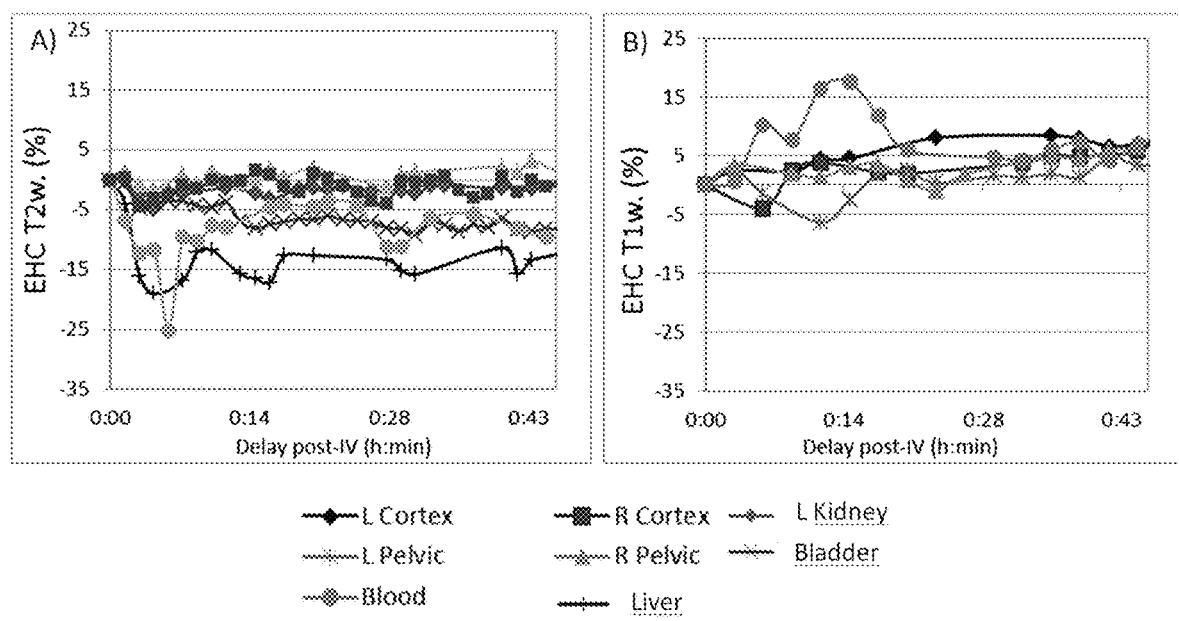

FIG. 6A presents the generated EHC time curves in organs from T2w MRI images at 7 T after IV injection of oxidized nanocubes ox NC16 (iron concentration 1.9 mmol/kg).

FIG. 6B presents EHC curves in main organs generated from T1w dynamic MRI acquisition at 7 T before and after IV injection of oxidized nanocubes ox NC16 (at equivalent iron concentration 1.3 mmol/kg).

Figure 7:
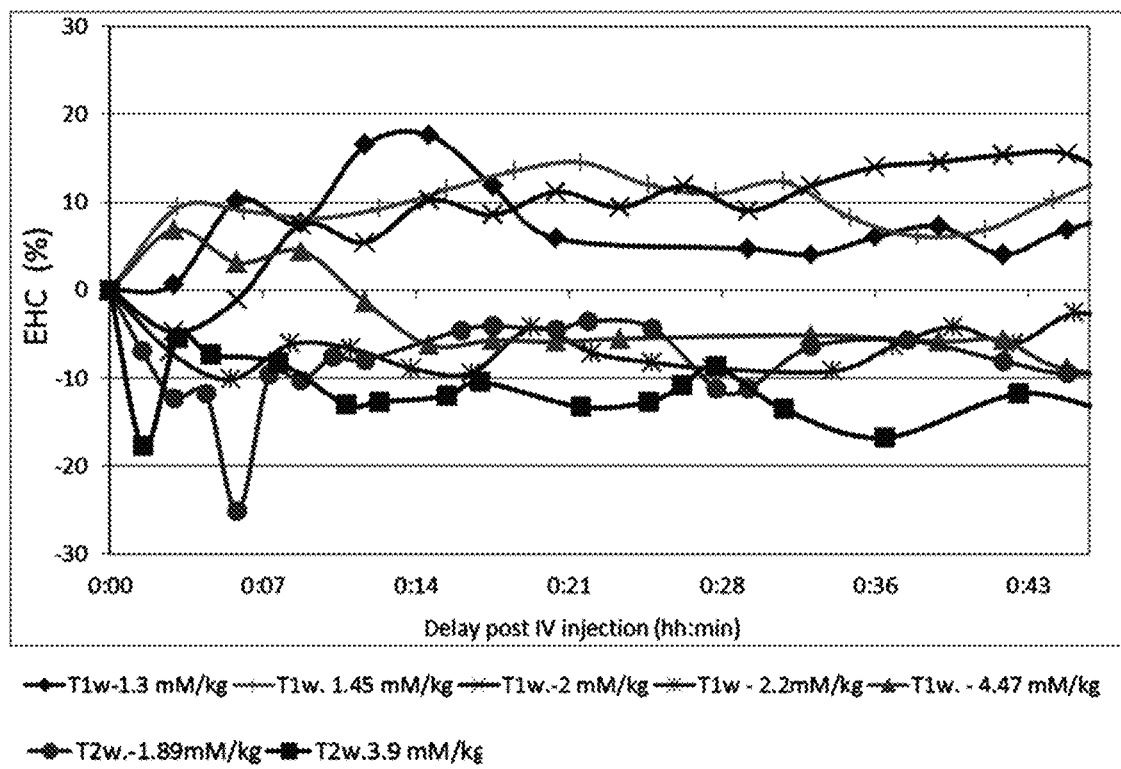

FIG. 7 presents EHC time curves in the aorta (blood) generated from T1w and T2w dynamic MRI acquisition at 7 T before and after IV injection of oxNC16 at different concentrations.

Figure 8:
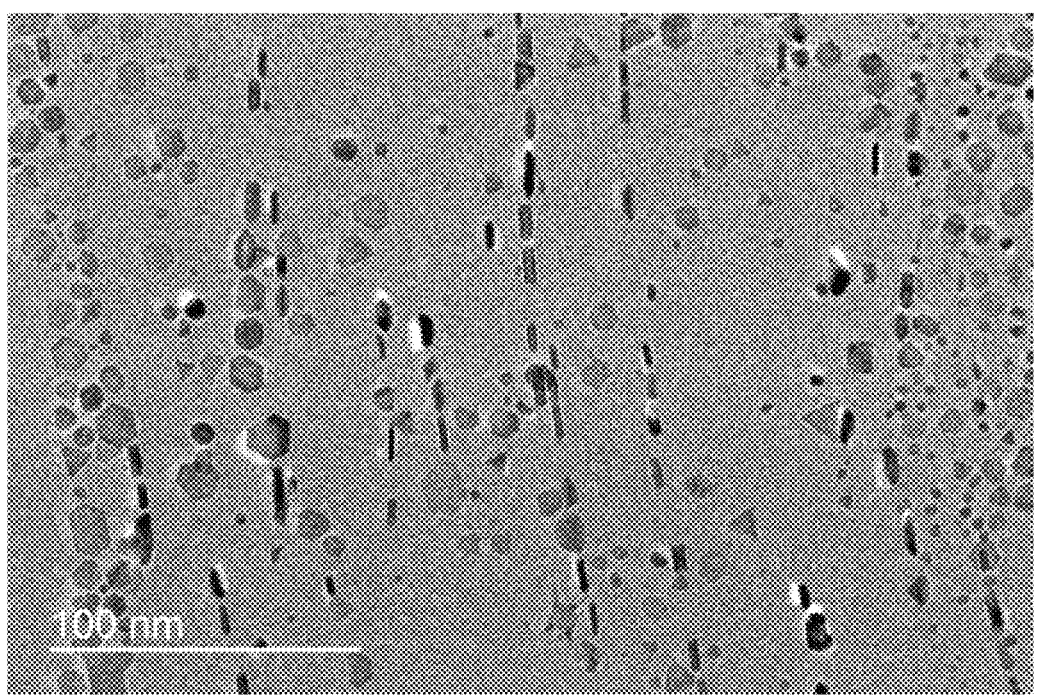

FIG. 8 presents nanoplatelets according to the present invention, observed in transmission electron microscopy (TEM).

Figure 9:
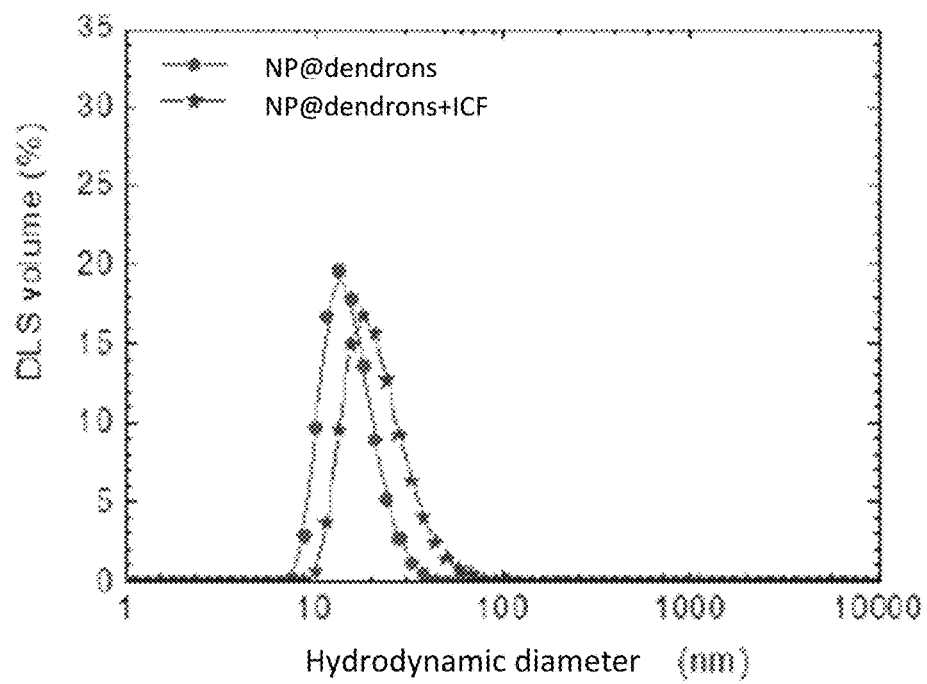

FIG. 9 presents the volume distribution of the hydrodynamic diameter of the NPs@dendrons before and after coupling with ICF.

Figure 10:
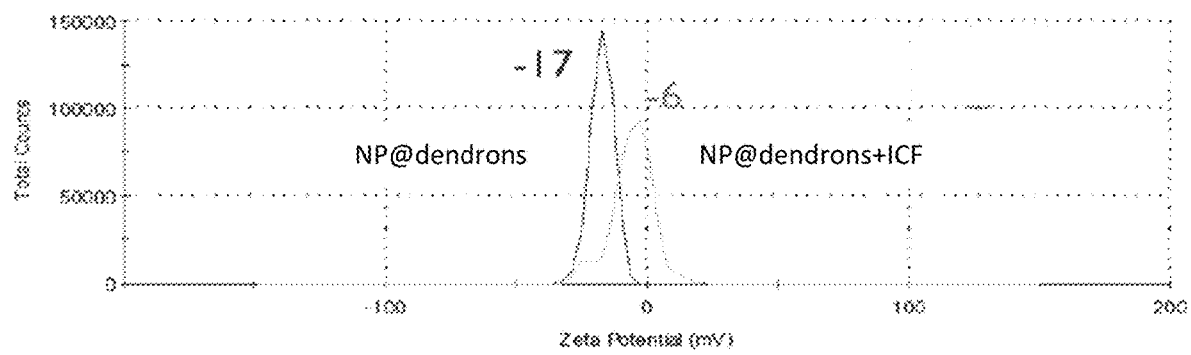

FIG. 10 presents the curves of zeta potential of the NPs@dendrons before and after coupling with ICF.

Figure 11:
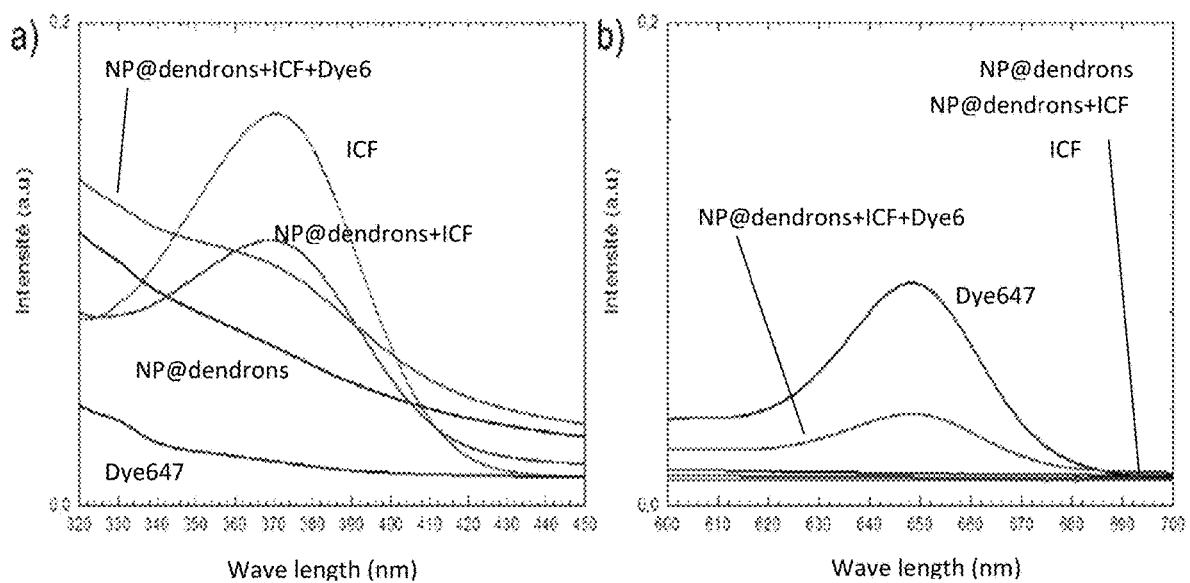
Figure 12:
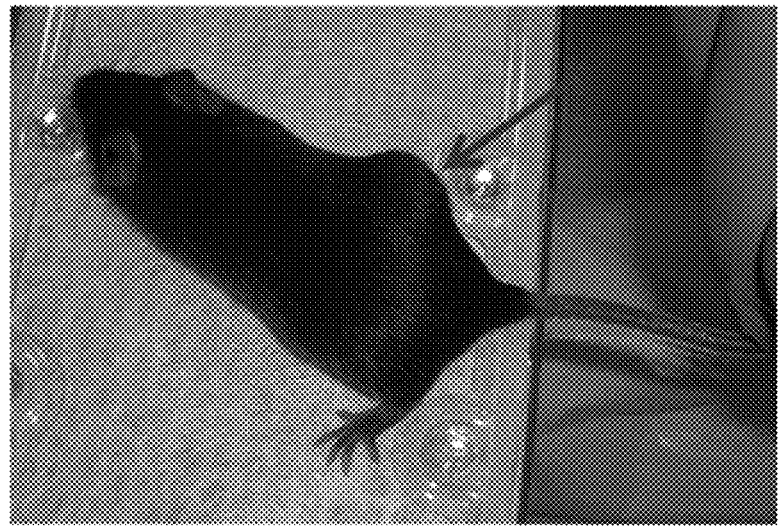

FIG. 11a) presents the UV-visible spectrum of the NPs@dendrons before and after coupling with ICF and fluorophore Dye647, between 320 and 450 nm FIG. 11b) presents the UV-visible spectrum of the NPs@dendrons before and after coupling with ICF and fluorophore Dye647, between 600 and 700 nm FIG. 12 presents the picture of a mouse with a melanoma tumor (arrow).

Figure 13:
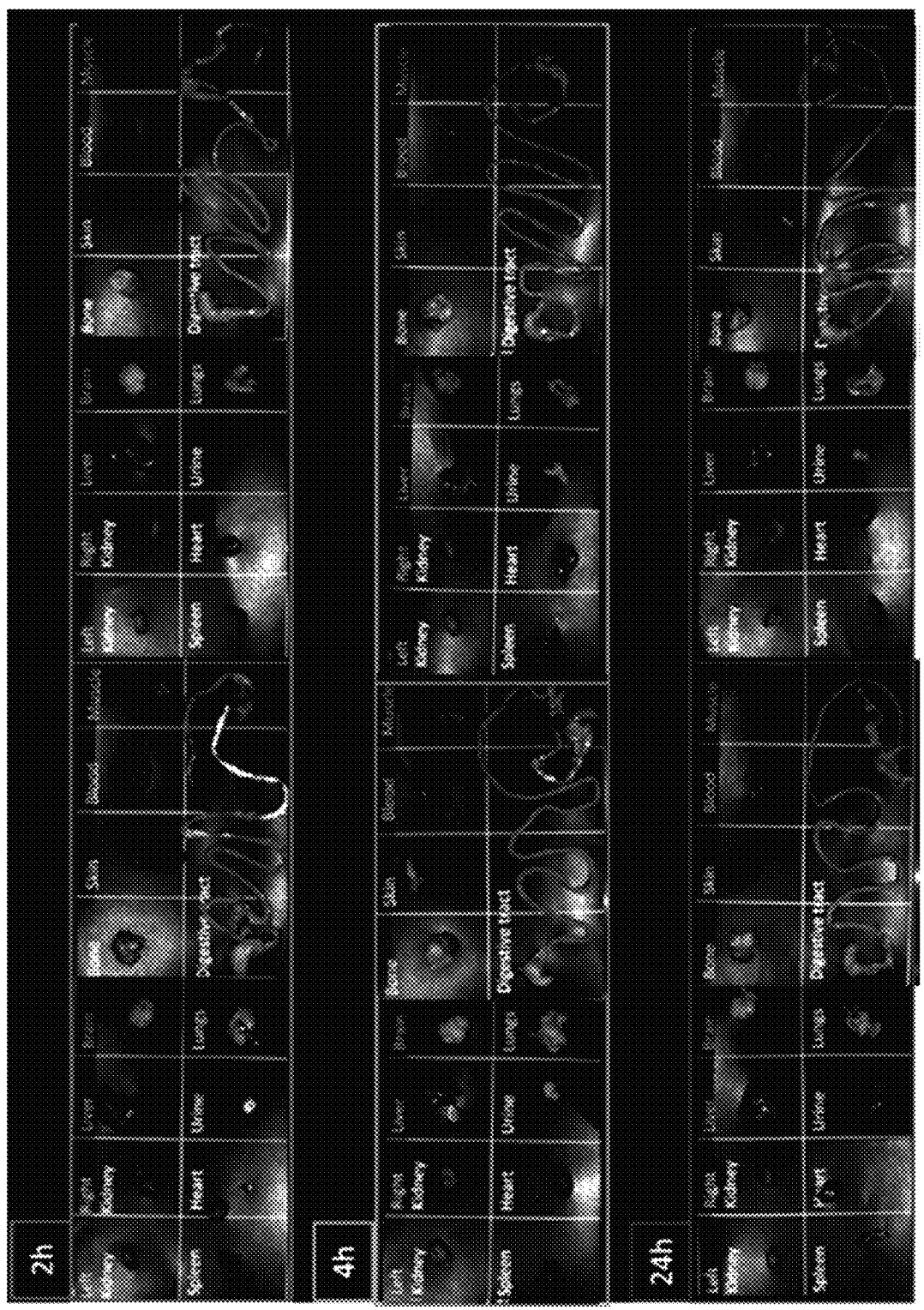

FIG. 13 presents the statistic imagery of organs after injection of 100 µl of a solution of NPs@dendrons+ICF+Dye647. Sacrifice of 3 mice by time and organs imagery ex vivo.

Figure 14:
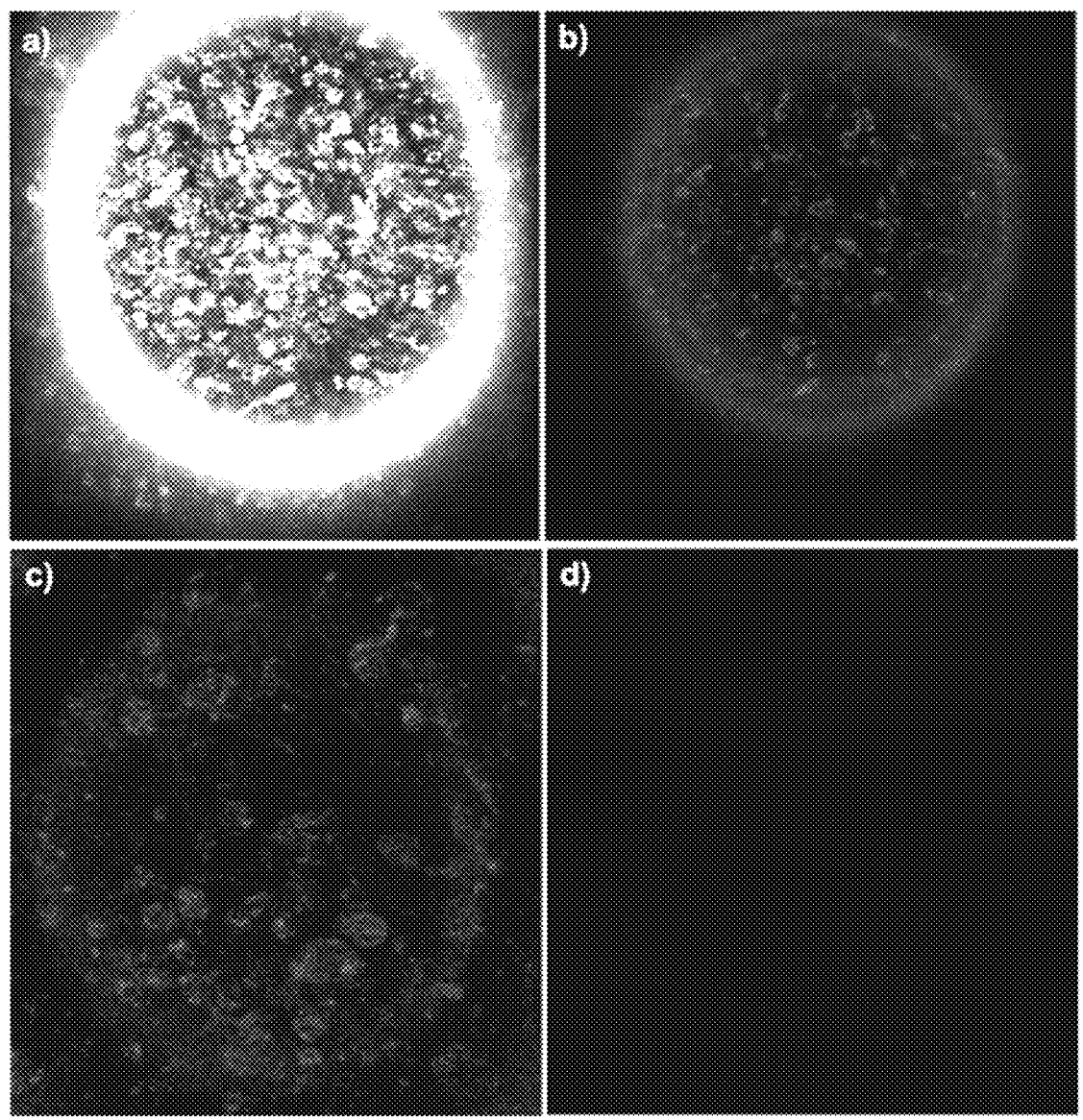

FIG. 14 presents the confocal ex vivo analysis of melanoma tumors taken 3 hours after injection of NPs@dendrons+ICF+Dye647 and NPs@dendrons+Dye495.

FIG. 14a): reflectance image showing the autofluorescence of the melanine granules.

FIG. 14b): fluorescence image recorded at 688 nm: localization of the NPs@dendrons+ICF+Dye647.

FIG. 14c): superposition of the autofluorescence of the melanine granules and the fluorescence of the NPs@dendrons+ICF+Dye647.

FIG. 14d): image recorded at 488 nm: no NPs@dendrons+Dye495 in the tumor.

Figure 15:
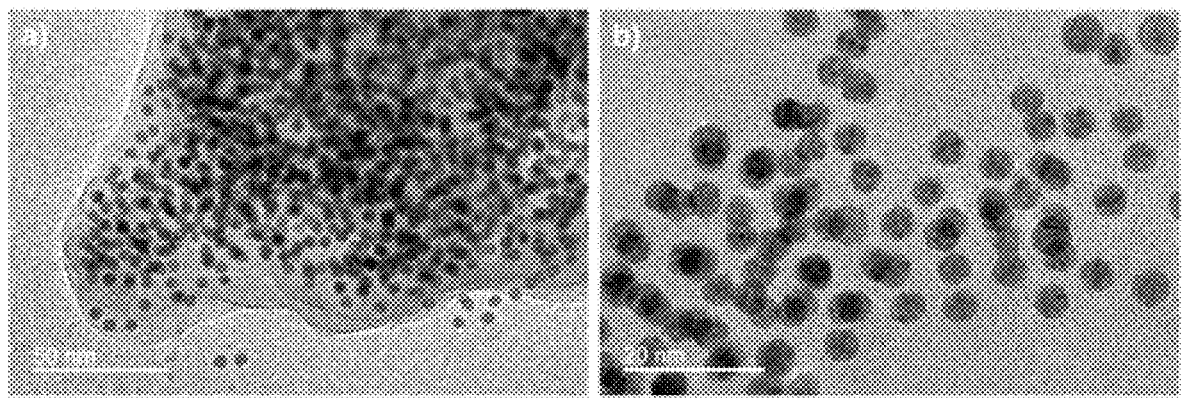

FIG. 15 presents (two scales) TEM images of the residues of a calcinated melanoma tumor wherein a solution of NPs@dendrons+ICF has been injected.

EXAMPLES

In the following examples, the formula $Fe_{3-x}O_4$ depicts $Fe_3O_4$ nanoparticles, which are slightly oxidized on their surface due to their nanosize.

Example 1: Synthesis of Core-Shell FeO@$Fe_{3-x}O_4$ Cubic-Shaped Iron Oxide Nanoparticles (NC16, Mean Size: 16 nm)

By FeO@$Fe_{3-x}O_4$ is meant a core-shell composition with a FeO core and a $Fe_{3-x}O_4$ shell. First of all, the iron oleate complex Fe(oleate)$_3$ was prepared from 10.8 g (40.0 mmol) FeCl$_3$.6H$_2$O (99%, Merck) dissolved in 60 ml H$_2$O (Milli-Q) and 80 ml ethanol. 36.5 g (120 mmol) of sodium oleate dissolved in 140 ml hexane were then mixed with the iron (III) solution. The resulting biphasic mixture was then refluxed at 70° C. for 4 h under stirring. Then, the organic phase containing the iron complex was separated, washed three times with 30 ml of distilled water at 50° C. to extract salts and then dried over MgSO$_4$. The evaporation of hexane led to a waxy solid.

Secondly, (2.08 mmol) of Fe(oleate)$_3$, 0.705 g (2.32 mmol) of sodium oleate (>97.0%, TCI) and 0.2 ml (0.65× 10$^{-3}$ mol) of oleic acid (99%, Alfa-Aesar) were added to 15 ml of octadecene (90%, Fluka, b.p. 318° C.). The mixture was heated at 120° C. in the absence of a reflux condenser for 1 h to evaporate the traces of unwanted solvent and to dissolve the reactants. The solution was first quickly heated to 200° C. without stirring and maintained at this temperature for 10 minutes. Then the solution was heated at a rate of 1° C./min up to 320° C. and was refluxed for 60 min either under argon or air. The resultant black solution was cooled down to room temperature and the NPs were washed three times by addition of acetone and centrifugation (14000 rpm, 10 min.). The cubic-shaped NPs, were then easily suspended in chloroform and displayed a mean size of about 16 nm. They are named NC16.

Example 2: Oxidation of Core-Shell FeO@$Fe_{3-x}O_4$ Cubic-Shaped Iron Oxide Nanoparticles (oxNC16)

50 mg of cubic nanoparticles synthesized as described in example 1 were dispersed in toluene and heated to reflux during 48 h with bubbling air inside the suspension. After this post synthesis oxidation step, the nanoparticles were dispersed and stored in THF after evaporation of the toluene. oxNC16 nanoparticles displayed a mean size of about 16 nm.

Example 3: Synthesis of Core-Shell FeO@Fe$_{3-x}$O$_4$ Cubic-Shaped Iron Oxide Nanoparticles (Mean Size: 13 nm)

The synthesis was performed in the same conditions as those of example 1, but with a heating rate adjusted to 5° C. min$^{-1}$ instead of 1° C. min$^{-1}$ and led to cubic-shaped NPs with a mean size of 13 nm.

Example 4: Synthesis of Core-Shell FeO@Fe$_{3-x}$O$_4$ Cubic-Shaped Iron Oxide Nanoparticles (Mean Size: 30 nm)

The synthesis was performed in the same conditions as those of example 1, but the solvent was changed to eicosene (Aldrich, 90%) and the solution was refluxed for only 15 minutes to obtain nanocubes of 30 nm.

Example 5: Synthesis of Spherical Homogenous Fe$_{3-x}$O$_4$ Nanoparticles (Mean Size of 10.1 nm)

Spherical iron oxide nanocrystals were synthesized by thermal decomposition of iron stearate in octylether. 1.38 g (2.22 mmol) of Fe(stearate)$_2$ (Strem Chemicals) and 1.24 g (4.44 mmol) of oleic acid (99%, Alfa Aesar) were added to 20 mL octyl ether (99%, Fluka, b.p. 287° C.). The mixture was heated and kept at 100° C. under stirring for 15 min in order to dissolve the reactants. The solution was heated to 287° C. with a heating rate of 5° C./min without stirring and was refluxed for 120 min at this temperature under air. A black suspension containing spherical NPs is obtained. These standard conditions lead to NPs with a mean size of 10.1 nm, labeled NP10.

Example 6: Synthesis of Spherical Homogenous Fe$_{3-x}$O$_4$ Nanoparticles (Mean Size of 5.4 nm)

NP5 nanoparticles (d=5.4 nm) have been obtained by using the same procedure as the one of example 5, with hexadecene as solvent (T$_b$=274° C.).

Example 7: Synthesis of Spherical Homogenous Fe$_{3-x}$O$_4$ Nanoparticles (Mean Size of 14.7 nm)

NP15 nanoparticles (d=15.5 nm) have been obtained by using the same procedure as the one of example 5, with eicosene as solvent (T$_b$=330° C.).

Example 8: Synthesis of Spherical Homogenous Fe$_{3-x}$O$_4$ Nanoparticles (Mean Size of 20.3 nm)

NP20 nanoparticles (d=20.3 nm) have been obtained by using the same procedure as the one of example 5, except that the reactants were dissolved in docosene (Tb=355° C.), and the solution was maintained at 250° C. for 30 min, then heating quickly the solution to reflux for 2 h.

Example 9: Synthesis of Spherical Homogenous Fe$_{3-x}$O$_4$ Nanoparticles (Mean Size of 28 nm)

NP30 nanoparticles (d=28 nm) have been obtained by using the same procedure as the one of example 5, except that the reactants were dissolved in docosene (Tb=355° C.), and the solution was maintained at 250° C. for 1 h, then heating quickly the solution to reflux for 2h.

Example 10: Synthesis of Spherical Homogenous Manganese Oxide Nanoparticles

The same conditions of synthesis as those used for iron oxide nanoparticles were used, except that manganese acetate was used instead of iron stearate.

Example 11: Synthesis of Spherical Homogenous Doped Ferrite Nanoparticles

The same conditions of synthesis as those used for iron oxide nanoparticles were used, except that a metallic complex (either metal acetate or metal(acac) or metal stearate or metal oleate or any metal precursor decomposing between 180 and 250° C.) is added with iron stearate in stoichiometric proportions according to Fe$_{3-y}$M$_y$O$_4$.

Example 12: Synthesis of Spherical Core-Shell Fe$_{3-x}$O$_4$@M$_x$O$_y$ Nanoparticles General Procedure In a typical synthesis, a two necked round bottom flask was charged with 1.38 g (2.22 mmol) of Fe(stearate)$_2$ (9.47% Fe, Strem Chemicals), 1.254 g (4.44 mmol) of oleic acid (99%, Alfa-Aesar) and 20 mL of octyl ether (97%, Fluka, bp 287° C.) used as solvent. The mixture was sonicated and stirred at 120° C. for 10 mn to dissolve the reactants until a clear solution was obtained. The solution was then heated to boiling temperature (~287° C.) with a heating rate of 5° C./mn and kept at this temperature for 120 minutes under air. The resultant black solution was then cooled to 100° C. 10 ml of solution was taken for characterization of Fe$_{3-x}$O$_4$ nanoparticles.

In a second step, 0.67 g (2.22 mmol) of the metal precursor (stearate/oleate/octanoate . . . of a metal or M(CO)x or M(acac) or any metal precursor decomposing between 180 and 250° C.)) dissolved in 20 mL of octadecene (90%, Alfa Aesar, bp 318° C.) was added to the remaining solution kept at 100° C. and the mixture containing both octyl ether and octadecene was heated again to reflux for 3 hours under argon (heating rate of 1° C./mn). After cooling down to room temperature, each types of nanoparticles (Fe$_3$O$_4$ and Fe$_3$O$_4$@MxOy nanoparticles) were precipitated by the addition of an excess of acetone and washed 3 times by a mixture of hexane/acetone (1/3) by centrifugation (14000 rpm, 10 mn). Finally the Fe$_{3-x}$O$_4$ and Fe$_3$O$_4$@ MxOy nanoparticles were easily suspended in chloroform.

Synthesis of Core-Shell Fe$_{3-x}$O$_4$@CoO Nanoparticles

Fe$_{3-x}$O$_4$@CoO nanoparticles were obtained according to the general procedure, using cobalt stearate and iron stearate as metal precursors.

In particular, Fe$_{3-x}$O$_4$@CoO nanoparticles with a core having a mean diameter of 7 or 10 nm, and a shell of a mean thickness of 0.5, 1 or 2 nm were obtained.

In a typical synthesis, a two necked round bottom flask was charged with 1.38 g (2.22 mmol) of Fe(stearate)$_2$ (9.47% Fe, Strem Chemicals), 1.254 g (4.44 mmol) of oleic acid (99%, Alfa-Aesar) and 20 mL of octyl ether (97%, Fluka, bp 287° C.) used as solvent. The mixture was sonicated and stirred at 120° C. for 10 mn to dissolve the reactants until a clear solution was obtained. The solution was then heated to boiling temperature (~287° C.) with a heating rate of 5° C./mn and kept at this temperature for 120 minutes under air. The resultant black solution was then cooled to 100° C. 10 ml of solution was taken for characterization of $Fe_3O_4$ nanoparticles. In a second step, 0.67 g (2.22 mmol) of Co(stearate)$_2$ (9-10% Co, Strem Chemicals) dissolved in 20 mL of octadecene (90%, Alfa Aesar, bp 318° C.) was added to the remaining solution kept at 100° C. and the mixture containing both octyl ether and octadecene was heated again to reflux for 3 hours under argon (heating rate of 1° C./mn). After cooling down to room temperature, nanoparticles were precipitated by the addition of an excess of acetone and washed 3 times by a mixture of hexane/acetone (1/3) by centrifugation (14000 rpm, 10 mn). Finally the $Fe_3O_4$ and $Fe_3O_4$@CoO nanoparticles were easily suspended in chloroform.

The shell thickness is tuned by varying the amount of cobalt stearate added during the second step: twice and three times the amount of cobalt stearate.

Example 13: Synthesis of Core-Shell Nanoparticles in Two Steps

General Procedure (Adapted to all Types of Nanoparticles Coated with a Surfactant and Stable in Organic Solvent, to all Morphologies: Spherical, Nanocubes, Nanowires and Octopods and all Compositions: $Fe_{3-x}O_4$ and Also Other Types of Ferrites $MFe_2O_4$ with M=Fe, Ni, Zn, Mn or Metal Oxides MxOy with M=Mn)
First Step:
synthesis of the nanoparticles with a given composition and shape and formation of a stable suspension of these nanoparticles coated with surfactants in an organic solvent with a high boiling temperature.
$2^{nd}$ Step:
In a second step, 2.22 mmol of the metal precursor (stearate/oleate/octanoate. of a metal or M(CO)x or M(acac) or any metal precursor decomposing between 180 and 250° C.)) dissolved in 20 mL of octadecene (90%, Alfa Aesar, bp 318° C.) was added to the 10 ml of the solution of pre-synthesized nanoparticles and the mixture was heated again to reflux for 3 hours under argon (heating rate of 1° C./mn). After cooling down to room temperature, the so obtained nanoparticles were precipitated by the addition of an excess of acetone and washed 3 times by a mixture of hexane/acetone (1/3) by centrifugation (14000 rpm, 10 mn). Finally the core-shell nanoparticles were easily suspended in chloroform.

Synthesis of Core-Shell $Fe_{3-x}O_4$@MnO Nanoparticles
$Fe_{3-x}O_4$@MnO nanoparticles were obtained according to the two steps procedure, using iron stearate and manganese acetate (Mn(acetat)$_2$) as metal precursor.
Synthesis of $Fe_3O_4$ Seeds
Iron oxide NPs were synthesized by thermal decomposition of an iron stearate complex in presence of oleic acid in a high boiling solvent. 1.38 (2.2 mmol) of Fe(stearate)$_2$ and 1.25 g (4.4 mmol) of oleic acid (OA) were added to 20 mL of octyl ether (b.p 288° C.). The mixture was heated at 110° C. during 30 minutes until all the reactants were completely dissolved. The solution was heated to 288° C. with a heating rate of 5° C./min and was reflux for 120 min at this temperature under air. The resulting black solution was then cooled down to room temperature and the NPs were washed 3 times by addition of ethanol and by centrifugation. The as synthesized NPs, named $Fe_3O_4$ seeds, were then easily suspended in hexane.
Synthesis of Core-Shell $Fe_3O_4$@MnO Nanoparticles
A MnO shell was grown on the $Fe_3O_4$ seeds previously synthesized using a seeds mediated growth method. 0.38 g (2.2 mmol) Mn(acetate)$_2$ and 1.86 g (6.6 mmol) OA were added to 15 mL octadecene. 3 ml of $Fe_3O_4$ seeds solution (4.87 mg/mL) in hexane were injected in the mixture. The solution was heated at 110° C. during 1 h until all the reactants were completely dissolved and the hexane evaporated. The solution was then slowly increased (1° C./min) to 318° C. and was reflux for 60 min. The resulting black solution was then cooled down to room temperature and the NPs were washed 3 times by addition of ethanol or acetone and by centrifugation. The as synthesized NPs, named $Fe_3O_4$@MnO, were then easily suspended in THF.

In particular, $Fe_{3-x}O_4$@MnO nanoparticles with a core having a mean diameter of 6 nm, and a shell of a mean thickness of 6.5 nm were obtained.

The shell thickness is tuned by varying the amount of Mn(acetate)$_2$ added during the second step: 0.25, 0.5 and twice times the amount of Mn(acetate)$_2$.

Synthesis of Core-Shell $CoFe_2O_4$@MnO Nanoparticles
$CoFe_2O_4$@MnO nanoparticles were obtained according to the general procedure, using cobalt stearate, iron stearate and manganese acetate as metal precursor.
0.38 g (2.2 mmol) Mn(acetate)$_2$ and 1.86 g (6.6 mmol) OA were dissolved in 20 mL of octadecene (90%, Alfa Aesar, bp 318° C.) was added to the 10 ml of the solution of pre-synthesized $CoFe_2O_4$ nanoparticles and the mixture was heated again to reflux for 3 hours under argon (heating rate of 1° C./mn). After cooling down to room temperature, the so obtained nanoparticles were precipitated by the addition of an excess of acetone and washed 3 times by a mixture of hexane/acetone (1/3) by centrifugation (14000 rpm, 10 mn). Finally the core-shell nanoparticles were easily suspended in chloroform.

In particular, $CoFe_2O_4$@MnO nanoparticles with a core having a mean diameter of 8 nm, and a shell of a mean thickness of 2 nm were obtained.

Example 14: Synthesis of Octopods (NO24)

First of all, the iron oleate complex Fe(oleate)$_3$ was prepared from 10.8 g (40.0 mmol) $FeCl_3.6H_2O$ (99%, Merck) dissolved in 60 ml $H_2O$ (Milli-Q) and 80 ml ethanol. 36.5 g (120 mmol) of sodium oleate dissolved in 140 ml hexane were then mixed with the iron (III) solution. The resulting biphasic mixture was then refluxed at 70° C. for 4 h under stirring. Then, the organic phase containing the iron complex was separated, washed three times with 30 ml of distilled water at 50° C. to extract salts and then dried over MgSO4. The evaporation of hexane led to a waxy solid.
Secondly, (2.08 mmol) of Fe(oleate)3, 0.705 g (2.32 mmol) of sodium oleate (>97.0%, TCI) and 0.2 ml (0.65× 10-3 mol) of oleic acid (99%, Alfa-Aesar) were added to 15 ml of octadecene (90%, Fluka, b.p. 318° C.). The mixture was heated at 110° C. in absence of a reflux condenser and then the solution was quickly heated to 220° C. and maintained at this temperature for 10 min. The synthesis mixture was then heated at a rate of 5° C./min and temperature was maintained at 320° C. for 1 h. The resultant black solution was then cooled to room temperature, and the NPs were washed several times by addition of ethanol and by centrifugation (14000 rpm, 10 min). The edges grown cubic NPs or octopodes with a size of 24 nm, were easily suspended in THF. They are named NO24.

Example 15: Synthesis of Core-Shell $FeO$@$Fe_3O_4$ Spherical Nanoparticles (NS19)

Spherical core shell $FeO$@$Fe_3O_4$ NPs were synthesized by thermal decomposition of iron stearate complex in presence of oleic acid in a high boiling point solvent. 1.38 g (2.2 mmol) of Fe(stearate)$_2$ and 1.25 g (4.4 mmol) of oleic acid (OA) were added to 18 g of docosene (B.P 355° C.). The mixture was heated at 110° C. in absence of a reflux condenser for 1H to evaporate the traces of unwanted solvent and to dissolve the reactants. The solution was then heated to 355° C. with a heating rate of 5° C./min and refluxed for 120 min at this temperature under air. The resultant black solution was then cooled to room temperature, and the NPs were washed several times by addition of ethanol and by centrifugation (14000 rpm, 10 min). The nano spheres, named NS19, were easily suspended in THF, and displayed a mean size of about 19 nm.

Example 16: Synthesis of Dendrons 324.0 mmol, 3.0 eq.) and KI (0.1 g, 0.60 mmol) in DMF (100 mL) was stirred during 4 days at 30° C. The reaction mixture was poured into 1 L of water and sulfuric acid was added until obtention of a neutral pH. The aqueous layer was then extracted 3 times with 150 mL of dichloromethane. The combined organic layers were brought together, washed three times with 50 mL of brine, dried over MgSO$_4$ and filtered. The solvent was removed by evaporation and the residue was purified by column chromatography on silica gel eluting with dichloromethane/methanol (98/2) to provide an yellow oil. The crude material was evaporated many times with dichloromethane. The obtained residue was filtered and washed petroleum ether to provide compound 1 as a white solid in 70% yield. $^1$H NMR (300 MHz, CD$_3$OD-d) δ 7.52 (d, J=7.5 Hz, 2H, Ar$^2$-2,6-H), 7.31 (m, 3H, Ar$^2$-3,4,

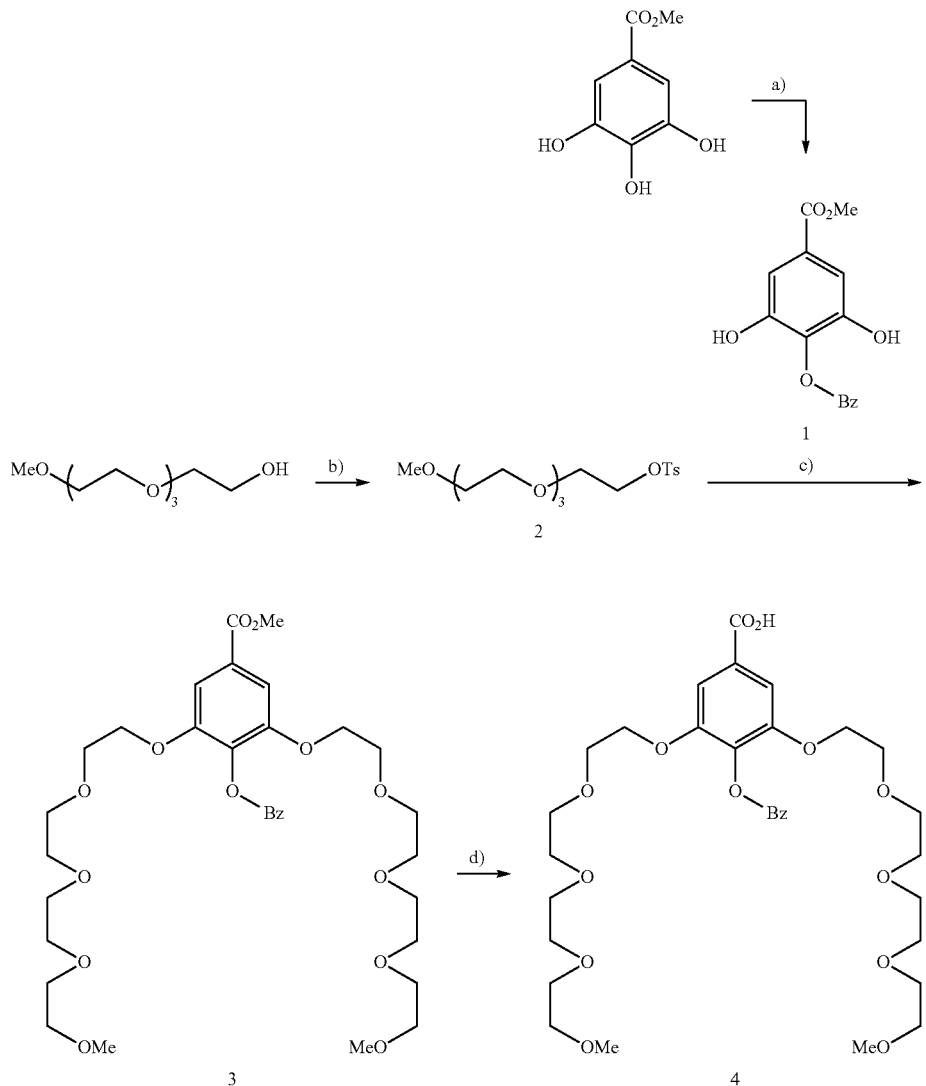

Scheme 1.

a) Benzyl bromide, KHCO$_3$, KI, DMF, 30° C., 4 days; b) TsCl, NaOH, THF/H$_2$O, RT, 24 h; c) K$_2$CO$_3$, KI, acetone, reflux, 24 h; d) NaOH/H$_2$O, reflux, 2 h.

Compound 1:

A solution of methyl gallate (20.0 g, 108.6 mmol), benzyl bromide (14.2 mL, 119.0 mmol, 1.1 eq.), KHCO$_3$ (32.4 g, 5-R), 7.13 (s, 2H, Ar$^1$-2,6-H), 5.18 (s, 2H, Ar$^2$OCH$_2$), 3.83 (s, 3H, COOCH$_3$); $^{13}$C NMR (75 MHz, CD$_3$OD-d) δ 167.1, 150.5, 138.2, 137.2, 128.5, 128.0, 127.8, 125.0, 108.8, 73.8, 51.2.

Compound 2:

A solution of para-toluenesulfonyl chloride (22.3 g, 105 mmol) in THF (35 mL) was added dropwise to a solution of tetraethyleneglycol methyl ether (20.0 g, 96 mmol) and NaOH (6.7 g, 166 mmol) in a mixture of THF/H$_2$O (135 mL/45 mL) at 0° C. After 1 hour stirring at 0° C., the reaction was allowed to warm at room temperature and was stirred 20 additional hours. The solution was then poured into 200 mL of brine and the volatiles were evaporated. The resulting mixture was extracted several times with dichloromethane and the combined organic layers were washed with brine, dried over MgSO$_4$ and filtered. The solvent was evaporated under reduced pressure and the oil and was purified by column chromatography on silica gel eluting with dichloromethane/methanol (98/2). Compound 2 was obtained as a pale yellow oil in 94% yield. $^1$H NMR (300 MHz, CDCl$_3$) δ 7.73 (d, J=1.5 Hz, 2H, Ar-2,6-H), 7.28 (d, J=1.5 Hz, 2H, Ar-3,5-H), 4.11-4.08 (m, 2H, ArSO$_2$OCH$_2$), 3.64-3.47 (m, 14H, OCH$_2$CH$_2$O), 3.31 (s, 3H, OCH$_3$), 2.39 (s, 3H, ArCH$_3$); $^{13}$C NMR (75 MHz, CDCl$_3$) δ 144.9, 133.2, 130.0, 72.1, 70.9, 70.7, 70.6, 69.5, 68.8, 59.1, 28.1, 21.8.

Compound 3:

A solution of 1 (9.2 g, 33.4 mmol), 2 (26.9 g, 74.3 mmol, 2.2 eq.), K$_2$CO$_3$ (28.0 g, 200 mmol, 6.0 eq.) and KI (0.6 g, 3.3 mmol, 0.1 eq.) in acetone (600 mL) was stirred during 30 hours at 65° C. The reaction mixture was filtered over Celite and the solvent was evaporated. The resulting crude product was diluted in dichloromethane (200 mL) and washed twice with an aqueous saturated solution of NaHCO$_3$ and with brine. After drying over MgSO$_4$, filtration and evaporation of the solvent, the crude product was purified by chromatography over silica gel column (dichloromethane/methanol 98/2 to 95/5) to afford 3 as a colorless oil in 75% yield. $^1$H NMR (300 MHz, CDCl$_3$) δ 7.48 (d, J=7.7 Hz, 2H, Ar$^2$-2,6-H), 7.28 (m, 5H, Ar$^2$-3,4,5-H and Ar$^1$-2,6-H), 5.12 (s, 2H, Ar$^2$OCH$_2$), 4.20-4.17 (t, J=4.8 Hz, 4H, Ar$^1$OCH$_2$), 3.90 (s, 3H, COOCH$_3$), 3.88-3.85 (t, J=4.8 Hz, 4H, OCH$_2$CH$_2$O), 3.74-3.69 (m, 4H, OCH$_2$CH$_2$O), 3.67-3.60 (m, 16H, OCH$_2$CH$_2$O), 3.54-3.50 (m, 4H, OCH$_2$CH$_2$O), 3.35 (s, 6H, OCH$_2$CH$_2$OCH$_3$); $^{13}$C NMR (75 MHz, CDCl$_3$) δ 166.9, 152.5, 142.2, 138.2, 128.2, 128.0, 127.8, 125.3, 109.1, 74.8, 72.3, 71.2, 71.0, 70.9, 70.8, 70.0, 69.2, 59.3, 52.5. MALDI: calculated for C$_{33}$H$_{50}$NaO$_{13}$: 677.33. obtained: 677.03.

Compound 4:

To a solution of compound 3 (8.3 g, 12.7 mmol) in a mixture methanol/water 4/1 (150 mL) was added of sodium hydroxyde (5.1 g, 127.0 mmol, 10 eq.). The reaction mixture was stirred 2h at 85° C. and stopped. The mixture was concentrated in vacuo and hydrolyzed (200 mL). The pH was adjusted at 3 by HCl 12N and the aqueous solution was extracted with dichloromethane (3×100 mL). The combined organic phase was washed with brine and water, dried over MgSO$_4$, filtered and concentrated under reduced pressure purified by column chromatography on silica gel eluting with dichloromethane/methanol (95/5) to afford 4 as a colorless oil in 90% yield. $^1$H NMR (300 MHz, CDCl$_3$) δ 7.50 (d, J=7.8 Hz, 2H, Ar$^2$-2,6-H), 7.38 (s, 2H, Ar$^1$-2,6-H), 7.35-7.28 (m, 3H, Ar$^2$-3,4,5-H), 5.13 (s, 2H, Ar$^2$OCH$_2$), 4.20-4.16 (t, J=4.8 Hz, 4H, Ar$^1$OCH$_2$), 3.87-3.82 (t, J=4.8 Hz, 4H, OCH$_2$CH$_2$O), 3.74-3.69 (m, 4H, OCH$_2$CH$_2$O), 3.67-3.61 (m, 16H, OCH$_2$CH$_2$O), 3.54-3.50 (m, 4H, OCH$_2$CH$_2$O), 3.37 (s, 6H, OCH$_2$CH$_2$OCH$_3$); $^{13}$C NMR (75 MHz, CDCl$_3$) δ 169.3, 152.8, 138.2, 142.4, 128.2, 128.0, 127.8, 125.3, 109.2, 74.8, 72.3, 71.2, 71.0, 70.9, 70.8, 70.0, 69.2, 52.5. MALDI: calculated for C$_{32}$H$_{48}$O$_{13}$: 640.31. obtained: 640.24. calculated for C$_{29}$H$_{48}$NaO$_{13}$: 627.30. obtained: 627.13; calculated for C$_{29}$H$_{48}$KO$_{13}$: 643.27. obtained: 643.09.

Scheme 2.

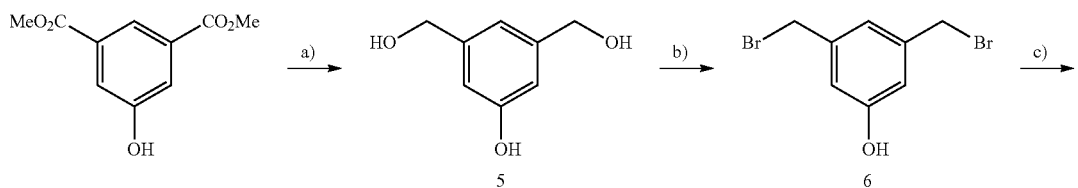

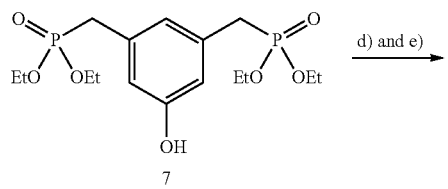

-continued
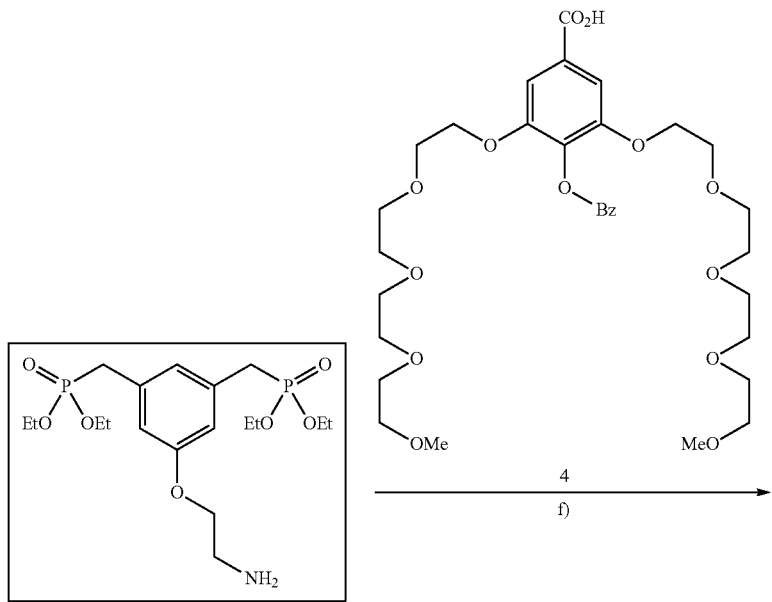
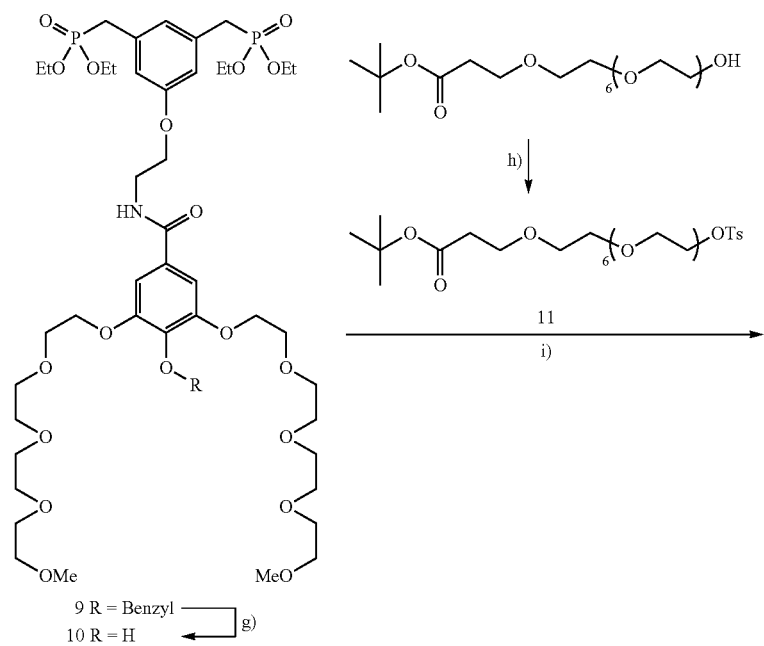

-continued

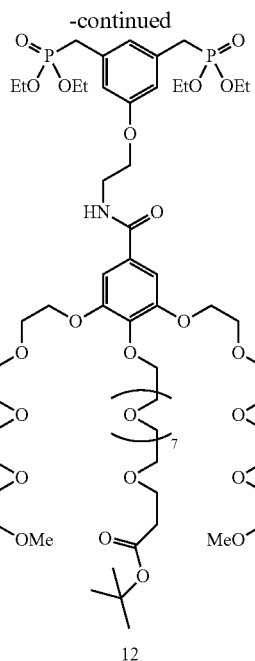

12

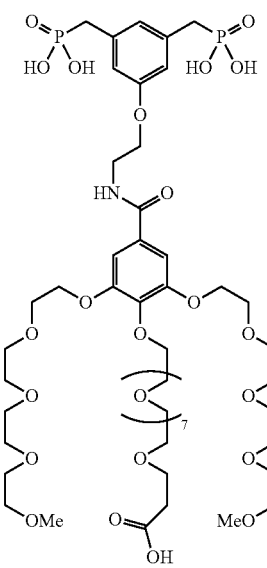

13 a) LiAlH₄ 1M in THF, THF, reflux, 3 h; b) HBr in acetic acid 30%, Acetic acid, RT, 24 h; c) P(OEt)₃, 160° C., 3 h; d) Boc-2-bromoethylamine, K₂CO₃, KI, acetone, reflux, 16 h; e) TFA, CH₂Cl₂, 0° C. at RT, overnight; f) compound 4, BOP, DIPEA, CH₂Cl₂, RT, 24 h; g) Pd activated on Carbon 10%, H₂, EtOH, RT, overnight; h) TsCl, NEt₃, CH₂Cl₂, RT, 24 h; i) compound 11, K₂CO₃, KI, acetone, reflux, 16 h; j) TMSBr, CH₂Cl₂, RT, overnight.

Compound 5:

4.20 g of dimethyl 5-hydroxyisophtalate (20.0 mmol) were dissolved in 21 mL of anhydrous THF. Then, a LiAlH₄ solution, 0.5 M in THF (36.0 mmol, 1.8 eq.) was added dropwise at 0° C. After refluxing during 3 hours, the mixture was cooled to room temperature and acidified with 30 mL of a solution of H₂SO₄ 10%. The THF was evaporated under vacuum and the resulting aqueous phase was extracted several times (at least 6 times, TLC control) with ethyl acetate. The organic phase was dried over MgSO₄, filtered and concentrated under reduced pressure to afford 5 as a white solid in 94% yield. $^1$H NMR (300 MHz, CD₃OD-d) δ 6.82 (s, 1H, Ar-4-H), 6.71 (s, 2H, Ar-2,6-H), 4.52 (d, J=5.8 Hz, 4H, ArCH₂OH); $^{13}$C NMR (75 MHz, CD₃OD-d) δ 157.2, 143.7, 115.1, 111.6, 63.0.

Compound 6:

2.00 g of 5 (13.0 mmol) were dissolved in 21 ml, of acetic acid. Then, a solution of HBr 30% in acetic acid (36.0 mmol, 1.8 eq.) was added dropwise at 0° C. The mixture was stirred 24 h at room temperature, and then 80 mL of distilled water were added. A white precipitate formed and the mixture was stirred 10 minutes more. The resulting aqueous phase was extracted 3 times with 200 mL dichloromethane and the organic layer was washed twice with 120 ml, of distilled water, twice with 120 mL of a saturated solution of sodium hydrogenocarbonate, and 80 ml, of brine. The organic phase was dried over MgSO₄, filtered and concentrated under reduced pressure to afford 6 as a white solid in 96% yield. $^1$H NMR (300 MHz, CDCl₃) δ 6.99 (t, J=1.3 Hz, 1H, Ar-4-H), 6.04 (d, J=1.3 Hz, 2H, Ar-2,6-H), 5.38 (br s, 1H, OH), 4.40 (s, 4H, ArCH₂Br); $^{13}$C NMR (75 MHz, CDCl₃) δ 155.8, 140.0, 122.2, 116.2, 32.7.

Compound 7:

A solution of 6 (2.24 g, 8.0 mmol) in 5.0 mL of P(OEt)₃ (4.0 eq.), was stirred during 2 hours at 160° C. The excess of P(OEt)₃ was evaporated under reduced pressure at 70° C. The crude product was purified by chromatography over silica gel column (dichloromethane/methanol 95/5) to afford 7 as a white solid in 95% yield. $^1$H NMR (300 MHz, CDCl₃) δ 6.82 (bs, 2H, Ar-2.6-H), 6.62 (bs, 1H, Ar-4-H), 3.99 (m, 8H, PO(OCH₂CH₃)₂), 3.49 (d, J=21.9 Hz, 4H, ArCH₂P), 1.23 (t, J=7.1 Hz, 12H, PO(OCH₂CH₃)₂); $^{13}$C NMR (75 MHz, CDCl₃) δ 157.9, 132.6 (J=10.6 Hz), 122.4 (J=6.7 Hz), 115.8, 62.5 (J=6.6 Hz), 33.6 (J=138.8 Hz), 16.5 (J=5.2 Hz); $^{31}$P NMR (81 MHz, CDCl₃) δ 26.72. MALDI: calculated for C₁₆H₂₉O₇P₂: 395.138. obtained: 394.963.

Compound 8:

To a solution of 7 (1.5 g, 3.8 mmol) in acetone (40 mL) were added (2-bromo-ethyl)carbamic acid tert-butyl ester (1.1 g, 4.95 mmol, 1.3 eq.), K₂CO₃ (2.1 g, 15.2 mmol, 4 eq.) and KI (0.1 g, 0.4 mmol, 0.1 eq.). The mixture was stirred during 48 h at 65° C., filtered over Celite and evaporated under reduced pressure. The resulting crude product was diluted in dichloromethane (100 mL) and washed twice with an aqueous saturated solution of NaHCO₃ and with brine. After drying over MgSO₄, filtration and evaporation of the solvent, the crude product was purified by chromatography over silica gel column (dichloromethane/methanol 98/2 to 95/5) to afford (Boc-amino) derivative as white solid (76%). This compound (1.2 g, 2.2 mmol) was dissolved in 30 mL of CH₂Cl₂ anhydre at 0° C. and trifluoroacetic acid was added dropwise 2 mL (22.0 mmol, 10.0 eq.). The reaction mixture was stirred overnight at room temperature, then the volatiles were evaporated. The crude product was dissolved in dichloromethane (20 mL) and was washed with NaOH 1N (2×10 mL). The organic layer was dried over MgSO₄, filtered and concentrated under reduced pressure to afford 8 as a white solid in 88% yield and used without further purification. $^1$H NMR (300 MHz, CDCl₃) δ 6.72 (m, 3H, Ar-2,4,6-H), 5.25 (br s, 2H, OCH₂CH₂NH₂), 4.03-3.92 (m, 10H, PO(OCH$_2$CH$_3$)$_2$ and OCH$_2$CH$_2$NH), 3.10 (d, J=21.7 Hz, 4H, ArCH$_2$P), 3.02 (m, 2H, OCH$_2$CH$_2$NH), 1.25 (t, J=7.1 Hz, 12H, PO(OCH$_2$CH$_3$)$_2$); $^{13}$C NMR (75 MHz, CDCl$_3$) δ 159.0 (J=2.8 Hz), 133.1 (J=6.0 Hz), 123.8 (J=6.8 Hz), 114.5 (J=5.0 Hz), 70.0, 62.1 (J=7.0 Hz), 41.5, 33.5 (J=138.2 Hz), 16.5 (J=2.7 Hz); $^{31}$P NMR (81 MHz, CDCl$_3$) δ 26.24. MALDI: calculated for C$_{18}$H$_{34}$NO$_7$P$_2$: 438.17. obtained: 438.18. calculated for C$_{18}$H$_{34}$NaO$_7$P$_2$: 460.17. obtained: 460.16.

Compound 9:

To a solution of carboxylic acid derivative 4 (1.45 g, 2.05 mmol, 1.0 eq.) in 30 mL of distilled dichloromethane was added, under argon, coupling reagent BOP (1.2 g, 2.68 mmol, 1.3 eq.).

After 5 min, were added amine derivative 8 (0.9 g, 2.05 mmol 1.0 eq.) and N,N-diisopropylethylamine (1.0 mL, 6.8 mmol, 3 eq.). The reaction mixture was stirred overnight at room temperature. 50 mL of dichloromethane was added and the organic layer was washed with a solution of sodium hydroxyde 1N (2×30 mL), HCl 1N (2×30 mL), brine (2×30 mL) and water (1×30 mL), dried over MgSO4, filtered and concentrated under reduced pressure. The crude product was purified by chromatography over silica gel column (dichloromethane/methanol 98/2 to 95/5) to afford compound 9 as colorless oil in 87% of yield. $^1$H NMR (300 MHz, CDCl$_3$) δ 7.50 (d, J=7.7 Hz, 2H, Ar$^3$-2,6-H), 7.35-7.28 (m, 3H, Ar$^3$-3,4,5-H), 7.07 (s, 2H, Ar$^2$-2,6-H), 6.88 (t, J=5.7 Hz, 1H, OCH$_2$CH$_2$NH), 6.85-6.78 (m, 3H, Ar$^1$-2,4,6-H), 5.07 (s, 2H, Ar$^3$OCH$_2$), 4.20-4.17 (t, J=4.8 Hz, 4H, Ar$^2$OCH$_2$), 4.15-4.11 (t, J=5.0 Hz, 2H, OCH$_2$CH$_2$NH), 4.08-3.96 (m, 8H, PO(OCH$_2$CH$_3$)$_2$), 3.88-3.78 (m, 6H, OCH$_2$CH$_2$NH and OCH$_2$CH$_2$O), 3.71-3.68 (m, 4H, OCH$_2$CH$_2$O), 3.65-3.58 (m, 16H, OCH$_2$CH$_2$O), 3.55-3.49 (m, 4H, OCH$_2$CH$_2$O), 3.35 (s, 6H, OCH$_2$CH$_2$OCH$_3$), 3.08 (d, J=21.5 Hz, 4H, Ar$^1$CH$_2$P), 1.25 (t, J=7.0 Hz, 12H); $^{13}$C NMR (75 MHz, CDCl$_3$) δ 167.2, 158.6 (J=2.8 Hz), 152.8, 141.0, 137.8, 133.1 (J=6.0 Hz), 129.6, 128.2, 128.0, 127.8, 124.0 (J=6.8 Hz), 114.6 (J=4.8 Hz), 107.0, 74.9, 72.0, 70.8, 70.7, 70.6, 69.8, 69.1, 66.8, 62.1 (J=3.4 Hz), 58.9, 53.2, 39.5, 36.8 (J=3.9 Hz), 33.5 (J=138.3 Hz), 16.5=2.7 Hz); $^{31}$P NMR (81 MHz, CDCl$_3$) δ 26.08. MALDI: calculated for C$_{50}$H$_{79}$NaNO$_{19}$P$_2$: 1082.87. obtained: 1082.51.

Compound 10:

The benzylated compound 9 (2 g, 1.9 mmol) was dissolved in ethanol absolute (20 mL) and palladium activated on carbon 10% (0.5 eq.) was added. The mixture was stirred under hydrogen atmosphere at room temperature for 16 h. The product was filtered through a plug of Celite before being concentrated and purified by column chromatography on silica gel eluting with dichloromethane/methanol (98/2 to 90/10) to afford 10 as colorless oil in 87% of yield. $^1$H NMR (300 MHz, CDCl$_3$) δ 7.16 (s, 2H, Ar$^2$-2,6-H), 6.85-6.78 (m, 3H, Ar$^1$-2,4,6-H), 6.65 (m, 1H, OCH$_2$CH$_2$NH), 4.27-4.21 (t, J=4.7 Hz, 4H, Ar$^2$OCH$_2$), 4.15-4.10 (t, J=5.0 Hz, 2H, OCH$_2$CH$_2$NH), 4.08-3.98 (m, 8H, PO(OCH$_2$CH$_3$)$_2$), 3.88-3.78 (m, 6H, OCH$_2$CH$_2$NH and OCH$_2$CH$_2$O), 3.75-3.60 (m, 20H, OCH$_2$CH$_2$O), 3.56-3.51 (m, 4H, OCH$_2$CH$_2$O), 3.35 (s, 6H, OCH$_2$CH$_2$OCH$_3$), 3.09 (d, J=22.0 Hz, 4H, Ar$^1$CH$_2$P), 1.26 (t, J=7.1 Hz, 12H, PO(OCH$_2$CH$_3$)$_2$); $^{13}$C NMR (75 MHz, CDCl$_3$) δ 167.3, 158.7 (J=2.8 Hz), 146.8, 141.0, 133.1 (J=6.0 Hz), 124.0, 114.6, 108.4, 72.0, 70.8, 70.7, 70.6, 69.8, 69.1, 66.8, 62.1 (J=3.4 Hz), 58.9, 39.5, 33.4 (J=138.1 Hz), 16.4 (J=2.7 Hz); $^{31}$P NMR (81 MHz, CDCl$_3$) δ 26.10. MALDI: calculated for C$_{43}$H$_{74}$NO$_{19}$P$_2$: 970.43. obtained: 970.44. calculated for C$_{43}$H$_{73}$NaNO$_{19}$P$_2$: 992.43. obtained: 992.44.

Compound 11:

To a solution of Hydroxy-dPEG™$_8$-t-butyl ester (1.00 g, 2.0 mmol) in 20 mL of CH$_2$Cl$_2$ at 0° C. are added sequentially 840 mL (6.0 mmol, 3.0 eq.) of NEt$_3$ and 570 mg (3.0 mmol, 1.5 eq.) of para-toluenesulfonyl chloride. After 40 h stirring at room temperature, the reaction mixture is diluted with 70 mL of CH$_2$Cl$_2$. The organic phases are combined, washed with brine, dried over MgSO4, filtered and concentrated under reduced pressure. The crude product is purified by chromatography over silica gel column (ethyl acetate/methanol 95/5 to 90/10) to afford 11 as a colorless oil in 70% yield. $^1$H NMR (300 MHz, CDCl$_3$): δ (ppm) 1.44 (s, 9H), 2.45 (s, 3H), 2.50 (t, 2H, $_3$J=6.6 Hz), 3.58-3.73 (m, 32H), 4.16 (t, 2H, $_3$J=4.9 Hz), 7.34 (2H, AA' part of an AA'BB' system), 7.81 (2H, BB' part of an AA'BB' system). $^{13}$C NMR (75 MHz, CDCl$_3$): δ (ppm) 21.14, 27.65, 35.84, 66.40, 68.15, 69.00, 70.08, 79.78, 127.46, 129.47, 132.74, 144.32, 170.20. MALDI: calculated for C10H20LiO5: 227.15. obtained: 227.08. calculated for C26H44LiO12S: 587.27. obtained: 587.13.

Compound 12:

To an equimolar solution of phenolic derivative 10 (0.3 g, 0.31 mmol) and compound 11 (0.20 g, 0.31 mmol) in 10 mL of acetone were added K$_2$CO$_3$ (0.13 g, 0.93 mmol, 3 eq.) and KI (18 mg, 0.11 mmol, 0.3 eq.). The reaction mixture was stirred at 60° C. during 24 h. After filtration over Celite, the solvent was evaporated and the residue was diluted in dichloromethane (50 mL). The organic layer was washed twice with a saturated solution of NaHCO$_3$, then with brine, filtered and concentrated under reduced pressure. The crude product was purified by column chromatography on silica gel eluting with dichloromethane/methanol (98/2 to 90/10) to afford compound 12 as a colorless oil in 90% yield after purification. $^1$H NMR (300 MHz, CDCl$_3$) δ 7.10 (s, 2H, Ar$^2$-2,6-H), 6.87 (t, J=5.1 Hz, 1H, Ar$^1$OCH$_2$CH$_2$NH), 6.80 (t, 1H, J=2.0 Hz, Ar'-2'-H), 6.76 (q, 2H, J=2.0 Hz, Ar$^1$-4,6-H), 4.22-4.15 (m, 6H, Ar$^2$OCH$_2$CH$_2$O), 4.12 (t, 2H, J=5.1 Hz, Ar$^1$OCH$_2$CH$_2$NH), 4.05-3.95 (m, 8H, J=7.0 Hz, PO(OCH$_2$CH$_3$)$_2$), 3.85-3.75 (m, 8H, Ar$^1$OCH$_2$CH$_2$NH and OCH$_2$CH$_2$O), 3.70-3.50 (m, 54H, OCH$_2$CH$_2$O), 3.33 (s, 6H, OCH$_2$CH$_2$OCH$_3$), 3.07 (d, J=21.7 Hz, 4H, Ar$^1$CH$_2$P), 2.48 (t, 2H, J=6.6 Hz, Ar$^2$OCH$_2$CH$_2$COOC(CH$_3$)$_3$), 1.42 (s, 9H, Ar$^2$OCH$_2$CH$_2$COOC(CH$_3$)$_3$), 1.22 (t, J=7.0 Hz, 12H, PO(OCH$_2$CH$_3$)$_2$); $^{13}$C NMR (75 MHz, CDCl$_3$) 170.9, 167.1, 157.5, 152.4, 141.6, 133.2 (J=6.0 Hz), 129.4, 124.1, 114.6 (J=5.0 Hz), 107.3, 80.4, 72.2, 71.9, 70.7, 70.6, 70.5, 70.55, 70.4, 70.3, 69.7, 69.1, 66.8, 66.6, 62.1 (J=7.0 Hz), 58.9, 39.6, 36.1, 33.8 (J=137.8 Hz), 27.9, 16.4 (J=6.0 Hz); $^{31}$P NMR (81 MHz, CDCl$_3$) δ 26.06. MALDI: calculated for C$_{66}$H$_{117}$NaNO$_{29}$P$_2$: 1472.72. obtained: 1472.65.

Compound 13:

To a solution of ethyl phosphonate derivatives 12 (0.2 g, 0.14 mmol) in 5 mL of distillated dichloromethane at 0° C., was added dropwise 0.55 mL of TMSBr (3 mmol, 30 eq.). After stirring overnight at room temperature, the volatiles were evaporated and methanol is added to the crude product and evaporated several times. The phosphonic acid 13 was obtained as an orange oil in 94% yield without further purification. $^1$H NMR (300 MHz, CD$_3$OD) δ 7.28 (s, 2H, Ar$^2$-2,6-H), 6.92-6.86 (m, 3H, Ar'-2,4,6-H), 4.35-4.20 (m, 8H, Ar$^2$OCH$_2$CH$_2$O and Ar$^1$OCH$_2$CH$_2$NH), 3.92-3.82 (m, 8H, Ar$^1$OCH$_2$CH$_2$NH and OCH$_2$CH$_2$O), 3.80-3.53 (m, 54H, OCH$_2$CH$_2$O), 3.38 (s, 6H, OCH$_2$CH$_2$OCH$_3$), 3.18 (d, J=21.8 Hz, 4H, Ar$^1$CH$_2$P), 2.62 (t, 2H, J=6.0 Hz, Ar$^2$OCH$_2$CH$_2$COOH); $^{13}$C NMR (75 MHz, CD$_3$OD) δ 172.2, 167.1, 158.8, 152.3, 141.0, 134.8 (J=6.0 Hz), 128.8, 123.8, 114.3, 106.4, 72.2, 71.7, 70.4, 70.25, 70.15, 70.1, 70.0, 69.95, 69.4, 68.8, 66.3, 66.1, 60.8, 57.8, 50.8, 39.6, 34.6, 33.6 (J=134.5 Hz); $^{31}$P NMR (81 MHz, CD$_3$OD) δ 25.19. MALDI: calculated for C$_{54}$H$_{94}$NO$_{29}$P$_2$: 1282.53. obtained: 1282.46. calculated for C$_{54}$H$_{93}$NaNO$_{29}$P$_2$: 1304.53. obtained: 1304.45.

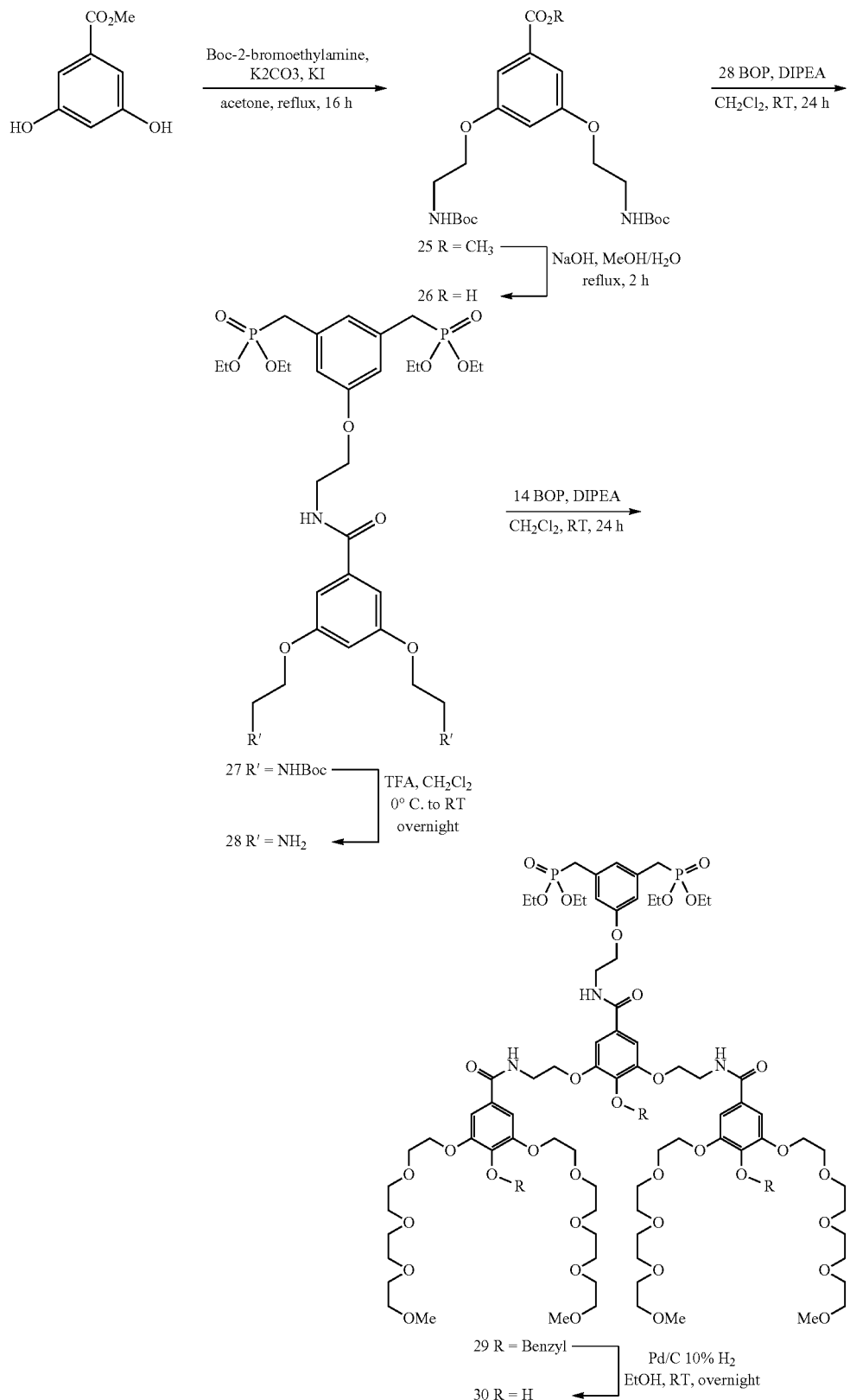
Compound 25:
Compound 25 was obtained by the same procedure used for 8. Starting from 3,5-dihydroxybenzoic methyl ester (0.7 g, 4.3 mmol), a white foam was synthesized after purification by chromatography over silica gel column (dichloromethane/methanol 98/2 to 95/5) (65% of yield). $^1$H NMR (300 MHz, CDCl$_3$) 7.18 (d, J=2.5 Hz, 2H, Ar-2,6-H), 6.65 (t, J=2.4 Hz, 1H, Ar-4-H), 4.98 (m, 2H, OCH$_2$CH$_2$NH), 4.04 (t, J=5.0 Hz, 4H, OCH$_2$CH$_2$NH), 3.91 (s, 3H, COOCH$_3$), 3.56 (m, 4H, OCH$_2$CH$_2$NH), 1.45 (s, 18H, COOC(CH$_3$)); $^{13}$C NMR (75 MHz, CDCl$_3$) δ 166.9, 152.8, 142.4, 134.7, 125.3, 117.9, 109.2, 74.3, 72.3, 71.2, 71.0, 70.9, 70.8, 70.0, 69.2, 59.3, 52.5. MALDI: calculated for C$_{22}$H$_{34}$N$_2$O$_8$: 454.23. obtained: 454.02. calculated for C$_{29}$H$_{48}$NaO$_{13}$: 627.30. obtained: 627.13. calculated for C$_{29}$H$_{48}$KO$_{13}$: 643.27. obtained: 643.09.

Compound 26:

Compound 26 was obtained by the same procedure used for 4. Starting from 25 (0.75 g, 1.7 mmol), a white foam was synthesized, which was used without further purification (86% of yield). $^1$H NMR (300 MHz, CDCl$_3$) δ 7.22 (s, 2H, Ar-2,6-H), 6.62 (s, 1H, Ar-4-H), 5.02 (m, 2H, OCH$_2$CH$_2$NH), 4.03 (t, J=4.8 Hz, 4H, OCH$_2$CH$_2$NH), 3.52 (m, 4H, OCH$_2$CH$_2$NH), 1.48 (s, 18H, COOC(CH$_3$)); $^{13}$C NMR (75 MHz, CDCl$_3$) δ 166.9, 152.8, 142.4, 134.7, 125.3, 117.9, 109.2, 74.3, 72.3, 71.2, 71.0, 70.9, 70.8, 70.0, 69.2, 59.3, 52.5. MALDI: calculated for C$_{21}$H$_{32}$N$_2$O$_8$: 440.22. obtained: 440.02; calculated for C$_{29}$H$_{48}$NaO$_{13}$: 30. obtained: 627.13. calculated for C$_{29}$H$_{48}$KO$_{13}$: 643.27. obtained: 643.09.

Compound 27:

To an equimolar solution of carboxylic acid derivative 26 (0.4 g, 0.9 mmol) in dichloromethane anhydre (20 mL) was added under argon coupling reagent BOP (0.5 g, 1.2 mmol, 1.3 eq.). After 5 min, were added the amine derivative 8 (0.4 g, 0.9 mmol) and diisopropylethylamine (0.45 mL, 2.7 mmol, 3 eq.). The reaction mixture was stirred overnight at room temperature. 20 mL of dichloromethane were added and the organic layer was washed with a solution of NaOH 1N (2×20 mL), HCl 1N (2×20 mL), brine (2×20 mL) and water (2×20 mL), dried over MgSO$_4$, filtered and concentrated under reduced pressure. The crude product was purified by chromatography over silica gel column (dichloromethane/methanol 98/2 to 95/5) to afford 27 as a colorless oil in 65% of yield. $^1$H NMR (300 MHz, CDCl$_3$) δ 6.95 (d, J=2.4 Hz, 2H, Ar$^1$-2,6-H), 6.85-6.78 (m, 3H, Ar$^2$-2,4,6-H), 6.69 (t, J=2.4 Hz, 1H, Ar$^1$-4H), 6.57 (t, J=2.0 Hz, 1H, Ar$^1$OCH$_2$CH$_2$NH), 5.02 (m, 2H, Ar$^2$OCH$_2$CH$_2$NH), 4.13 (t, J=5.0 Hz, 2H, Ar$^1$OCH$_2$CH$_2$NH), 4.07-3.97 (m, 12H, Ar$^2$OCH$_2$CH$_2$NH and PO(OCH$_2$CH$_3$)$_2$), 3.82 (q, J=5.0 Hz, 2H, Ar$^1$OCH$_2$CH$_2$NH), 3.55-3.50 (m, 4H, Ar$^2$OCH$_2$CH$_2$NH), 3.08 (d, J=22.0 Hz, 4H, Ar$^1$CH$_2$P), 1.42 (s, 18H, COOC(CH$_3$)); 1.25 (t, J=7.0 Hz, 12H, PO(OCH$_2$CH$_3$)$_2$); $^{13}$C NMR (75 MHz, CDCl$_3$) δ 167.2, 159.8, 158.5, 155.8, 136.8, 133.1 (J=6.0 Hz), 124.0, 114.8 (J=4.5 Hz), 106.0, 104.7, 67.5, 66.8, 62.3 (J=3.4 Hz), 39.5, 36.8 (J=4.0 Hz), 33.4 (J=138.0 Hz), 16.4 (J=2.7 Hz); $^{31}$P NMR (81 MHz, CDCl$_3$) 26.10. MALDI: calculated for C$_{39}$H$_{63}$N$_3$O$_{14}$P$_2$: 859.38. obtained: 859.10. calculated for C$_{29}$H$_{53}$NaO$_{14}$P: 679.31. obtained: 679.24.

Compound 28:

To a solution of 27 (0.4 g, 0.4 mmol) in 15 mL of CH$_2$Cl$_2$ at 0° C. was added dropwise 780 μL (8.0 mmol, 20.0 eq.) of trifluoroacetic acid. The reaction mixture was stirred overnight at room temperature, then the volatiles were evaporated. The crude product was kept under the form of its difluoroacetate salt and 28 was obtained as a white solid in 98% yield and used without further purification. $^1$H NMR (300 MHz, CDCl$_3$) δ 8.74 (m, 1H, Ar$^1$OCH$_2$CH$_2$NH), 8.55 (m, 4H, Ar$^2$OCH$_2$CH$_2$NH$_2$), 6.95 (m, 2H, Ar$^1$-2,6-H), 6.85-6.78 (m, 3H, Ar$^2$-2,4,6-H), 6.69 (m, 1H, Ar$^1$-4-H), 4.21 (m, 2H, Ar$^1$OCH$_2$CH$_2$NH), 4.05-3.90 (m, 12H, Ar$^2$OCH$_2$CH$_2$NH and PO(OCH$_2$CH$_3$)$_2$), 3.78 (m, 2H, Ar$^1$OCH$_2$CH$_2$NH), 3.58-3.50 (m, 4H, Ar$^2$OCH$_2$CH$_2$NH), 3.08 (m, 4H, Ar$^1$CH$_2$P), 1.25 (t, J=7.0 Hz, 12H, PO(OCH$_2$CH$_3$)$_2$); $^{13}$C NMR (75 MHz, CDCl$_3$) 166.9, 152.8, 142.4, 134.7, 125.3, 117.9, 109.2, 74.3, 72.3, 71.2, 71.0, 70.9, 70.8, 70.0, 69.2, 59.3, 52.5; $^{31}$P NMR (81 MHz, CDCl$_3$) δ 26.60. MALDI: calculated for C$_{29}$H$_{47}$N$_3$O$_{14}$P$_2$: 659.27. obtained: 659.02. calculated for C$_{29}$H$_{53}$NaO$_{14}$P: 679.31. obtained: 679.24.

Compound 29:

Compound 29 was obtained by the same procedure used for 9. Starting from 28 (0.40 g, 0.45 mmol), a colorless oil was synthesized after purification by chromatography over silica gel column (dichloromethane/methanol 98/2 to 95/5) (70%). $^1$H NMR (300 MHz, CDCl$_3$) δ 7.50 (d, J=7.7 Hz, 2H, Ar$^3$-2,6-H), 7.35-7.28 (m, 3H, Ar$^3$-3,4,5-H), 7.11 (s, 4H, Ar$^2$-2,6-H), 7.05 (t, J=5.0 Hz, 2H, Ar$^2$OCH$_2$CH$_2$NH), 6.95 (d, J=2.3 Hz, 2H, Ar$^1$-2,6-H), 6.69 (t, J=2.4 Hz, 1H, Ar$^1$-4-H), 6.82-6.78 (m, 3H, Ar$^2$-2,4,6-H), 6.64 (t, J=1.9 Hz, 1H, Ar$^1$OCH$_2$CH$_2$NH), 5.07 (s, 4H, Ar$^3$OCH$_2$), 4.20-4.17 (m, 14H, Ar$^2$OCH$_2$CH$_2$O, Ar$^1$OCH$_2$CH$_2$NH and Ar$^2$OCH$_2$CH$_2$NH), 4.08-3.96 (m, 8H, PO(OCH$_2$CH$_3$)$_2$), 3.83-3.78 (m, 14H, Ar$^1$OCH$_2$CH$_2$NH, Ar$^2$OCH$_2$CH$_2$NH and OCH$_2$CH$_2$O), 3.65-3.55 (m, 34H, OCH$_2$CH$_2$O), 3.55-3.48 (m, 8H, OCH$_2$CH$_2$O), 3.34 (s, 12H, OCH$_2$CH$_2$OCH$_3$), 3.08 (d, J=22.0 Hz, 4H, Ar$^1$CH$_2$P), 1.23 (t, J=7.0 Hz, 12H, PO(OCH$_2$CH$_3$)$_2$); $^{13}$C NMR (75 MHz, CDCl$_3$) 167.2, 159.8, 152.5, 141.0, 137.8, 136.5, 133.1 (J=6.0 Hz), 129.5, 128.2, 128.0, 127.8, 124.0, 114.8 (J=4.8 Hz), 107.8, 107.0, 106.0, 74.9, 72.0, 70.8, 70.7, 70.6, 69.8, 69.1, 66.8, 62.1 (J=3.4 Hz), 58.9, 39.5, 35.2, 33.3 (J=138.0 Hz), 16.4 (J=2.7 Hz); $^{31}$P NMR (81 MHz, CDCl$_3$) δ 26.60. MALDI: calculated for C$_{93}$H$_{169}$N$_3$O$_{34}$P$_2$: 1903.87. obtained: 1903.52; calculated for C$_{29}$H$_{53}$NaO$_{14}$P: 679.31. obtained: 679.24.

Compound 30:

Compound 30 was obtained by the same procedure used for 10. Starting from 29 (0.65 g, 0.34 mmol), a colorless oil was obtained after purification by chromatography over silica gel column (dichloromethane/methanol 98/2 to 95/5) (76%). $^1$H NMR (300 MHz, CDCl$_3$) δ 7.62 (br s, 2H, Ar$^2$OH), 7.20 (s, 4H, Ar$^2$-2,6-H), 7.11 (t, J=5.5 Hz, 2H, Ar$^2$OCH$_2$CH$_2$NH), 6.96 (d, J=1.7 Hz, 2H, Ar$^1$-2,6-H), 6.80-6.74 (m, 3H, Ar$^2$-2,4,6-H), 6.55 (t, J=1.9 Hz, 1H, Ar$^1$-4-H), 6.44 (t, J=1.9 Hz, 1H, Ar$^1$OCH$_2$CH$_2$NH), 4.17 (t, J=4.8 Hz, 8H, Ar$^2$OCH$_2$), 4.11 (t, J=4.6 Hz, 6H, Ar$^1$OCH$_2$CH$_2$NH and Ar$^2$OCH$_2$CH$_2$NH), 4.05-3.93 (m, 8H, PO(OCH$_2$CH$_3$)$_2$), 3.83-3.75 (m, 14H, Ar$^1$OCH$_2$CH$_2$NH, Ar$^2$OCH$_2$CH$_2$NH and OCH$_2$CH$_2$O), 3.70-3.60 (m, 34H, OCH$_2$CH$_2$O), 3.52-3.48 (m, 8H, OCH$_2$CH$_2$O), 3.34 (s, 12H, OCH$_2$CH$_2$OCH$_3$), 3.06 (d, J=22.0 Hz, 4H, Ar$^1$CH$_2$P), 1.21 (t, J=7.0 Hz, 12H, PO(OCH$_2$CH$_3$)$_2$); $^{13}$C NMR (75 MHz, CDCl$_3$) δ 167.2, 159.8, 152.5, 140.8, 136.5, 133.1 (J=6.0 Hz), 129.5, 124.5, 114.8 (J=4.8 Hz), 108.7, 106.0, 104.8, 71.9, 70.8, 70.7, 70.6, 69.8, 69.1, 66.8, 62.1 (J=7.0 Hz), 58.9, 39.5, 35.2, 33.4 (J=137.5 Hz), 16.3 (J=2.7 Hz); $^{31}$P NMR (81 MHz, CDCl$_3$) δ 26.60. MALDI: calculated for C$_{79}$H$_{127}$N$_3$O$_{34}$P$_2$: 1723.78. obtained: 1723.46. calculated for C$_{29}$H$_{53}$NaO$_{14}$P: 679.31. obtained: 679.24.

Example 17: Grafting of Dendrons at the Surface of Nanoparticles Whatever their Form or Composition The as synthesized nanoparticles are coated with surfactants and stable in suspension in an organic solvent. Then the molecules may be grafted at the surface of nanoparticles either by a ligand exchange and phase transfer process in water or by direct grafting in the organic solvent and then transfer of the so functionalized NPs in water.

For the dendrons which bear functional bioactive groups such as vectors or fluorescent molecules or peptides . . . the dendron bearing these functions may be directly grafted at the surface of nanoparticles or a mall dendron bearing a functional group allowing a further coupling of the bioactive molecules is grafted at the surface of NPs and then a coupling reaction is induced to couple the bioactive molecules at the surface of NPs.

Example 18: Functionalization Process by Ligand Exchange in Organic Solvents 30 ml of a NP@ligands suspension in chloroforme/THF (1 mg/ml) were put into contact with an excess of dendron molecules bearing different anchoring function (phosphonate or carboxylate). Organic suspensions were magnetically stirred for one night. A ligand exchange occurs leading to suspensions of dendronized NPs. The amount of molecules which is added is the amount necessary to coat all the surface of NPs+40% in weight.

Example 19: Functionalization Process by Ligand Exchange and Phase Transfer 10 ml of a NP@ligands suspension in hexane (1 mg/ml) were put in contact with a suspension (13 mg of molecules, 5 ml water and 2 ml methanol) of the dendron, at a pH which depend on the functional group beared by the dendron (pH=5 for dendron bearing bearing no functional group and pH 3.5 for dendrons bearing a carboxylic acid function at its periphery with a pKa value around 4). Both immiscible suspensions were magnetically stirred for one night. A ligand exchange and a phase transfer process led to an aqueous suspension of dendronized NPs.

The grafted NPs were then separated from the ungrafted dendrons by ultrafiltration. This technique, well adapted to purify all functionalized aqueous NPs suspensions, involves regenerated cellulose membranes with a nominal molecular weight limit (NMWL) of 30 kDa. After at least 4 purification steps by ultrafiltration, the pH of the NPs suspension was 6.

To coat the nanoparticles with different types of dendrons, a mixture of dendrons is added instead of one type of dendron: tests have to be conducted by varying the proportion of each dendron to reach the good grafting rate of each dendron.

Example 20: Functionalization Process by Ligand Exchange in an Organic Solvent 40 mg of NPs were dispersed in THF at a concentration of 1 mg/mL were mixed to 10 mg of the dendrons and magnetically stirred for 24 h. After this period, the suspensions were purified by ultrafiltration. The THF suspension was introduce in the apparatus and purification occurred by pressurizing the solution flow. The solvent and un-grafted molecules (released oleic acid and dendron molecule excess) went through the membrane while grafted nanoparticles did not. The particles were then redispersed in 20 mL. This operation was repeated 3 times. After purification, 10 mg of dendrons were added to the purified suspension, and the suspension was magnetically stirred for another 24h. The nanoparticles were then precipitated by adding hexane. After centrifugation the grafted particles were easily redispersed in distilled water.

Example 21: Characterization of Dendronized NPs

The grafting of dendrons at the surface of nanoparticles after the purification step is confirmed by infra-red (IR) spectroscopy and photoemission spectroscopy (XPS). By IR spectroscopy, the characteristic IR bands of the dendron appear in the IR spectra of dendronized nanoparticles and the P=O and P—OH bands have been modified due to the formation of a bond between phosphonate groups and the iron oxide surface. By XPS, a shift of the P 2p bands is observed after the grafting the dendron through the phosphonate group at the surface of NPs. The observed significant shift is consistent with an environment of oxygen atoms in a more shielded environment than for the single dendron, the oxygen atoms being linked not only to phosphorus but also to the NPs iron atoms. The environment of the phosphorus atoms is less electronegative, the energy required to remove an electron from 2p core levels of phosphorus atoms is thus less significant, which decreases the binding energy. The significant chemical shift shows the formation of a strong binding between phosphonate and iron oxide and the formation of at least a bi- or tri-nuclear-type complex as suggested from IR results.

The grafting rate was determined by elemental analysis of iron and phosphorus in each sample, and by considering the surface covered by one dendritic molecule (the value was deduced from molecular modelling experiments), one may determined the amount of molecule/nm$^2$ or the number of molecule/nanoparticle or the number of molecule/g of nanoparticles.

Example 22: In Vitro Evaluation

I. Hyperthermia Measurements

Preliminary measurements have been done on low concentrated samples and high values of specific absorption rate (SAR) or specific loss power (SLP) values were obtained with core-shell NPs. Oxidized nanocubes display low SAR values by comparison with the results of Pellegrino et al (*ACS Nano* 2012, 6(4), 3080-3091) but this may be attributed to our synthesis process which has led to nanocubes with a lot of defects such as APB and dislocations. At larger concentration, the SAR values strongly decreases indicating thus an effect of the concentration on heating properties. Such an effect of the concentration has already been reported and in particular with nanocubes. Indeed the heat released by magnetic NPs do not depend only on their properties, such as shape, composition and size but also on the interaction between individual NPs. The latter is an important issue intimately related to the efficiency of MH agents that has not been properly addressed in the past years. For NPs with large size (in particular near the superparamagnetic/blocked single domain size threshold), magnetic interactions are strong and NPs tend to aggregate or align in chains during magnetic field application. The role that dipolar interactions may have in SAR is not completely understood at present, and recent experimental studies have reported either an increase or decrease of SAR with interactions (*Scientific reports* 2013, 3, 1652 and references herein). Overall, results suggest a widely negative influence of dipole-dipole interactions on the heating power of nanoparticles. Some measurements have been performed as a function of the concentration (FIG. 1) and a decrease of the heating power is noticed when the Fe concentration increases.

However quite large heating values are obtained in the range of those reported for the best spherical single-core maghemite NPs and magnetite nanocubes. Very recent evaluations of these interaction effects pointed out that chains of magnetic NPs are ideal for obtaining high heating properties. Indeed it has been demonstrated with cubic shaped NPS that the different geometrical arrangement of nanoparticles in suspensions may play some role in explaining the increase of SAR for nanocubes compared to spherical particles. Indeed chains of nanocubes formed due to the existence of strongly anisotropic dipolar forces mediating nanoparticle attachment. In the case of the present invention, the formation of chains with core-shell nanocubes was observed (FIG. 2) without applying a magnetic field and may thus explain the high heating values at low concentration. At high concentration, aggregates certainly form enhanced by dipolar interactions and then the benefit effect of the geometric arrangement is lost and the heating power decreased as usually observed with the increase in dipolar interactions.

II. In Vitro MRI

Relaxivity measurements were performed on all dendronized NPs at 0.47 (20 MHz), 1.41 (60 MHz) and 7 T (300 MHz). The longitudinal and transverse relaxivities are given in Table 1 and compared to the commercial product Endorem® and to 10 nm spherical $Fe_3O_4$ nanoparticles (NS10), the synthesis and functionalization of which have already been described (*Dalton Transaction* 2013, 42, 2146-2157) and which may be considered as a reference. Here the question is to investigate if the spinel iron oxide may act as a T2 contrast agent even under the form of a shell in core-shell FeO@$Fe_3O_4$ NPs and what is the impact of this structure on the relaxivity values. To be used as T2 contrast agent, the NPs have to display both a high transverse relaxivity r2 and a high ratio r2/r1.

All core-shell structures NS19, NC16 and NO24 exhibit much higher $r_2$ and $r_2/r_1$ values than NS10 at 20 MHz and 60 MHz. The same tendency is also observed at 300 MHz excepted for NO24 that seems to behave differently from the other core-shell NPs. Here, in the case of core-shell structures, only the magnetite shell contributes to the magnetization and to the $r_2$ values. Thus the relaxivity values have also been calculated by considering only the iron amount coming from the magnetite phase. However one may notice that the ratio $r_2/r_1$ does not depend on this parameter and thus this ratio confirmed the aforementioned results. By contrast, oxNCl6 present the highest $r_2$ values: 201, 222 and 509 $s^{-i} \cdot mMol^{-1}$ at 20, 60 and 300 MHz respectively. These values are much higher than those recorded for the different core-shell structures and also for the 10 nm spherical NPs.

The mean diameter of the unfunctionalized nanoparticles is determined by measuring the diameter of at least 300 nanoparticles on Transmission Electron Microscopy (TEM) images. The size of the functionalized nanoparticles in suspension is determined by dynamic light scattering (DLS), a method for granulometric measurements.

The contrast enhancement properties of all NPs were also evaluated in vitro by MRI at 7 T and ghost images (FIG. 4A) evidenced a very strong T2 effect as illustrated by the strong negative T2w contrast Enhancement Contrast ratio (EHC) [EHC (%)w=[(Signal value at each equivalent iron concentration)–(signal value of water))/signal value of water)×100] were extracted from T1w and T2w images of samples containing increasing iron concentration diluted in water (FIG. 3).

Core shell nanocubes and spherical NPs display high T2w EHC even at low iron concentration. The smaller values with NO24 may be related to their lower amount in spinel iron oxide by comparison with former NPs. The higher negative T2w EHC values obtained for oxidized nanocubes oxNC16 confirmed their high contrast power even at high magnetic field (7 T) and even at very low iron concentrations. MR images (FIG. 4A), samples with concentration in iron larger than 1.5 mM were not detected due to their dramatic inhibition of the signal, preventing the quantification of their EHC, superior to 100%. The EHC measurements as a function of the iron concentration detailed in FIG. 4B evidenced a very important T2 effect even at low iron concentration. This strong T2 effect is also confirmed by the calculation of the transverse relaxivity rate (R2), estimated at 509 $mmol \cdot l^{-1} \cdot s^{-1}$ (FIG. 4D), and the longitudinal relaxivity rate (R1) at 7.1 $mmol \cdot l^{-1} \cdot s^{-1}$, and consequently their high R2/R1 ratio (71.8). These values are among the largest values reported in the literature.

For all NPs a hyposignal in T1w images is observed (FIG. 4A): this effect is very weak at low iron concentration and increases with increasing iron concentrations. The strong T1w shortening at high concentration is related to the strong T2 shortening and also is certainly due to a clustering of NPs favored by the high concentration of samples.

Example 23: In Vivo Evaluation

Core-Shell Spherical NS19

Core-shell spherical NS19 (example 15) diluted in human injectable water solution were injected by intra-venous route via a catheter at a concentration of 1 μMol/kg, which is a low concentration considering usual injected concentrations. No adverse effect in rats was observed following the intravenous injection, even 3 months after injection. The MRI signal in different organs was followed as a function of time and is presented in FIG. 5. A high negative contrast is observed just after the injection in the blood, cortex and pelvic (ECH=−38%, −31% and −23% respectively) and then increased over the experiment duration because of the dilution of the NPs in the different organs and remained

TABLE 1

Relaxivities r1 and r2 ($s^{-1} \cdot mMol^{-1}$) calculated from the total amount of iron in each sample

| | TEM (mm) | DLS (mm) | Relaxivities at 20 MKz | | | Relaxivities at 60 MKz | | |
|---|---|---|---|---|---|---|---|---|
| | | | r1 $s^{-1} \cdot mM^{-1}$ | r2 $s^{-1} \cdot mM^{-1}$ | r2/r1 | r1 $s^{-1} \cdot mM^{-1}$ | r2 $s^{-1} \cdot mM^{-1}$ | r2/r1 |
| NS19 | 19 | 42 | 20.6 | 163.6 | 8.0 | 7.2 | 201.9 | 27.9 |
| NC16 | 16 | 74 | 13.2 | 113.3 | 8.6 | 5.1 | 116.1 | 22.9 |
| NO24 | 21 | 55 | 7.4 | 65.8 | 8.8 | 2.8 | 80.3 | 28.5 |
| oxNC16 | 16 | 42 | 24.0 | 200.7 | 8.4 | 8.1 | 221.5 | 27.4 |
| NS10 | 10 | 15 | | | | 13 | 78 | 6 |
| Endorem | ND | 120-130 | | | | 10 | 141 | 13 | slightly negative. The strong decrease of T2w signal may be related to an aggregation of NPs at the injection and the evolution of the signal with time suggests a fragmentation of these aggregates upon blood circulation.

The signal in liver evolved similarly to that of blood with time suggesting that the liver signal is mainly due to blood circulation in this organ and that there is no captation by the RES. The signal is in the range [−15; −5] in the kidney and bladder and the decrease of the bladder signal with time suggests an urinary elimination.

The T1w signal depicted in FIG. 5D evolved as expected with time. The strong decrease after injection in blood is in agreement and correlated to the strong negative contrast observed on T2w images (FIG. 5B).

These in vivo results confirm the in vitro one and allow us to conclude that core-shell structure with a wustite core and a magnetite shell can be used as contrast agent for MRI even at low iron concentration.

Oxidized Nanocubes oxNC16

In vivo studies were also conducted with dendronized oxidized nanocubes oxNC16 described in example 2, which were shown to display very interesting in vitro contrast properties. The T2w signals as function of time after IV in different organs are given in FIG. 6A. One may notice that the different curves evolved similarly to those of spherical core-shell NPs: the NPs tend to aggregate after IV (negative signal in blood and liver curves), then the signal stabilized. Finally it increased up to zero in the blood due to the decrease of NPs concentration in the blood related to the organs uptake. The decrease of the signal in bladder would suggest an urinary elimination.

The T1w signals in organs are displayed in FIG. 6B and their evolutions were the one expected. But the one observed in the blood was quite different and interesting. Indeed a high positive contrast was observed between 10 and 17 minutes (FIG. 6D). One may notice that the same signal was negative in the same range of times and conditions in the case of spherical core-shell NPs (FIG. 5D). Such high positive contrast could be explained by the aggregation state of nanocubes. It has demonstrated by Roch and al. (*Journal of Magnetism and Magnetic Materials* 2005, 293, 532-539) that depending on the level of aggregation of NPs, different type of contrast may be noticed.

suggests that for this range of concentration either T1 or T2 MRI can be performed. Such behavior for low concentration may be related to the ability of nanocubes to align in chains at low concentrations.

For higher concentration, no more positive contrast is observed and only a negative contrast is noticed.

Whatever the concentrations: after 1 hour, the T2w signal slightly increased and reached zero, proving the elimination of the NPs from the blood after 1 hour.

Thus the different contrast evolution in the blood according to the iron oxide concentration may be related to the formation of aggregates with different sizes depending on the NPs concentration. At concentration higher than 2 mM/kg, large aggregates are formed leading to high negative and low positive contrasts. For concentration lower than 2 mM/kg, smaller aggregates should be formed leading to both high positive and negative contrast.

More precisely, probably the aggregation of nanocubes in blood was a dynamic equilibrium providing aggregate sizing roughly the maximum size allowing the maximal enhancing of the longitudinal relaxivity.

Noteworthy is that 1 µmol of iron/kg corresponding to the 1 eqIM injected in a 298 g weighting rat is 50 time less than the usual dose used for preclinical MRI studies. A very interesting positive T1w contrast was provided in the main organs (FIG. 6B) and large vessels, allowing to have a dual contrast agent (i.e. positive enhancement of contrast on T1w. images and negative enhancement of contrast on T2w images) with an improvement of the sensitivity related to the bright signal and thus improve the accuracy of the imaging interpretation.

Example 24: Coupling with Targeting Compound ICF01102

Coupling was performed with dendronised nanoparticles of the present invention, said dendrons being terminated by carboxylic acid groups.

Coupling Procedure with ICF01102

ICF01102 has the following formula:

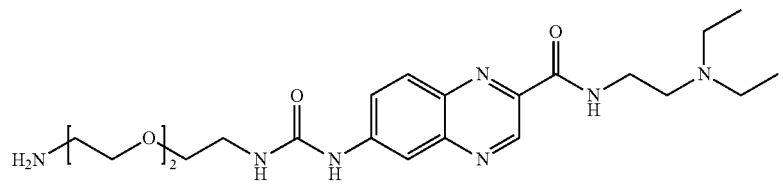

The enhancement of signal appears more dependent on the aggregation state of oxidized nanocubes by comparison with core-shell spherical NPs.

To try to evidence an effect of the aggregation state of NPs on the observed contrast, in vivo MRI studies have been performed by varying the injected concentration.

Influence of the Iron Oxide Concentration

T1w and T2w EHC signals have been followed in different organs as function of the time delay after IV injection and as function of the injected concentration. Only the T1w and T2w Enhancement signal contrast in the blood (aorta) are presented on FIG. 7.

For iron concentration smaller than 2 mM/kg, a positive contrast is observed as well as a negative contrast. That 20 mg of EDCl were added to a suspension of dendronised nanoparticles of the present invention in water. The resulting mixture was then stirred for 30 minutes. 8 mg of ICF01102 were then added to said mixture, which was stirred for 1 hour.

Colloidal stability of the dendronised nanoparticles of the present invention bearing ICF01102 (NP@dendrons+ICF) was checked by DLS.

The presence of the ICF01102 does not modify the size distribution, which stays monomodal. The mean hydrodynamic diameter after coupling with ICF01102 is close to the diameter of dendronised nanoparticles of the present invention before said coupling (NP@dendrons) (FIG. 9).

Zeta potential was measured at pH 7.4 before and after coupling with ICF01102.

Zeta potential after coupling increases slightly, indicating that some of the carboxylic acids groups were coupled with ICF01102 (FIG. 10).

Melanine targeting with NP@dendrons+ICF nanoparticles was followed by fluorescence.

Thus, a fluorophore (Dye 647) was further coupled after coupling with ICF01102 by a method known by hose skilled in the art.

This fluorophore is necessary to follow the course of the NP in optical imaging.

The presence of ICF01102 and the fluorophore on the NPs surface was confirmed by UV-visible spectroscopy (FIG. 11).

Targeting of Melanine Granules

A melanoma was induced by a subcutaneous injection at the side of a mouse of B16F0 cells (300,000 cells). The tumor is measurable from 12 days after injection of the tumor cells (FIG. 12).

The biodistribution of the NPs was followed at different times by optical imaging. Two hours after injection of the NPs, a fluorescence signal was observed in the urine and the gastrointestinal tract. At 4 hours, the urinary excretion was complete but a signal was still observed in the digestive tract. 24 hours after injection, all NPs have been eliminated. This once again confirms the proper elimination of the dendronized NPs, even with the targeting ligand melanin on the surface of said NPs. Rapid urinary excretion (2 hours) and then a slower hepatobiliary elimination was observed (FIG. 13).

The melanoma tumors can not be observed by optical imaging as they appear black because of their high content of melanin. Therefore, they were observed by confocal microscopy (VivaScope 1500, Caliber Inc, Rochester, N.Y., USA, distributed in France by Mavig, Munich).

To show targeting of dendronized NPs in vivo, NPs coupled to ICF ligand and fluorophore Dye 647 (NP@dendrons+ICF+Dye647, emitting in the near IR) and dendronized NPs that are not bearing the ICF ligand but coupled to a fluorophore Dye 495 ((NP@dendrons+Dye495, green emitting) were injected simultaneously intravenously to mice wherein have been grafted malignant melanoma tumor cells. After injection, tumors were removed and imaged ex vivo by confocal microscopy in reflectance mode and fluorescence at 488 nm and 658 nm Melanin in the form of granules in the cytoplasm of the tumor cells has significant autofluorescence. Indeed, these granules correspond to the white dots on the reflectance image shown in FIG. 14*a*). After excitation in the red, a significant fluorescence is visible within the tumor cells (FIG. 14*b*). The superposition of the autofluorescence of the granules in the visible and fluorescence shows colocalization of targeting NPs and melanin granules (FIG. 14*c*).

While by excitation by the blue, no fluorescence corresponding to non targeting NPs (green fluorescence) is observed (FIG. 14*d*).

The in vivo targeting is effective, important, since many NPs were internalized by tumor cells. Targeting is also specific as there is no uptake of non targeting NPs i.e. not functionalized by the ICF ligand.

The presence of NPs in tumors has also been proven by imaging by TEM tumors after having calcined them (FIG. 15).

Example 25: Synthesis of Nanoplatelets (Also Called Nanoplates)

Iron Stearate Complex Synthesis.

The iron stearate was prepared by ligands exchange between iron chloride and sodium stearate in water. At first, 40 mmol of $FeCl_3 \cdot 6H_2O$ was dissolved in distilled $H_2O$ and mixed with 80 mmol of sodium stearate under vigorous stirring. The mixture was heated, under stirring, at 70° C. for 4 h. The stearate complex was, then, washed several times with warm distilled water (50° C.) to remove the chloride traces and the formed NaCl and then conserved at 4° C.

Synthesis of Nanoplates:

a mixture of 2.08 g (2.32 mmol) of the synthesized stearate, 0.2 mL (0.65 mmol) of oleic acid and 0.705 g (2.32 mmol) of sodium oleate used as surfactants was added to 20 mL of octadecene (90%, Alfa Aesar, bp 318° C.). The mixture was, first, heated at 120° C. in the absence of a reflux condenser for 30 min and then to its boiling temperature (~318° C.) with a heating rate of 5° C./min and refluxed for 60 min at this temperature under air. After cooling to the room temperature, the NPs were precipitated by the addition of an excess of acetone and washed 3 times by a mixture of hexane/acetone (1/3) followed by centrifugation (14000 rpm, 10 mn). Finally, the as-obtained NPs were easily suspended in organic solvents.

The invention claimed is:

1. A functionalized metallic oxide nanoparticle comprising:
   a metallic oxide nanoparticle and at least two compounds selected from the following compounds:

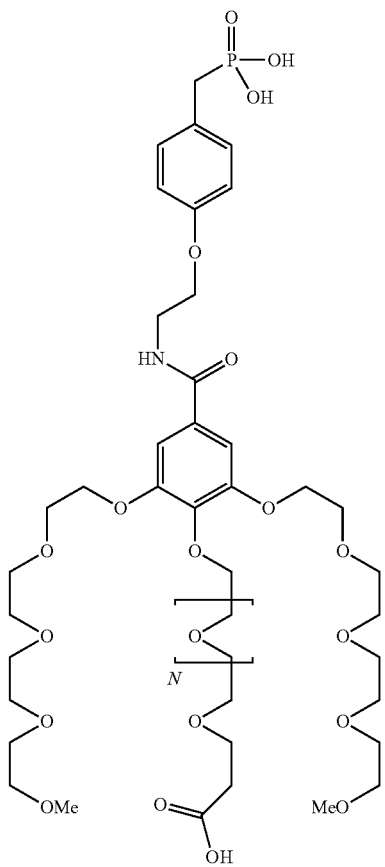

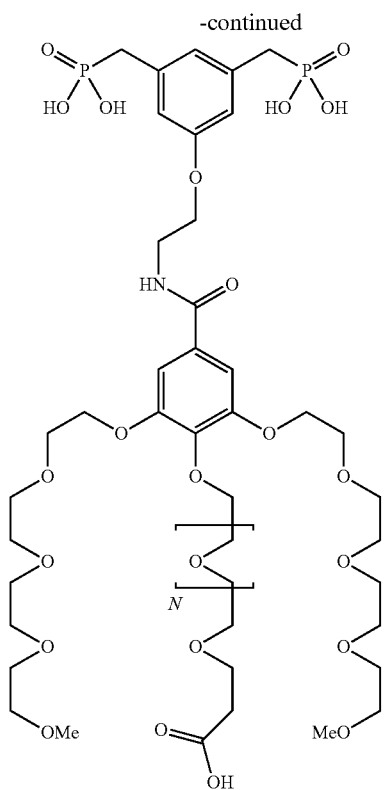

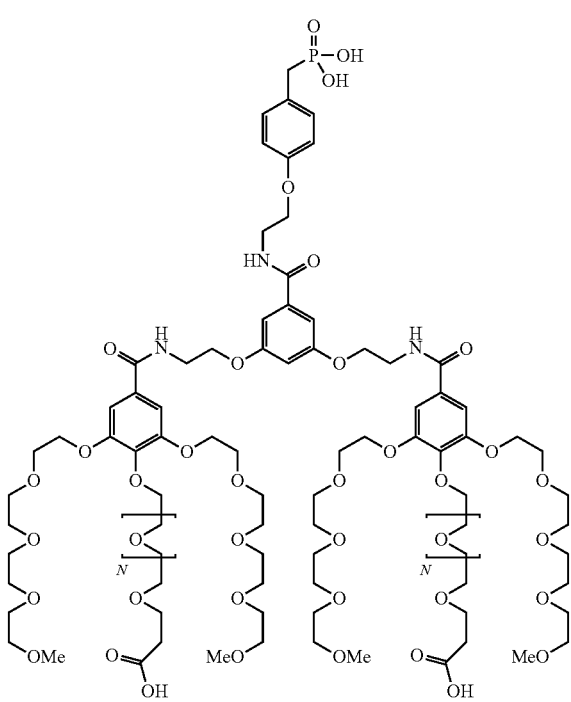

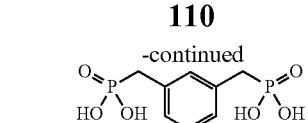

said compounds being iono-covalently bound to said metallic oxide nanoparticle via the $PO_3H_2$ groups these compounds can be functionalized by:
a ligand targeting tumor cells, abnormal cells in respect to their metabolic state or their activation state, or elements constituting an extracellular matrix,
a radioelement chelant;
a specific molecule recognition agent, being able to form a complex with said specific molecule, optionally linked to another dendrimer, said metallic oxide nanoparticle being:
a homogenous metallic oxide nanoparticle selected from the group consisting in:
a metallic oxide of the following formula (II):

$$M_xO_y \quad (II)$$

wherein:
M is Fe,
x and y are positive integers such as $y=(x \cdot v)/2$, wherein v is the average oxidation state of M in $M_xO_y$,
a metallic oxide of the following formula (III):

$$Fe_{3-y}M'_yO_4 \quad (III)$$

wherein M' is a metal selected from the group constituted of Zn, Co, Ni and Mg, y being such as $0<y\leq 1$,
or
a core-shell metallic oxide nanoparticule,
said core being selected from the group constituted of:
a metallic oxide of the following formula (II):

$$M_xO_y \quad (II)$$

wherein:
M is Fe,
x and y are positive integers such as $y=(x \cdot v)/2$, wherein v is the average oxidation state of M in $M_xO_y$,
a metallic oxide of the following formula (III):

$$Fe_{3-y}M'_yO_4 \quad (III)$$

wherein M' is a metal selected from the group constituted of Zn, Co, Ni and Mg, y being such as $0<y\leq 1$, said shell being selected from the group constituted of:

a metallic oxide of the following formula (II):

$$M_xO_y \qquad (II)$$

wherein:
M is Fe,
x and y are positive integers such as y=(x·v)/2, wherein v is the average oxidation state of M in $M_xO_y$,
a metallic oxide of the following formula (III):

$$Fe_{3-y}M'_yO_4 \qquad (III)$$

wherein M' is a metal selected from the group constituted of Zn, Co, Ni and Mg, y being such as 0<y≤1,
Au,
provided that:
said core and said shell are not the same metallic oxide,
said metallic oxide nanoparticle:
being a magnetic resonance imaging contrast agent, and
having a sufficient heating power for a magnetic hyperthermia treatment,
the functionalized metallic oxide nanoparticle being a dendronized nanoparticle operative as both a T2 MRI contrast agent and an agent for hyperthermia therapy.

2. The functionalized metallic oxide nanoparticle according to claim 1, said nanoparticle having
a $r_2$ relaxivity value above 60 $s^{-1}$ $mM^{-1}$, and a relaxivity ratio such that the $r_2/r_1$ ratio is above 6,
said $r_1$ and $r_2$ values being measured with a nanoparticle having a mean hydrodynamic size of about 15 nm, and under a magnetic field of 1.41 T at 37° C., and
a specific absorption rate above 80 W/g, said rate being measured at a concentration of iron and/or magnetic metallic atom in said nanoparticle of 0.01 mol/L, at a field frequency of 700 kHz with a field amplitude of 27 mT and at 37° C.

3. The functionalized metallic oxide nanoparticle according to claim 2, comprising an iron oxide.

4. The functionalized metallic oxide nanoparticle according to claim 1, said nanoparticle having a $r_1$ relaxivity value comprised from 4 to 5 $s^{-1}$ $mM^{-1}$, and a $r_1$ relaxivity ratio such that the $r_2/r_1$ ratio is comprised from 4 to 5, $r_1$ and $r_2$ values being measured with a nanoparticle having a mean hydrodynamic size of about 15 nm, under a magnetic field of 1.41 T at 37° C.

5. The functionalized metallic oxide nanoparticle according to claim 1, the largest dimension of which being comprised from 5 to 30 nm.

6. The functionalized metallic oxide nanoparticle according to claim 1, said nanoparticle being:
cubic, rodshaped, octopod-shaped or nanoplatelet-shaped, and/or
a core-shell metallic oxide nanoparticule.

7. A chain of functionalized metallic oxide nanoparticles according to claim 1, said chain being linear.

8. A method for medical imaging comprising the use of a functionalized metallic oxide nanoparticle according to claim 1.

9. A method for the treatment of tumors or other pathological tissues comprising the use of a functionalized metallic oxide nanoparticle according to claim 1, as a hyperthermia and/or radiosensitizing agent.

10. A pharmaceutical or diagnostic composition comprising functionalized metallic oxide nanoparticles according to claim 1, as active agents and a pharmaceutically acceptable vehicle.

* * * * *